(12) United States Patent
Rovati et al.

(10) Patent No.: US 9,365,654 B2
(45) Date of Patent: Jun. 14, 2016

(54) ANTI-TRKA ANTIBODIES, DERIVATIVES AND USES THEREOF

(71) Applicant: Rottapharm Biotech S.r.l., Monza (IT)

(72) Inventors: Lucio Claudio Rovati, Monza (IT); Michela Visintin, Trieste (IT); Gianfranco Caselli, Milan (IT); Gabriele Ugolini, Trieste (IT)

(73) Assignee: ROTTAPHARM BIOTECH S.R.L., Monza (MB) (IT)

( * ) Notice: Subject to any disclaimer, the term of this patent is extended or adjusted under 35 U.S.C. 154(b) by 224 days.

(21) Appl. No.: 13/894,489

(22) Filed: May 15, 2013

(65) Prior Publication Data

US 2013/0336964 A1    Dec. 19, 2013

(30) Foreign Application Priority Data

Jun. 13, 2012   (EP) ..................................... 12171752

(51) Int. Cl.
    *C07K 16/28*     (2006.01)
    *A61K 39/395*    (2006.01)
    *A61K 47/48*     (2006.01)
    *A61K 39/00*     (2006.01)

(52) U.S. Cl.
    CPC ....... *C07K 16/2878* (2013.01); *A61K 39/39541* (2013.01); *C07K 16/2863* (2013.01); *A61K 47/48561* (2013.01); *A61K 47/48569* (2013.01); *A61K 2039/505* (2013.01); *C07K 2317/21* (2013.01); *C07K 2317/33* (2013.01); *C07K 2317/34* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS 7,601,352 B1 * 10/2009 Novak ....................... 424/141.1

FOREIGN PATENT DOCUMENTS

| WO | 00/73344 A2    | 12/2000 |
|----|---------------|---------|
| WO | 2005/061540 A2 | 7/2005  |
| WO | 2006/137106 A2 | 12/2006 |
| WO | 2009/098238 A1 | 8/2009  |

OTHER PUBLICATIONS

Foote et al., J. Mol. Biol. 224 (1992): 487-499.*
Gard et al., Developmental Biology 167 (1995): 596-608.*
Extended European Search Report dated Aug. 2, 2012, which was issued by European Patent Office for a related European Application No. EP12171752.4 (10 pgs.).
Ugolini et al., "The function neutralizing anti-TrkA antibody MNAC13 reduces inflammatory and neuropathic pain," Proceedings of the National Academy of Sciences, vol. 104, No. 8, Feb. 20, 2007, National Academy of Sciences, pp. 2985-2990.
Cattaneo et al., "Functional blockade of tyrosine kinase A in the rat basal forebrain by a novel antagonistic anti-receptor monoclonal antibody," Journal of Neuroscience, New York, NY, USA, vol. 19, No. 22, Nov. 15, 1999, pp. 9687-9697.
Watson et al., "Targetting nerve growth factor in pain what is the therapeutic potential", BIODRUGS: Clinical Immunotherapeutics, Biopharaceuticals and Gene Therapy, ADIS International, FR., vol. 22, No. 6, Jun. 1, 2008, pp. 349-359.
Covaceuszach et al., "Neutralization of NGF-TrkA receptor interaction by the novel antagonistic anti-TrkA monoclonal antibody MNAC13: a structural insight," Proteins: Structure, Function and Genetics, John Wiley & Sons, Inc., USA, vol. 58, No. 3, Feb. 15, 2005, pp. 717-727.
Xu et al., "Diversity in the CDR3 Region of VH is sufficient for Most Anti- body Specificities," Immunity, vol. 13, Issue 1, Jul. 1, 2000, pp. 37-45.
Gilbert et al., "A complementarity-determining region peptide of an antidesmosome autoantibody may interact with the desmosomal plaque through molecular mimicry with a cytoplasmic desmoglein 1 sequence," European Journal of Immunology, vol. 27, No. 5, 1997, pp. 1055-1060.
Berezov et al., "Biacore analysis of rationally designed anti-HER2 exocyclic mimetics of antibodies," BIAJOURNAL, No. 1, 2001, https://www.biacore.com/lifesciences/technology/publications/journal/index.html?section=lifesciences&realsection=lifesciences&c=10441&d=104445&do=download&id=10449, pp. 4-7.
Monnet et al., "Synthetic Peptides Derived from the Variable Regions of an Anti-CD4 Monoclonal Antibody Bind to CD4 and Inhibit HIV-1Promoter Activation in Virus-infected Cells," Journal of Biol. Chem., vol. 274, No. 6, Feb. 5, 1999. pp. 3789-3796.
Barbas et al., "Recognition of DNA by synthetic antibodies," J. Am. Chem. Soc., vol. 116, 1994, pp. 2161-2162.
Barbas et al., "Human autoantibody recognition of DNA," Proc. Natl. Acad. Sci. USA, vol. 92, Mar. 1995, pp. 2529-2533.
Ditzel et al., "Determinants of polyreactivity in a large panel of recombinant human antibodies from HIV-1 infection," Journal of Immunology, vol. 157, No. 2, Jul. 15, 1996, pp. 739-749.
Rader et al., "A phage display approach for rapid antibody humanization: designed combinatorial V gene libraries," Proc. Natl. Acad. Sci. USA, vol. 95, Jul. 1998, pp. 8910-8915.
Klimka, et al., "Human anti-CD30 recombinant antibodies by guided phage antibody selection using cell panning," British Journal of Cancer, vol. 83, No. 2, 2000, pp. 252-260.
Beiboer et al., "Guided selection of a pan carcinoma specific antibody reveals similar binding characteristics yet structural divergence between the original murine antibody and its human equivalent," Journal of Bol. Biol., vol. 296, 2000, pp. 833-849.
LeSauteur et al., "Potent Human p140-TrkA Agonists Derived from an Anti-Receptor Monoclonal Antibody," Journal of Neuroscience, vol. 16. No. 4, Feb. 15, 1996, pp. 1308-1316.

* cited by examiner

Primary Examiner — Robert C Hayes
(74) Attorney, Agent, or Firm — Lucas & Mercanti, LLP.

(57) ABSTRACT

The present invention relates to an antibody, recombinant or synthetic antigen-binding fragments thereof able to recognize and bind an epitope comprised in the TrkA amino acid sequence, medical uses thereof and a pharmaceutical composition comprising at least one of the above antibody, recombinant or synthetic antigen-binding fragments thereof.

5 Claims, 12 Drawing Sheets

| scFv | 1° PHASE - 5 min | 2° PHASE - 25 min (15' - 35') |
|---|---|---|
| | % inhibition vs. PBS | % inhibition vs. PBS |
| CRB0022 | -35.0 | -36.4 |
| CRB0036 | -24.6 | -51.1 |
| CRB0069 | -4.3 | -32.7 |
| CRB0072 | -23.4 | -47.3 |
| CRB0082 | -21.2 | -55.9 |
| CRB0084 | -34.3 | -36.2 |
| CRB0088 | -26.5 | -26.8 |
| CRB0089 | 0.0 | -54.0 |

ANTI-TRKA ANTIBODIES, DERIVATIVES AND USES THEREOF

CROSS-REFERENCE TO RELATED APPLICATION

This patent application claims the benefit of priority from European Patent Application No. 12171752.4, filed Jun. 13, 2012, the contents of which are incorporated herein by reference.

FIELD OF THE INVENTION

The present invention relates to anti-TrkA antibodies and to derivatives thereof which are able to recognise and bind an amino acid sequence comprised in the Nerve Growth Factor NGF-binding site of the high affinity tyrosine kinase receptor of NGF (TrkA), thus acting as NGF antagonists and preventing the functional activation of TrkA by NGF. The antibodies of the invention are useful in the treatment of conditions associated with the expression and/or activity of TrkA, including pain states.

BACKGROUND OF THE INVENTION

Monoclonal Antibodies

Monoclonal antibodies (Mabs) represent the fastest-growing market segment within the pharmaceutical industry. Despite a number of drawbacks, they are particularly appreciated among biotherapeutics, thanks to their unique features, including extremely high target specificity, favourable pharmacokinetics (long half-life) as well as faster development and higher success rate, as compared to small molecules. Soluble ligands and membrane-bound receptors involved in pain signalling represent ideal targets for the Mab, making it possible to obtain anti-pain biologics with higher specificity and/or different mechanism of action (MoA) as compared to currently available analgesics.

The huge body of evidence suggesting that the NGF pathway provides new molecular targets for pain therapy has spurred the development of neutralizing antibodies against NGF and its receptors. In general, antibodies in the whole immunoglobulin format (IgG) are big molecules that do not go through the blood brain barrier when they are systemically administered. As for antibodies targeting the NGF pathway this means they are likely to be effective in periphery (as it is desirable for many pain conditions) but not in central nervous system (CNS). This is a clear advantage, since NGF is known to exert neurotrophic and neuroprotective effects on specific TrkA-expressing cell populations in the CNS, like basal forebrain cholinergic neurons). From a theoretical point of view anti-NGF neutralizing antibodies represent the most efficacious tool to reduce NGF bioactivity, especially if both receptors are thought to be involved; moreover when the neutralizing agent is an antibody in the whole Immunoglobulin format (IgG), it is usually safer to block a ligand instead of a membrane-bound receptor, which would increase the risk of complement-dependent cytolysis (CDC) and antigen-dependent cell cytolysis (ADCC) for the receptor bearing cell. On the other hand, targeting NGF in Peripheral nervous System (PNS) might indirectly affect the concentration of the same factor in CNS, altering the balance between PNS and CNS pools (peripheral sink effect), with possible deleterious effects on NGF-responsive neurons in the CNS; moreover, in certain cases (e.g., the massive release of NGF in a short time, in inflammation) it is much easier to target and block the receptor than the NGF ligand. The neutralisation of either receptor would therefore avoid the drawbacks associated with NGF targeting as well as the side effects depending on signalling through the other receptor.

Various anti-TrkA antibodies have also been generated. One such antibody is the monoclonal called 5C3 as disclosed in WO97/21732. The antibody interacts within the juxtamembrane/IgG2 domain of TrkA receptor. However, this antibody was found to be a TrkA agonist and therefore not useful for inhibiting TrkA-triggered activities and consequently having a therapeutic effect, as reducing pain. As a matter of fact, when binding to TrkA, this antibody does not prevent the functional activation of the receptor, since, on the contrary, it induces the receptor functional activation upon its binding. Moreover it was not raised against specific loops in the TrkAd5 domain that are known to be essential for NGF binding.

An anti-TrkA monoclonal antibody referred to as MNAC13 is disclosed in WO00/73344. This antibody and its derivatives are said to prevent the functional activation of TrkA in a range of biological systems. In particular, the MNAC13 antibody is able to reduce pain in relevant animal models (Ugolini et al., 2007. *Proc Natl Acad Sci USA*. 104: 2985-2990). However, structural evidence (Covaceuszach et al., 2005. *Proteins*. 58: 717-727) demonstrates that the MNAC13 antibody does not interact with the NGF binding site on the TrkA receptor (TrkAd5 domain), whereas it binds to a more N-terminal portion of the TrkA extracellular domain (ECD) (i.e. the TrkAd4 domain).

WO06/131952 discloses medical uses of the MNAC13 antibody in treating chronic pain.

WO05/061540 discloses a method of antibody humanization in which structural data from crystallographic studies are employed to conduct the first design steps of the humanization process. Anti-TrkA antibodies, such as MNAC13, as disclosed in WO00/73344, are described as examples of mouse antibodies humanized using the method. Several different humanized variants of MNAC13 are disclosed in WO09/098,238.

A human antibody and derivatives thereof that acts as a powerful NGF activity antagonist by recognizing and binding specific loops in the TrkAd5 domain essential for NGF binding has not been provided yet. Moreover there is the need to obtain antibodies with a defined binding specificity to fine regulating the activity thereof.

Chronic Pain as a Therapeutic Area of Largely Unmet Need.

Persistent pain represents a major health problem. It can show different levels of severity and is associated to different pathologies, such as back injury, migraine headaches, arthritis, herpes zoster, diabetic neuropathy, temporomandibular joint syndrome, and cancer. Mild pain is presently treated with acetaminophen, aspirin, and NSAIDs. The NSAIDs inhibit COX and thereby reduce prostaglandin synthesis. However, they are associated with gastrointestinal toxicity, and although COX-2-selective inhibitors have significantly reduced adverse gastric effects, there is still a raised risk of cardiovascular disease (Zeilhofer, 2007. *Biochem Pharmacol*. 73: 165-174). Moderate pain can be controlled using corticosteroidal drugs such as cortisol and prednisone, inhibiting phospholipase A2 (Flower and Blackwell, 1979. *Nature*. 278: 456-459). Nonetheless, corticosteroids display remarkable adverse effects including weight gain, insomnia, and immune system weakening. Severe pain may be treated with strong opioids such as morphine and fentanyl. However, long-term use of opiates is limited by several serious drawbacks, including development of tolerance and physical dependence (Przewlocki and Przewlocka, 2001. *Eur J Pharmacol*. 429: 79-91).

As current pain therapies are often poorly effective or have undesirable side effects, an urgent need therefore exists to develop more specifically efficacious drugs directed against new molecular targets, with particular emphasis for the therapeutic area of chronic pain.

Molecular Mechanisms Underlying Pain

Chronic pain may be of either nociceptive or neuropathic origin. In some cases, complex pain syndromes are produced by a combination of both, as it is the case for many types of oncologic pain. Nociceptive pain is induced by noxious mechanical, chemical, or thermal stimuli acting through pain specific receptors, mainly expressed on the peripheral endings of sensory neurons. Activation of nociceptive Ad-fibers (small diameter, rapidly-conducting, and myelinated) and C-fibers (small diameter, slower-conducting, and unmeylinated) results in pain perception. Tonic or chronic nociceptive pain may arise from sustained inflammatory disorders, resulting in hyperalgesia (increased sensitivity to painful stimuli) and/or allodynia (lowering of the threshold beyond which a stimulus is perceived as painful). Neuropathic pain may be induced by neural lesion or dysfunction, sometimes implying central neuroplasticity.

Following injury, inflammatory mediators are released from both damaged tissues and activated immune cells. Proinflammatory cytokines such as tumor necrosis factor-a (TNFa) and interleukin-1 (IL-1) are secreted by neutrophils and activated cells of the monocyte/macrophage lineage. These cytokines may stimulate the release of Nerve growth factor (NGF) both from structural sources (fibroblasts, keratinocytes, and Schwann cells) and from inflammatory cell types (lymphocytes, macrophages, and mast cells). Moreover, mast cell degranulation releases other proinflammatory substances, which make up the so-called inflammatory soup: histamine, cytokines, prostaglandins, bradykinin, serotonin (5-hydroxytryptamine [5-HT]), adenosine triphosphate (ATP) and H+. Upon binding to their own specific receptors on nociceptive neurons, they all contribute to pain signalling (Pezet and McMahon, 2006. *Annu Rev Neurosci.* 29: 507-538).

TrkA Receptor Signalling in Persistent Pain.

Nerve growth factor (NGF) is a multi-functional molecule that exerts its biological functions in a variety of neural and non-neural cells (Levi-Montalcini, 1987. *Science.* 237: 1154-1162), by means of two types of receptors: the TrkA tyrosine kinase receptor and the p75 neurotrophin receptor (p75NTR), belonging to the molecular family of Tumor Necrosis Factor receptors. TrkA mediates the survival and neurite outgrowth-promoting effects of NGF during development. Each NGF dimer binds two TrkA monomers, resulting in dimerization and trans-autophosphorylation of specific tyrosine residues. These phosphotyrosine residues form docking sites for several adaptor proteins coupling the receptor to intracellular signalling pathways including the mitogen activated protein kinase (MAPK), phosphatidylinositol 3-kinase (PI3K) and PLC pathways (Kaplan and Miller, 2000. *Curr Opin Neurobiol.* 10: 381-391); (Huang and Reichardt, 2003. *Annu Rev Biochem.* 72: 609-642). It is known that the exogenous administration of NGF induces pain both in animals and in humans (Mantyh et al., *Anesthesiology.* 115: 189-204) furthermore, the first line of evidence associating NGF signalling and pain comes from genetic studies. For example, congenital insensitivity to pain with anhydrosis is an autosomal recessive disorder characterized by the absence/abnormal development of several subsets of sensory and sympathetic neurons, which makes affected individuals unresponsive to pain and unable to sweat (anhydrosis). Null mutations in the gene encoding TrkA (NTRK1) have been recognized to be responsible for this disorder (Indo, 2001. *Hum Mutat.* 18: 462-471; Indo et al., 2001. *Hum Mutat.* 18: 308-318; Indo et al., 1996. *Nat. Genet.* 13: 485-488).

NGF plays a key role in pain transduction mechanisms in adult nervous system. Peripheral nociceptors strongly express the TrkA and p75NTR receptors and are developmentally and functionally dependent on NGF. NGF is a peripherally produced mediator of several persistent pain states, notably those associated with inflammation, also thanks to its dual action on inflammatory mast cells that are recruited by NGF to the injured or painful site, and are induced by NGF to release inflammatory mediators. NGF is released by mast cells, fibroblasts and other cell types present in peripheral sites where inflammation is taking place. In particular, mast cells seem to play a key role (Woolf et al., 1996. *J Neurosci.* 16: 2716-2723). In fact, they produce NGF and display functional TrkA receptors on their surface in the same time, which makes them capable of responding to NGF itself, (Horigome et al., 1993. *J Biol Chem.* 268: 14881-14887). Thus the NGF-TrkA system appears to mediate mast cell activation through an autocrine loop, allowing local amplification of the activation process.

Therefore, prior art still fails to disclose an anti-TrkA molecule that specifically recognises and binds an epitope in the TrkAd5 domain, comprising the sequence from aa 294 to to aa 299 of TrkA amino acid sequence of SEQ ID NO: 65, and more effectively acts as NGF antagonists specifically preventing the functional activation of TrkA by NGF.

SUMMARY OF THE INVENTION

An object of the invention is an antibody, recombinant or synthetic antigen-binding fragments thereof which is able to recognise and bind a sequence having at least 80% identity to an epitope comprising the sequence from aa. 294 to aa. 299 of the human TrkA amino acid sequence (UniProt P04629|33-796) of SEQ ID NO: 65 (i.e., the sequence VEMHHW, SEQ ID NO: 66).

The antibody, recombinant or synthetic antigen-binding fragments thereof according to the invention is preferably a NGF antagonist.

The antibody, recombinant or synthetic antigen-binding fragments thereof of the invention is able to specifically antagonize the activity of NGF triggered by TrkA, by preventing the functional activation of TrkA by NGF (also known as neutralizing antibodies).

In the present invention an antibody refers to:

a) a monoclonal, a polyclonal or a chimeric, or a humanized, or a deimmunized, or an affinity matured antibody, or a fully human antibody; and b) a recombinant or synthetic antigen-binding fragments thereof, as well as molecules comprising such antigen-binding fragments, including engineered antibody fragments, antibody derivatives, bispecific antibodies and other multispecific molecules.

In a preferred embodiment, said epitope consists of the sequence from aa. 294 to aa. 299 of the human TrkA amino acid sequence of SEQ ID NO: 65 (i.e., the sequence VEMHHW, SEQ ID NO: 66).

In another embodiment of the invention, the above sequence having at least 80% identity to an epitope is the sequence VEQHHW (SEQ ID NO: 67).

The antibody, recombinant or synthetic antigen-binding fragments thereof according to the invention preferably comprises at least one heavy chain complementary determining region (CDRH3) amino acid sequence having at least 80% identity to an amino acid sequence selected from the group consisting of: SEQ ID NOs: 64, 43, 46, 49, 52, 55, 58 and 61.

The antibody, recombinant or synthetic antigen-binding fragments thereof according to the present invention preferably comprises at least one heavy chain complementary determining region (CDRH1) amino acid sequence having at least 80% identity to an amino acid sequence selected from the group consisting of: SEQ ID NOs: 62, 41, 44, 47, 50, 53, 56 and 59.

The antibody, recombinant or synthetic antigen-binding fragments thereof according to the present invention preferably comprises at least one heavy chain complementary determining region (CDRH2) amino acid sequence having at least 80% identity to an amino acid sequence selected from the group consisting of: SEQ ID NOs: 63, 42, 45, 48, 51, 54, 57 and 60.

The antibody, recombinant or synthetic antigen-binding fragments thereof of the invention preferably comprises a heavy chain complementary determining regions (CDRH1) amino acid sequence having at least 80% identity to an amino acid sequence selected from the group consisting of: SEQ ID NOs: 41, 44, 47, 50, 53, 56, 59 and 62 and a heavy chain complementary determining regions (CDRH2) amino acid sequence having at least 80% identity to an amino acid sequence selected from the group consisting of: SEQ ID NOs: 42, 45, 48, 51, 54, 57, 60 and 63 and a heavy chain complementary determining regions (CDRH3) amino acid sequence having at least 80% identity to an amino acid sequence selected from the group consisting of: SEQ ID NOs: 43, 46, 49, 52, 55, 58, 61 and 64.

In a preferred embodiment, the antibody, recombinant or synthetic antigen-binding fragments thereof comprises a CDRH1 amino acid sequence having at least 80% identity to SEQ ID NO: 62, a CDRH2 amino acid sequence having at least 80% identity to SEQ ID NO: 63 and a CDRH3 amino acid sequence having at least 80% identity to SEQ ID NO: 64.

The antibody, recombinant or synthetic antigen-binding fragments thereof according to the present invention preferably comprises one light chain complementary determining region (CDRL3) amino acid sequence having at least 80% identity to an amino acid sequence selected from the group consisting of: SEQ ID NOs: 40, 19, 22, 25, 28, 31, 34 and 37.

The antibody, recombinant or synthetic antigen-binding fragments thereof according to the present invention preferably comprises at least one light chain complementary determining region (CDRL1) amino acid sequence having at least 80% identity to an amino acid sequence selected from the group consisting of: SEQ ID NOs: 38, 17, 20, 23, 26, 29, 32 and 35.

The antibody, recombinant or synthetic antigen-binding fragments thereof according to the present invention preferably comprises one light chain complementary determining region (CDRL2) amino acid sequence having at least 80% identity to an amino acid sequence selected from the group consisting of: SEQ ID NOs: 39, 18, 21, 24, 27, 30, 33 and 36.

The antibody, recombinant or synthetic antigen-binding fragments thereof of the invention preferably comprises a light chain complementary determining regions (CDRL1) amino acid sequence having at least 80% identity to an amino acid sequence selected from the group consisting of: SEQ ID NOs: 17, 20, 23, 26, 29, 32, 35 and 38 and a light chain complementary determining regions (CDRL2) amino acid sequence having at least 80% identity to an amino acid sequence selected from the group consisting of: SEQ ID NOs: 18, 21, 24, 27, 30, 33, 36 and 39 and a light chain complementary determining regions (CDRL3) amino acid sequence having at least 80% identity to an amino acid sequence selected from the group consisting of: SEQ ID NOs: 19, 22, 25, 28, 31, 34, 37 and 40.

In a preferred embodiment of the invention, the antibody, recombinant or synthetic antigen-binding fragments thereof comprises a CDRL1 amino acid sequence having at least 80% identity to SEQ ID NO: 38, a CDRL2 amino acid sequence having at least 80% identity to SEQ ID NO: 39 and a CDRL3 amino acid sequence having at least 80% identity to SEQ ID NO: 40.

The antibody, recombinant or synthetic antigen-binding fragments thereof according to the present invention preferably comprises a heavy chain variable region comprising SEQ ID NOs: 15, 1, 3, 5, 7, 9, 11 or 13.

The antibody, recombinant or synthetic antigen-binding fragments thereof according to the present invention preferably comprises a light chain variable region comprising SEQ ID NOs: 16, 2, 4, 6, 8, 10, 12 or 14.

According to one aspect of the invention, the antibody, recombinant or synthetic antigen-binding fragments thereof according to the present invention comprises:
a) a variable heavy chain comprising a sequence selected from any of CRB0022VH (SEQ ID NO: 1), CRB0036VH (SEQ ID NO: 3), CRB0069VH (SEQ ID NO: 5), CRB0072VH (SEQ ID NO: 7), CRB0082VH (SEQ ID NO: 9), CRB0084VH (SEQ ID NO: 11), CRB0088VH (SEQ ID NO: 13) or CRB0089VH (SEQ ID NO: 15) or variants thereof or
b) a variable light chain comprising a sequence selected from any of CRB0022VK (SEQ ID NO: 2), CRB0036VK (SEQ ID NO: 4), CRB0069VK (SEQ ID NO: 6), CRB0072VK (SEQ ID NO: 8), CRB0082VL (SEQ ID NO: 10), CRB0084VL (SEQ ID NO: 12), CRB0088VL (SEQ ID NO: 14) or CRB0089VL (SEQ ID NO: 16) or variants thereof.

More preferably, the antibody comprises both a variable heavy chain as described in a) above and variable light chain as described in b), i.e. it comprises one of the following 64 combinations of light and heavy chains:

CRB0022VH_CRB0022VK; CRB0022VH_CRB0036VK;
CRB0022VH_CRB0069VK; CRB0022VH_CRB0072VK;
CRB0022VH_CRB0082VL; CRB0022VH_CRB0084VL;
CRB0022VH_CRB0088VL; CRB0022VH_CRB0089VL;
CRB0036VH_CRB0022VK; CRB0036VH_CRB0036VK;
CRB0036VH_CRB0069VK; CRB0036VH_CRB0072VK;
CRB0036VH_CRB0082VL; CRB0036VH_CRB0084VL;
CRB0036VH_CRB0088VL; CRB0036VH_CRB0089VL;
CRB0069VH_CRB0022VK; CRB0069VH_CRB0036VK;
CRB0069VH_CRB0069VK; CRB0069VH_CRB0072VK;
CRB0069VH_CRB0082VL; CRB0069VH_CRB0084VL;
CRB0069VH_CRB0088VL; CRB0069VH_CRB0089VL;
CRB0072VH_CRB0022VK; CRB0072VH_CRB0036VK;
CRB0072VH_CRB0069VK; CRB0072VH_CRB0072VK;
CRB0072VH_CRB0082VL; CRB0072VH_CRB0084VL;
CRB0072VH_CRB0088VL; CRB0072VH_CRB0089VL;
CRB0082VH_CRB0022VK; CRB0082VH_CRB0036VK;
CRB0082VH_CRB0069VK; CRB0082VH_CRB0072VK;
CRB0082VH_CRB0082VL; CRB0082VH_CRB0084VL;
CRB0082VH_CRB0088VL; CRB0082VH_CRB0089VL;
CRB0084VH_CRB0022VK; CRB0084VH_CRB0036VK;
CRB0084VH_CRB0069VK; CRB0084VH_CRB0072VK;
CRB0084VH_CRB0082VL; CRB0084VH_CRB0084VL;
CRB0084VH_CRB0088VL; CRB0084VH_CRB0089VL;
CRB0088VH_CRB0022VK; CRB0088VH_CRB0036VK;
CRB0088VH_CRB0069VK; CRB0088VH_CRB0072VK;
CRB0088VH_CRB0082VL; CRB0088VH_CRB0084VL;
CRB0088VH_CRB0088VL; CRB0088VH_CRB0089VL;

CRB0089VH_CRB0022VK; CRB0089VH_CRB0036VK; CRB0089VH_CRB0069VK; CRB0089VH_CRB0072VK; CRB0089VH_CRB0082VL; CRB0089VH_CRB0084VL; CRB0089VH_CRB0088VL; and CRB0089VH_CRB0089VL.

Particularly preferred anti-TrkA antibodies which fall within the scope of the present invention comprises a plurality of hypervariable regions (CDR), at least one of which, or at least two of which, or at least three of which, or at least four of which, or at least five of which, or six of which is/are selected from the group consisting of:

CDRH1 regions, comprising sequences selected from the group consisting of SEQ ID NOs: 41, 44, 47, 50, 53, 56, 59, 62;
CDRH2 regions, comprising sequences selected from the group consisting of SEQ ID NOs: 42, 45, 48, 51, 54, 57, 60, 63;
CDRH3 regions, comprising sequences selected from the group consisting of SEQ ID NOs: 43, 46, 49, 52, 55, 58, 61, 64;
CDRL1 regions, comprising sequences selected from the group consisting of SEQ. ID NOs: 17, 20, 23, 26, 29, 32, 35, 38;
CDRL2 regions, comprising sequences selected from the group consisting of SEQ. ID NOs: 18, 21, 24, 27, 30, 33, 36, 39; and
CDRL3 regions, comprising sequences selected from the group consisting of SEQ. ID NOs: 19, 22, 25, 28, 31, 34, 37, 40.

Other particularly preferred anti-TrkA antibodies which fall within the scope of the present invention are disclosed herein below:

an anti-TrkA antibody which comprises a heavy chain variable region comprising CDRH1, CDRH2 and CDRH3, and/or a light chain variable region comprising CDRL1, CDRL2, and CDRL3 wherein both CDRHs and CDRLs amino acid sequence are combined as described in the table below:

|  | CDRH1 | CDRH2 | CDRH3 | CDRL1 | CDRL2 | CDRL3 |
|---|---|---|---|---|---|---|
| SEQ ID NO: | 41 | 42 | 43 | 17 | 18 | 19 |
| SEQ ID NO: | 44 | 45 | 46 | 20 | 21 | 22 |
| SEQ ID NO: | 47 | 48 | 49 | 23 | 24 | 25 |
| SEQ ID NO: | 50 | 51 | 52 | 26 | 27 | 28 |
| SEQ ID NO: | 53 | 54 | 55 | 29 | 30 | 31 |
| SEQ ID NO: | 56 | 57 | 58 | 32 | 33 | 34 |
| SEQ ID NO: | 59 | 60 | 61 | 35 | 36 | 37 |
| SEQ ID NO: | 62 | 63 | 64 | 38 | 39 | 40 |
| SEQ ID NO: | 41 | 45 | 46 | 20 | 21 | 22 |
| SEQ ID NO: | 41 | 48 | 49 | 23 | 24 | 25 |
| SEQ ID NO: | 41 | 51 | 52 | 26 | 27 | 28 |
| SEQ ID NO: | 41 | 54 | 55 | 29 | 30 | 31 |
| SEQ ID NO: | 41 | 57 | 58 | 32 | 33 | 34 |
| SEQ ID NO: | 41 | 60 | 61 | 35 | 36 | 37 |
| SEQ ID NO: | 41 | 63 | 64 | 38 | 39 | 40 |
| SEQ ID NO: | 44 | 42 | 43 | 17 | 18 | 19 |
| SEQ ID NO: | 44 | 48 | 49 | 23 | 24 | 25 |
| SEQ ID NO: | 44 | 51 | 52 | 26 | 27 | 28 |
| SEQ ID NO: | 44 | 54 | 55 | 29 | 30 | 31 |
| SEQ ID NO: | 44 | 57 | 58 | 32 | 33 | 34 |
| SEQ ID NO: | 44 | 60 | 61 | 35 | 36 | 37 |
| SEQ ID NO: | 44 | 63 | 64 | 38 | 39 | 40 |
| SEQ ID NO: | 47 | 42 | 43 | 17 | 18 | 19 |
| SEQ ID NO: | 47 | 45 | 46 | 20 | 21 | 22 |
| SEQ ID NO: | 47 | 51 | 52 | 26 | 27 | 28 |
| SEQ ID NO: | 47 | 54 | 55 | 29 | 30 | 31 |
| SEQ ID NO: | 47 | 57 | 58 | 32 | 33 | 34 |
| SEQ ID NO: | 47 | 60 | 61 | 35 | 36 | 37 |
| SEQ ID NO: | 47 | 63 | 64 | 38 | 39 | 40 |
| SEQ ID NO: | 50 | 42 | 43 | 17 | 18 | 19 |
| SEQ ID NO: | 50 | 45 | 46 | 20 | 21 | 22 |
| SEQ ID NO: | 50 | 48 | 49 | 23 | 24 | 25 |
| SEQ ID NO: | 50 | 54 | 55 | 29 | 30 | 31 |
| SEQ ID NO: | 50 | 57 | 58 | 32 | 33 | 34 |
| SEQ ID NO: | 50 | 60 | 61 | 35 | 36 | 37 |
| SEQ ID NO: | 50 | 63 | 64 | 38 | 39 | 40 |
| SEQ ID NO: | 53 | 42 | 43 | 17 | 18 | 19 |
| SEQ ID NO: | 53 | 45 | 46 | 20 | 21 | 22 |
| SEQ ID NO: | 53 | 48 | 49 | 23 | 24 | 25 |
| SEQ ID NO: | 53 | 51 | 52 | 26 | 27 | 28 |
| SEQ ID NO: | 53 | 57 | 58 | 32 | 33 | 34 |
| SEQ ID NO: | 53 | 60 | 61 | 35 | 36 | 37 |
| SEQ ID NO: | 53 | 63 | 64 | 38 | 39 | 40 |
| SEQ ID NO: | 56 | 42 | 43 | 17 | 18 | 19 |
| SEQ ID NO: | 56 | 45 | 46 | 20 | 21 | 22 |
| SEQ ID NO: | 56 | 48 | 49 | 23 | 24 | 25 |
| SEQ ID NO: | 56 | 51 | 52 | 26 | 27 | 28 |
| SEQ ID NO: | 56 | 54 | 55 | 29 | 30 | 31 |
| SEQ ID NO: | 56 | 60 | 61 | 35 | 36 | 37 |
| SEQ ID NO: | 56 | 63 | 64 | 38 | 39 | 40 |
| SEQ ID NO: | 59 | 42 | 43 | 17 | 18 | 19 |
| SEQ ID NO: | 59 | 45 | 46 | 20 | 21 | 22 |
| SEQ ID NO: | 59 | 48 | 49 | 23 | 24 | 25 |
| SEQ ID NO: | 59 | 51 | 52 | 26 | 27 | 28 |
| SEQ ID NO: | 59 | 54 | 55 | 29 | 30 | 31 |
| SEQ ID NO: | 59 | 57 | 58 | 32 | 33 | 34 |
| SEQ ID NO: | 59 | 63 | 64 | 38 | 39 | 40 |
| SEQ ID NO: | 62 | 42 | 43 | 17 | 18 | 19 |
| SEQ ID NO: | 62 | 45 | 46 | 20 | 21 | 22 |
| SEQ ID NO: | 62 | 48 | 49 | 23 | 24 | 25 |
| SEQ ID NO: | 62 | 51 | 52 | 26 | 27 | 28 |
| SEQ ID NO: | 62 | 54 | 55 | 29 | 30 | 31 |
| SEQ ID NO: | 62 | 57 | 58 | 32 | 33 | 34 |
| SEQ ID NO: | 62 | 60 | 61 | 35 | 36 | 37 |
| SEQ ID NO: | 44 | 42 | 46 | 20 | 21 | 22 |
| SEQ ID NO: | 47 | 42 | 49 | 23 | 24 | 25 |
| SEQ ID NO: | 50 | 42 | 52 | 26 | 27 | 28 |
| SEQ ID NO: | 53 | 42 | 55 | 29 | 30 | 31 |
| SEQ ID NO: | 56 | 42 | 58 | 32 | 33 | 34 |
| SEQ ID NO: | 59 | 42 | 61 | 35 | 36 | 37 |
| SEQ ID NO: | 62 | 42 | 64 | 38 | 39 | 40 |
| SEQ ID NO: | 41 | 45 | 43 | 17 | 18 | 19 |
| SEQ ID NO: | 47 | 45 | 49 | 23 | 24 | 25 |
| SEQ ID NO: | 50 | 45 | 52 | 26 | 27 | 28 |
| SEQ ID NO: | 53 | 45 | 55 | 29 | 30 | 31 |
| SEQ ID NO: | 56 | 45 | 58 | 32 | 33 | 34 |
| SEQ ID NO: | 59 | 45 | 61 | 35 | 36 | 37 |
| SEQ ID NO: | 62 | 45 | 64 | 38 | 39 | 40 |
| SEQ ID NO: | 41 | 48 | 43 | 17 | 18 | 19 |
| SEQ ID NO: | 44 | 48 | 46 | 20 | 21 | 22 |
| SEQ ID NO: | 50 | 48 | 52 | 26 | 27 | 28 |
| SEQ ID NO: | 53 | 48 | 55 | 29 | 30 | 31 |
| SEQ ID NO: | 56 | 48 | 58 | 32 | 33 | 34 |
| SEQ ID NO: | 59 | 48 | 61 | 35 | 36 | 37 |
| SEQ ID NO: | 62 | 48 | 64 | 38 | 39 | 40 |
| SEQ ID NO: | 41 | 51 | 43 | 17 | 18 | 19 |
| SEQ ID NO: | 44 | 51 | 46 | 20 | 21 | 22 |
| SEQ ID NO: | 47 | 51 | 49 | 23 | 24 | 25 |
| SEQ ID NO: | 53 | 51 | 55 | 29 | 30 | 31 |
| SEQ ID NO: | 56 | 51 | 58 | 32 | 33 | 34 |
| SEQ ID NO: | 59 | 51 | 61 | 35 | 36 | 37 |
| SEQ ID NO: | 62 | 51 | 64 | 38 | 39 | 40 |
| SEQ ID NO: | 41 | 54 | 43 | 17 | 18 | 19 |
| SEQ ID NO: | 44 | 54 | 46 | 20 | 21 | 22 |
| SEQ ID NO: | 47 | 54 | 49 | 23 | 24 | 25 |
| SEQ ID NO: | 50 | 54 | 52 | 26 | 27 | 28 |
| SEQ ID NO: | 56 | 54 | 58 | 32 | 33 | 34 |
| SEQ ID NO: | 59 | 54 | 61 | 35 | 36 | 37 |
| SEQ ID NO: | 62 | 54 | 64 | 38 | 39 | 40 |
| SEQ ID NO: | 41 | 57 | 43 | 17 | 18 | 19 |
| SEQ ID NO: | 44 | 57 | 46 | 20 | 21 | 22 |
| SEQ ID NO: | 47 | 57 | 49 | 23 | 24 | 25 |
| SEQ ID NO: | 50 | 57 | 52 | 26 | 27 | 28 |
| SEQ ID NO: | 53 | 57 | 55 | 29 | 30 | 31 |
| SEQ ID NO: | 59 | 57 | 61 | 35 | 36 | 37 |
| SEQ ID NO: | 62 | 57 | 64 | 38 | 39 | 40 |
| SEQ ID NO: | 41 | 60 | 43 | 17 | 18 | 19 |

| | CDRH1 | CDRH2 | CDRH3 | CDRL1 | CDRL2 | CDRL3 |
|---|---|---|---|---|---|---|
| SEQ ID NO: | 44 | 60 | 46 | 20 | 21 | 22 |
| SEQ ID NO: | 47 | 60 | 49 | 23 | 24 | 25 |
| SEQ ID NO: | 50 | 60 | 52 | 26 | 27 | 28 |
| SEQ ID NO: | 53 | 60 | 55 | 29 | 30 | 31 |
| SEQ ID NO: | 56 | 60 | 58 | 32 | 33 | 34 |
| SEQ ID NO: | 62 | 60 | 64 | 38 | 39 | 40 |
| SEQ ID NO: | 41 | 63 | 43 | 17 | 18 | 19 |
| SEQ ID NO: | 44 | 63 | 46 | 20 | 21 | 22 |
| SEQ ID NO: | 47 | 63 | 49 | 23 | 24 | 25 |
| SEQ ID NO: | 50 | 63 | 52 | 26 | 27 | 28 |
| SEQ ID NO: | 53 | 63 | 55 | 29 | 30 | 31 |
| SEQ ID NO: | 56 | 63 | 58 | 32 | 33 | 34 |
| SEQ ID NO: | 59 | 63 | 61 | 35 | 36 | 37 |
| SEQ ID NO: | 44 | 45 | 43 | 20 | 21 | 22 |
| SEQ ID NO: | 47 | 48 | 43 | 23 | 24 | 25 |
| SEQ ID NO: | 50 | 51 | 43 | 26 | 27 | 28 |
| SEQ ID NO: | 53 | 54 | 43 | 29 | 30 | 31 |
| SEQ ID NO: | 56 | 57 | 43 | 32 | 33 | 34 |
| SEQ ID NO: | 59 | 60 | 43 | 35 | 36 | 37 |
| SEQ ID NO: | 62 | 63 | 43 | 38 | 39 | 40 |
| SEQ ID NO: | 41 | 42 | 46 | 17 | 18 | 19 |
| SEQ ID NO: | 47 | 48 | 46 | 23 | 24 | 25 |
| SEQ ID NO: | 50 | 51 | 46 | 26 | 27 | 28 |
| SEQ ID NO: | 53 | 54 | 46 | 29 | 30 | 31 |
| SEQ ID NO: | 56 | 57 | 46 | 32 | 33 | 34 |
| SEQ ID NO: | 59 | 60 | 46 | 35 | 36 | 37 |
| SEQ ID NO: | 62 | 63 | 46 | 38 | 39 | 40 |
| SEQ ID NO: | 41 | 42 | 49 | 17 | 18 | 19 |
| SEQ ID NO: | 44 | 45 | 49 | 20 | 21 | 22 |
| SEQ ID NO: | 50 | 51 | 49 | 26 | 27 | 28 |
| SEQ ID NO: | 53 | 54 | 49 | 29 | 30 | 31 |
| SEQ ID NO: | 56 | 57 | 49 | 32 | 33 | 34 |
| SEQ ID NO: | 59 | 60 | 49 | 35 | 36 | 37 |
| SEQ ID NO: | 62 | 63 | 49 | 38 | 39 | 40 |
| SEQ ID NO: | 41 | 42 | 52 | 17 | 18 | 19 |
| SEQ ID NO: | 44 | 45 | 52 | 20 | 21 | 22 |
| SEQ ID NO: | 47 | 48 | 52 | 23 | 24 | 25 |
| SEQ ID NO: | 53 | 54 | 52 | 29 | 30 | 31 |
| SEQ ID NO: | 56 | 57 | 52 | 32 | 33 | 34 |
| SEQ ID NO: | 59 | 60 | 52 | 35 | 36 | 37 |
| SEQ ID NO: | 62 | 63 | 52 | 38 | 39 | 40 |
| SEQ ID NO: | 41 | 42 | 55 | 17 | 18 | 19 |
| SEQ ID NO: | 44 | 45 | 55 | 20 | 21 | 22 |
| SEQ ID NO: | 47 | 48 | 55 | 23 | 24 | 25 |
| SEQ ID NO: | 50 | 51 | 55 | 26 | 27 | 28 |
| SEQ ID NO: | 56 | 57 | 55 | 32 | 33 | 34 |
| SEQ ID NO: | 59 | 60 | 55 | 35 | 36 | 37 |
| SEQ ID NO: | 62 | 63 | 55 | 38 | 39 | 40 |
| SEQ ID NO: | 41 | 42 | 58 | 17 | 18 | 19 |
| SEQ ID NO: | 44 | 45 | 58 | 20 | 21 | 22 |
| SEQ ID NO: | 47 | 48 | 58 | 23 | 24 | 25 |
| SEQ ID NO: | 50 | 51 | 58 | 26 | 27 | 28 |
| SEQ ID NO: | 53 | 54 | 58 | 29 | 30 | 31 |
| SEQ ID NO: | 59 | 60 | 58 | 35 | 36 | 37 |
| SEQ ID NO: | 62 | 63 | 58 | 38 | 39 | 40 |
| SEQ ID NO: | 41 | 42 | 61 | 17 | 18 | 19 |
| SEQ ID NO: | 44 | 45 | 61 | 20 | 21 | 22 |
| SEQ ID NO: | 47 | 48 | 61 | 23 | 24 | 25 |
| SEQ ID NO: | 50 | 51 | 61 | 26 | 27 | 28 |
| SEQ ID NO: | 53 | 54 | 61 | 29 | 30 | 31 |
| SEQ ID NO: | 56 | 57 | 61 | 32 | 33 | 34 |
| SEQ ID NO: | 62 | 63 | 61 | 38 | 39 | 40 |
| SEQ ID NO: | 41 | 42 | 64 | 17 | 18 | 19 |
| SEQ ID NO: | 44 | 45 | 64 | 20 | 21 | 22 |
| SEQ ID NO: | 47 | 48 | 64 | 23 | 24 | 25 |
| SEQ ID NO: | 50 | 51 | 64 | 26 | 27 | 28 |
| SEQ ID NO: | 53 | 54 | 64 | 29 | 30 | 31 |
| SEQ ID NO: | 56 | 57 | 64 | 32 | 33 | 34 |
| SEQ ID NO: | 59 | 60 | 64 | 35 | 36 | 37 |
| SEQ ID NO: | 44 | 45 | 46 | 17 | 21 | 22 |
| SEQ ID NO: | 47 | 48 | 49 | 17 | 24 | 25 |
| SEQ ID NO: | 50 | 51 | 52 | 17 | 27 | 28 |
| SEQ ID NO: | 53 | 54 | 55 | 17 | 30 | 31 |
| SEQ ID NO: | 56 | 57 | 58 | 17 | 33 | 34 |
| SEQ ID NO: | 59 | 60 | 61 | 17 | 36 | 37 |
| SEQ ID NO: | 62 | 63 | 64 | 17 | 39 | 40 |
| SEQ ID NO: | 41 | 42 | 43 | 20 | 18 | 19 |

| | CDRH1 | CDRH2 | CDRH3 | CDRL1 | CDRL2 | CDRL3 |
|---|---|---|---|---|---|---|
| SEQ ID NO: | 47 | 48 | 49 | 20 | 24 | 25 |
| SEQ ID NO: | 50 | 51 | 52 | 20 | 27 | 28 |
| SEQ ID NO: | 53 | 54 | 55 | 20 | 30 | 31 |
| SEQ ID NO: | 56 | 57 | 58 | 20 | 33 | 34 |
| SEQ ID NO: | 59 | 60 | 61 | 20 | 36 | 37 |
| SEQ ID NO: | 62 | 63 | 64 | 20 | 39 | 40 |
| SEQ ID NO: | 41 | 42 | 43 | 23 | 18 | 19 |
| SEQ ID NO: | 44 | 45 | 46 | 23 | 21 | 22 |
| SEQ ID NO: | 50 | 51 | 52 | 23 | 27 | 28 |
| SEQ ID NO: | 53 | 54 | 55 | 23 | 30 | 31 |
| SEQ ID NO: | 56 | 57 | 58 | 23 | 33 | 34 |
| SEQ ID NO: | 59 | 60 | 61 | 23 | 36 | 37 |
| SEQ ID NO: | 62 | 63 | 64 | 23 | 39 | 40 |
| SEQ ID NO: | 41 | 42 | 43 | 26 | 18 | 19 |
| SEQ ID NO: | 44 | 45 | 46 | 26 | 21 | 22 |
| SEQ ID NO: | 47 | 48 | 49 | 26 | 24 | 25 |
| SEQ ID NO: | 53 | 54 | 55 | 26 | 30 | 31 |
| SEQ ID NO: | 56 | 57 | 58 | 26 | 33 | 34 |
| SEQ ID NO: | 59 | 60 | 61 | 26 | 36 | 37 |
| SEQ ID NO: | 62 | 63 | 64 | 26 | 39 | 40 |
| SEQ ID NO: | 41 | 42 | 43 | 29 | 18 | 19 |
| SEQ ID NO: | 44 | 45 | 46 | 29 | 21 | 22 |
| SEQ ID NO: | 47 | 48 | 49 | 29 | 24 | 25 |
| SEQ ID NO: | 50 | 51 | 52 | 29 | 27 | 28 |
| SEQ ID NO: | 56 | 57 | 58 | 29 | 33 | 34 |
| SEQ ID NO: | 59 | 60 | 61 | 29 | 36 | 37 |
| SEQ ID NO: | 62 | 63 | 64 | 29 | 39 | 40 |
| SEQ ID NO: | 41 | 42 | 43 | 32 | 18 | 19 |
| SEQ ID NO: | 44 | 45 | 46 | 32 | 21 | 22 |
| SEQ ID NO: | 47 | 48 | 49 | 32 | 24 | 25 |
| SEQ ID NO: | 50 | 51 | 52 | 32 | 27 | 28 |
| SEQ ID NO: | 53 | 54 | 55 | 32 | 30 | 31 |
| SEQ ID NO: | 59 | 60 | 61 | 32 | 36 | 37 |
| SEQ ID NO: | 62 | 63 | 64 | 32 | 39 | 40 |
| SEQ ID NO: | 41 | 42 | 43 | 35 | 18 | 19 |
| SEQ ID NO: | 44 | 45 | 46 | 35 | 21 | 22 |
| SEQ ID NO: | 47 | 48 | 49 | 35 | 24 | 25 |
| SEQ ID NO: | 50 | 51 | 52 | 35 | 27 | 28 |
| SEQ ID NO: | 53 | 54 | 55 | 35 | 30 | 31 |
| SEQ ID NO: | 56 | 57 | 58 | 35 | 33 | 34 |
| SEQ ID NO: | 62 | 63 | 64 | 35 | 39 | 40 |
| SEQ ID NO: | 41 | 42 | 43 | 38 | 18 | 19 |
| SEQ ID NO: | 44 | 45 | 46 | 38 | 21 | 22 |
| SEQ ID NO: | 47 | 48 | 49 | 38 | 24 | 25 |
| SEQ ID NO: | 50 | 51 | 52 | 38 | 27 | 28 |
| SEQ ID NO: | 53 | 54 | 55 | 38 | 30 | 31 |
| SEQ ID NO: | 56 | 57 | 58 | 38 | 33 | 34 |
| SEQ ID NO: | 59 | 60 | 61 | 38 | 36 | 37 |
| SEQ ID NO: | 44 | 45 | 46 | 20 | 18 | 22 |
| SEQ ID NO: | 47 | 48 | 49 | 23 | 18 | 25 |
| SEQ ID NO: | 50 | 51 | 52 | 26 | 18 | 28 |
| SEQ ID NO: | 53 | 54 | 55 | 29 | 18 | 31 |
| SEQ ID NO: | 56 | 57 | 58 | 32 | 18 | 34 |
| SEQ ID NO: | 59 | 60 | 61 | 35 | 18 | 37 |
| SEQ ID NO: | 62 | 63 | 64 | 38 | 18 | 40 |
| SEQ ID NO: | 41 | 42 | 43 | 17 | 21 | 19 |
| SEQ ID NO: | 47 | 48 | 49 | 23 | 21 | 25 |
| SEQ ID NO: | 50 | 51 | 52 | 26 | 21 | 28 |
| SEQ ID NO: | 53 | 54 | 55 | 29 | 21 | 31 |
| SEQ ID NO: | 56 | 57 | 58 | 32 | 21 | 34 |
| SEQ ID NO: | 59 | 60 | 61 | 35 | 21 | 37 |
| SEQ ID NO: | 62 | 63 | 64 | 38 | 21 | 40 |
| SEQ ID NO: | 41 | 42 | 43 | 17 | 24 | 19 |
| SEQ ID NO: | 44 | 45 | 46 | 20 | 24 | 22 |
| SEQ ID NO: | 50 | 51 | 52 | 26 | 24 | 28 |
| SEQ ID NO: | 53 | 54 | 55 | 29 | 24 | 31 |
| SEQ ID NO: | 56 | 57 | 58 | 32 | 24 | 34 |
| SEQ ID NO: | 59 | 60 | 61 | 35 | 24 | 37 |
| SEQ ID NO: | 62 | 63 | 64 | 38 | 24 | 40 |
| SEQ ID NO: | 41 | 42 | 43 | 17 | 27 | 19 |
| SEQ ID NO: | 44 | 45 | 46 | 20 | 27 | 22 |
| SEQ ID NO: | 47 | 48 | 49 | 23 | 27 | 25 |
| SEQ ID NO: | 53 | 54 | 55 | 29 | 27 | 31 |
| SEQ ID NO: | 56 | 57 | 58 | 32 | 27 | 34 |
| SEQ ID NO: | 59 | 60 | 61 | 35 | 27 | 37 |
| SEQ ID NO: | 62 | 63 | 64 | 38 | 27 | 40 |
| SEQ ID NO: | 41 | 42 | 43 | 17 | 30 | 19 |

-continued

|         | CDRH1 | CDRH2 | CDRH3 | CDRL1 | CDRL2 | CDRL3 |
|---------|-------|-------|-------|-------|-------|-------|
| SEQ ID NO: | 44 | 45 | 46 | 20 | 30 | 22 |
| SEQ ID NO: | 47 | 48 | 49 | 23 | 30 | 25 |
| SEQ ID NO: | 50 | 51 | 52 | 26 | 30 | 28 |
| SEQ ID NO: | 56 | 57 | 58 | 32 | 30 | 34 |
| SEQ ID NO: | 59 | 60 | 61 | 35 | 30 | 37 |
| SEQ ID NO: | 62 | 63 | 64 | 38 | 30 | 40 |
| SEQ ID NO: | 41 | 42 | 43 | 17 | 33 | 19 |
| SEQ ID NO: | 44 | 45 | 46 | 20 | 33 | 22 |
| SEQ ID NO: | 47 | 48 | 49 | 23 | 33 | 25 |
| SEQ ID NO: | 50 | 51 | 52 | 26 | 33 | 28 |
| SEQ ID NO: | 53 | 54 | 55 | 29 | 33 | 31 |
| SEQ ID NO: | 59 | 60 | 61 | 35 | 33 | 37 |
| SEQ ID NO: | 62 | 63 | 64 | 38 | 33 | 40 |
| SEQ ID NO: | 41 | 42 | 43 | 17 | 36 | 19 |
| SEQ ID NO: | 44 | 45 | 46 | 20 | 36 | 22 |
| SEQ ID NO: | 47 | 48 | 49 | 23 | 36 | 25 |
| SEQ ID NO: | 50 | 51 | 52 | 26 | 36 | 28 |
| SEQ ID NO: | 53 | 54 | 55 | 29 | 36 | 31 |
| SEQ ID NO: | 56 | 57 | 58 | 32 | 36 | 34 |
| SEQ ID NO: | 62 | 63 | 64 | 38 | 36 | 40 |
| SEQ ID NO: | 41 | 42 | 43 | 17 | 39 | 19 |
| SEQ ID NO: | 44 | 45 | 46 | 20 | 39 | 22 |
| SEQ ID NO: | 47 | 48 | 49 | 23 | 39 | 25 |
| SEQ ID NO: | 50 | 51 | 52 | 26 | 39 | 28 |
| SEQ ID NO: | 53 | 54 | 55 | 29 | 39 | 31 |
| SEQ ID NO: | 56 | 57 | 58 | 32 | 39 | 34 |
| SEQ ID NO: | 59 | 60 | 61 | 35 | 39 | 37 |
| SEQ ID NO: | 44 | 45 | 46 | 20 | 21 | 19 |
| SEQ ID NO: | 47 | 48 | 49 | 23 | 24 | 19 |
| SEQ ID NO: | 50 | 51 | 52 | 26 | 27 | 19 |
| SEQ ID NO: | 53 | 54 | 55 | 29 | 30 | 19 |
| SEQ ID NO: | 56 | 57 | 58 | 32 | 33 | 19 |
| SEQ ID NO: | 59 | 60 | 61 | 35 | 36 | 19 |
| SEQ ID NO: | 62 | 63 | 64 | 38 | 39 | 19 |
| SEQ ID NO: | 41 | 42 | 43 | 17 | 18 | 22 |
| SEQ ID NO: | 47 | 48 | 49 | 23 | 24 | 22 |
| SEQ ID NO: | 50 | 51 | 52 | 26 | 27 | 22 |
| SEQ ID NO: | 53 | 54 | 55 | 29 | 30 | 22 |
| SEQ ID NO: | 56 | 57 | 58 | 32 | 33 | 22 |
| SEQ ID NO: | 59 | 60 | 61 | 35 | 36 | 22 |
| SEQ ID NO: | 62 | 63 | 64 | 38 | 39 | 22 |
| SEQ ID NO: | 41 | 42 | 43 | 17 | 18 | 25 |
| SEQ ID NO: | 44 | 45 | 46 | 20 | 21 | 25 |
| SEQ ID NO: | 50 | 51 | 52 | 26 | 27 | 25 |
| SEQ ID NO: | 53 | 54 | 55 | 29 | 30 | 25 |
| SEQ ID NO: | 56 | 57 | 58 | 32 | 33 | 25 |
| SEQ ID NO: | 59 | 60 | 61 | 35 | 36 | 25 |
| SEQ ID NO: | 62 | 63 | 64 | 38 | 39 | 25 |
| SEQ ID NO: | 41 | 42 | 43 | 17 | 18 | 28 |
| SEQ ID NO: | 44 | 45 | 46 | 20 | 21 | 28 |
| SEQ ID NO: | 47 | 48 | 49 | 23 | 24 | 28 |
| SEQ ID NO: | 53 | 54 | 55 | 29 | 30 | 28 |
| SEQ ID NO: | 56 | 57 | 58 | 32 | 33 | 28 |
| SEQ ID NO: | 59 | 60 | 61 | 35 | 36 | 28 |
| SEQ ID NO: | 62 | 63 | 64 | 38 | 39 | 28 |
| SEQ ID NO: | 41 | 42 | 43 | 17 | 18 | 31 |
| SEQ ID NO: | 44 | 45 | 46 | 20 | 21 | 31 |
| SEQ ID NO: | 47 | 48 | 49 | 23 | 24 | 31 |
| SEQ ID NO: | 50 | 51 | 52 | 26 | 27 | 31 |
| SEQ ID NO: | 56 | 57 | 58 | 32 | 33 | 31 |
| SEQ ID NO: | 59 | 60 | 61 | 35 | 36 | 31 |

-continued

|         | CDRH1 | CDRH2 | CDRH3 | CDRL1 | CDRL2 | CDRL3 |
|---------|-------|-------|-------|-------|-------|-------|
| SEQ ID NO: | 62 | 63 | 64 | 38 | 39 | 31 |
| SEQ ID NO: | 41 | 42 | 43 | 17 | 18 | 34 |
| SEQ ID NO: | 44 | 45 | 46 | 20 | 21 | 34 |
| SEQ ID NO: | 47 | 48 | 49 | 23 | 24 | 34 |
| SEQ ID NO: | 50 | 51 | 52 | 26 | 27 | 34 |
| SEQ ID NO: | 53 | 54 | 55 | 29 | 30 | 34 |
| SEQ ID NO: | 59 | 60 | 61 | 35 | 36 | 34 |
| SEQ ID NO: | 62 | 63 | 64 | 38 | 39 | 34 |
| SEQ ID NO: | 41 | 42 | 43 | 17 | 18 | 37 |
| SEQ ID NO: | 44 | 45 | 46 | 20 | 21 | 37 |
| SEQ ID NO: | 47 | 48 | 49 | 23 | 24 | 37 |
| SEQ ID NO: | 50 | 51 | 52 | 26 | 27 | 37 |
| SEQ ID NO: | 53 | 54 | 55 | 29 | 30 | 37 |
| SEQ ID NO: | 56 | 57 | 58 | 32 | 33 | 37 |
| SEQ ID NO: | 62 | 63 | 64 | 38 | 39 | 37 |
| SEQ ID NO: | 41 | 42 | 43 | 17 | 18 | 40 |
| SEQ ID NO: | 44 | 45 | 46 | 20 | 21 | 40 |
| SEQ ID NO: | 47 | 48 | 49 | 23 | 24 | 40 |
| SEQ ID NO: | 50 | 51 | 52 | 26 | 27 | 40 |
| SEQ ID NO: | 53 | 54 | 55 | 29 | 30 | 40 |
| SEQ ID NO: | 56 | 57 | 58 | 32 | 33 | 40 |
| SEQ ID NO: | 59 | 60 | 61 | 35 | 36 | 40 |

The antibody, recombinant or synthetic antigen-binding fragments thereof according to the present invention preferably comprises a heavy chain variable region comprising SEQ ID NO: 15 and a light chain variable region comprising SEQ ID NO: 16.

In the present invention "at least 80% identity" means that the identity may be at least 80% or at least 85% or 90% or 95% or 100% sequence identity to referred sequences.

A derivative of said antibody is also object of the invention; wherein the derivative is capable of binding VEMHHW epitope on TrkA receptor.

The anti-TrkA antibodies of the present invention may comprise any suitable framework variable domain sequence, provided that the binding activity to TrkA is substantially retained. For example, the anti-TrkA antibodies of the invention comprise a human subgroup III heavy chain framework consensus sequence. For example, the framework consensus sequence comprises the heavy chain variable domain sequence of claim 1 of U.S. Pat. No. 7,608,453 B2 which is incorporated herein by reference:

(SEQ ID NO: 102)
QVQLVESGGGLVQPGGSLRLSCAASGFTFSSYAMHWVRQAPGKGLEWVSVISGDGSNTYYADSV

KGRFTISRDNSKNTLYLQMNSLRAEDTAVYYCARG---------------DYWGQGTLVTVSS.

The antibody, recombinant or synthetic antigen-binding fragments thereof according to the invention is preferably a monoclonal antibody or a chimeric or a humanized, or a deimmunized or an affinity matured antibody or a fully human antibody.

Another object of the invention is also a nucleic acid molecule encoding the antibody, recombinant or synthetic anti- -continued

|         | CDRH1 | CDRH2 | CDRH3 | CDRL1 | CDRL2 | CDRL3 |
|---------|-------|-------|-------|-------|-------|-------|
| SEQ ID NO: | 62 | 63 | 64 | 38 | 39 | 31 |
| SEQ ID NO: | 41 | 42 | 43 | 17 | 18 | 34 | gen-binding fragments thereof as above defined, preferably said nucleic acid molecule comprises the nucleic acid sequence of SEQ ID NOs: 90 (CRB0089_IgG4 derived VH—CH1-H—CH2-CH3) and 91 (CRB0089_VLCL).

Other objects of the invention are an expression vector encoding the antibody recombinant or synthetic antigen-binding fragments thereof of the invention, a host cell comprising said nucleic acid which preferably produces the antibody, recombinant or synthetic antigen-binding fragments thereof of the invention.

A further object of the invention is a method of producing the antibody, recombinant or synthetic antigen-binding fragments thereof of the invention comprising culturing the above cell that produces the antibody as described above and recovering the antibody from the cell culture.

The antibodies are useful for therapeutic applications in humans. Typically, the antibodies are fully human or chimeric or humanized to minimize the risk for immune responses against the antibodies when administered to a patient. As described herein, other antigen-binding molecules such as, e.g., antigen-binding antibody fragments, antibody derivatives, and multispecific molecules, can be designed or derived from such antibodies.

Antibody-binding fragments of such antibodies, as well as molecules comprising such antigen-binding fragments, including engineered antibody fragments, antibody derivatives, bispecific antibodies and other multispecific molecules, are also object of the invention.

It is a further object of the invention, the antibody, recombinant or synthetic antigen-binding fragments thereof according to the invention for use as a medicament, preferably, for use in the treatment of pain, cancer, neuronal disorders, inflammation-related diseases, diabetes.

It is another object of the invention a pharmaceutical composition comprising at least one antibody, recombinant or synthetic antigen-binding fragments thereof as described above and pharmaceutically acceptable excipients.

Pharmaceutical compositions comprising the antibody and/or a fragment and/or a recombinant derivative and/or a conjugate thereof in admixture with at least one pharmaceutically acceptable excipient and/or vehicle are included in the scope of the present invention.

In a preferred embodiment, the composition according to the invention is for use in parenteral administration.

A further object of the invention is the use of the antibody, recombinant or synthetic antigen-binding fragments thereof according to the invention for inhibiting TrkA.

It is another object of the invention a method of reducing and/or inhibiting TrkA comprising administering an effective amount of the antibody, recombinant or synthetic antigen-binding fragments thereof as described above.

In the present invention mutants of the disclosed CDRs may be generated by mutating one or more amino acids in the sequence of the CDRs. It is known that a single amino acid substitution appropriately positioned in a CDR can be sufficient to improve the affinity. Researchers have used site directed mutagenesis to increase affinity of some immunoglobulin products by about 10 fold. This method of increasing or decreasing (i.e., modulating) affinity of antibodies by mutating CDRs is common knowledge (see, e.g., Paul, W. E., 1993). Thus, the substitution, deletion, or addition of amino acids to the CDRs of the invention to increase or decrease (i.e., modulate) binding affinity or specificity is also within the scope of this invention.

For sake of brevity, the preferred antibody according to the present invention is identified with the name CRB0089_IgG4 (comprising SEQ ID NO: 15 and SEQ ID NO: 16). While the present invention focuses on such antibody, as an exemplification of the present invention, one of ordinary skill in the art will appreciate that, once given the present disclosure, other similar antibodies, and antibody fragments thereof, as well as antibody fragments of these similar antibodies may be produced and used within the scope of the present invention. Such similar antibodies may be produced by a reasonable amount of experimentation by those skilled in the art.

Still preferably, the antibody is a scFv, Fv fragment, a Fab fragment, a F(ab)2 fragment, a multimeric antibody, a peptide or a proteolytic fragment containing the epitope binding region. Preferably the scFv fragment comprises a sequence selected from the group of SEQ ID NOs: 1, 2, 3, 4, 5, 6, 7, 8, 9, 10, 11, 12, 13, 14, 15 and 16.

It is a further object of the present invention a nucleic acid encoding the antibody or functional derivatives thereof of the invention, or hybridizing with the above nucleic acid, or consisting of a degenerated sequence thereof.

The process for the preparation of the monoclonal antibody is within the skills of the man skilled in the art and comprises cultivating host cell and isolating the antibody according to standard procedures.

As far as the industrial aspects of the present invention are concerned, the antibody herein disclosed shall be suitably formulated in pharmaceutical compositions as normally done in this technical field.

The antibodies of the present invention may comprises at least one CDRH as defined above that contains one or more amino acid substitutions, deletions or insertions of no more than 4 amino acids, preferably of no more than 2 amino acids. The antibodies of the present invention may further comprises at least one CDRL as defined above that contains one or more amino acid substitutions, deletions or insertions of no more than 4 amino acids, preferably of no more than 2 amino acids.

In some aspects, the invention comprises a method for treating or preventing pain, cancer, neuronal disorders, inflammation-related diseases, diabetes, the method comprising administering to a subject in need thereof an effective amount of at least one antibody, recombinant or synthetic antigen-binding fragments thereof of the invention simultaneously or sequentially with an agent that specifically blocks said disease.

The antibody, recombinant or synthetic antigen-binding fragments thereof of the invention are neutralizing antibody (i.e. an antibody that reduces or abolishes the biological activity of the related antigen) that binds to TrkA and reduces the likelihood that TrkA binds to NGF.

Preferably, the antibody, recombinant or synthetic antigen-binding fragments thereof of the invention binds to TrkA at a location that overlaps with a location at which NGF binds to TrkA.

The invention provides formulations comprising a therapeutically effective amount of an antibody as disclosed herein, a buffer maintaining the pH in the range from about 4.5 to about 7.5, and, optionally, a surfactant.

The formulations are typically for an antibody as disclosed herein, recombinant or synthetic antigen-binding fragments thereof of the invention as active principle concentration from about 0.1 mg/ml to about 100 mg/ml. In certain embodiments, the antibody, recombinant or synthetic antigen-binding fragments thereof concentration is from about 0.1 mg/ml to about 100 mg/ml. For the purposes herein, a "pharmaceutical composition" is one that is adapted and suitable for administration to a mammal, especially a human. Thus, the composition can be used to treat a disease or disorder in the mammal. Moreover, the antibody in the composition has been subjected to one or more purification or isolation steps, such that contaminant(s) that might interfere with its therapeutic use have been separated therefrom. Generally, the pharmaceutical composition comprises the therapeutic protein and a pharmaceutically acceptable carrier or diluent. The composition is usually sterile and may be lyophilized. Pharmaceutical preparations are described in more detail below.

Therapeutic formulations of the antibody/antibodies can be prepared by mixing the antibody having the desired degree of purity with optional physiologically acceptable carriers, excipients or stabilizers (Remington's Pharmaceutical Sciences 16th edition, Osol, A. Ed., 1980), in the form of lyophilized formulations or aqueous solutions. Acceptable carriers, excipients, or stabilizers are nontoxic to recipients at the dosages and concentrations employed, and may include buffers, antioxidants, preservatives, peptides, proteins, hydrophilic polymers, chelating agents such as EDTA, sugars, salt-forming counter-ions such as sodium; metal complexes (e.g., Zn-protein complexes); and/or non-ionic surfactants such as TWEEN®, PLURONICS® or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (16th edition, Osol, A. Ed., 1980). The formulations to be used for in vivo administration must be sterile. This is readily accomplished by filtration through sterile filtration membranes.

In another embodiment, for the prevention or treatment of disease, the appropriate dosage of anti-TrkA antibody/antibodies of the present invention, will depend on the type of disease to be treated, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg of antibody or fragment thereof is an initial candidate dosage for administration to the patient, whether, for example, by one or more separate administrations, or by continuous infusion. The progress of this therapy is easily monitored by conventional techniques and assays.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds.

Examples of antibody fragments include but are not limited to Fv, Fab, Fab', Fab'-SH, F(ab')2; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called [alpha], [delta], [epsilon], [gamma], and [mu], respectively.

The term "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "deimmunized" antibody is an antibody with reduced immunogenicity based on disruption of HLA binding, an underlying requirement for T cell stimulation.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (HI, H2, H3), and three in the VL (LI, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (LI), 50-52 (L2), 91-96 (L3), 26-32 (HI), 53-55 (H2), and 96-101 (H3) (Chothia and Lesk, J. Mol. Biol. 196:901-917, 1987). Exemplary CDRs (CDR-L1, CDR-L2, CDR-L3, CDR-H1, CDR-H2, and CDR-H3) occur at amino acid residues 24-34 of LI, 50-56 of L2, 89-97 of L3, 31-35B of HI, 50-65 of H2, and 95-102 of H3 (Kabat et al., Sequences of Proteins of Immunological Interest, 5th Ed. Public Health Service, National Institutes of Health, Bethesda, Md., 1991). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of LI, 50-55 of L2, 89-96 of L3, 31-35B of HI, 50-58 of H2, and 95-102 of H3 (See Almagro and Fransson, Front. Biosci. 13: 1619-1633, 2008). Unless otherwise indicated, HVR residues and other residues in the variable domain (e.g., FR residues) are numbered herein according to Kabat et al.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs, See, e.g., Kindt et al. Kuby Immunology, 6th ed., W.H. Freeman and Co., page 91, 2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (See, e.g., Portolano et al., J. Immunol. 150:880-887, 1993; Clarkson et al., Nature 352:624-628, 1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

In another aspect, the antibody or derivatives thereof comprises a heavy chain variable domain (VH) sequence having at least 80%, 85%, 90%, 91%, 92%, 93%, 94%, 95%, 96%, 97%, 98%, 99%, or 100% sequence identity to an amino acid sequence selected from the group of: SEQ ID NOs: 15, 1, 3, 5, 7, 9, 11 and 13.

In another aspect, the antibody or derivatives thereof comprises a light chain variable domain (VK or VL) sequence having at least 80%, 85%, 90%, 91%, 92%, 93%, 94%, 95%, 96%, 97%, 98%, 99%, or 100% sequence identity to an amino acid sequence selected from the group of: SEQ ID NOs: 16, 2, 4, 6, 8, 10, 12 and 14.

In certain embodiments, the VH sequence or VK/VL sequence having at least 80%, 85%, 90%, 91%, 92%, 93%, 94%, 95%, 96%, 97%, 98%, or 99% identity to SEQ ID NOs: 15, 1, 3, 5, 7, 9, 11 and 13 and SEQ ID NOs: 16, 2, 4, 6, 8, 10, 12 and 14, respectively, contains substitutions (e.g., conservative substitutions), insertions, or deletions relative to the reference sequence, but an anti-TrkA antibody comprising that sequence retains the ability to bind to the TrkAd5 domain. In certain embodiments, a total of 1 to 4 amino acids have been substituted, inserted and/or deleted in the sequence of the CDRH3 such as in SEQ ID NO: 49. In certain embodiments, substitutions, insertions, or deletions occur in regions outside the HVRs (i.e., in the FRs).

Preferably, the antibody of the invention is an ScFv antibody CRB0022, CRB0036, CRB0069, CRB0072, CRB0082, CRB0084, CRB0088, CRB0089 (SEQ ID NOs:

94, 95, 96, 97, 98, 99, 101 and 100, respectively). The respective IgG4 are also part of the invention.

In certain embodiments, the antibody, recombinant or synthetic antigen-binding fragments thereof of the invention has a dissociation constant (Kd) of <100 nM, <10 nM, <1 nM, <0.1 nM, <0.01 nM, or <0.001 nM or less, e.g. from $10^{-8}$ M to $10^{-13}$ M, e.g., from $10^{-9}$ M to $10^{-13}$ M.

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (I)-labeled antigen in the presence of a titration series of unlabeled antigen, then capturing bound antigen with an anti-Fab antibody-coated plate (see, e.g., Chen et al., J. Mol. Biol. 293:865-881 (1999)).

Recombinant and/or biotechnological derivatives as well as fragments of any of the above-disclosed anti-TrkA antibodies also fall within the scope of the invention, provided that the binding activity to TrkA is substantially retained.

Within the scope of the present invention are also anti-TrkA antibodies that compete with any of the above-disclosed anti-TrkA antibodies for binding to TrkA.

An anti-TrkA antibody falling within the scope of the present invention is preferably a monoclonal antibody, which is for example produced by recombinant techniques. As an alternative, it is a polyclonal antibody.

A chimeric antibody is for example an antibody comprising antigen binding sequences from a non-human donor grafted to a heterologous non-human, human, or humanized sequence (e.g., framework and/or constant domain sequences). In one embodiment, the non-human donor is a mouse. In a further embodiment, an antigen binding sequence is synthetic, e.g., obtained by mutagenesis (e.g., phage display or SPLINT screening, etc.). In a particular embodiment, a chimeric antibody of the invention has murine V regions and a human C region. In one embodiment, the murine light chain V region is fused to a human kappa light chain. In another embodiment, the murine heavy chain V region is fused to a human IgG1 or a IgG4 C region.

In some embodiments, the antibodies of the invention are of the IgG class (e.g., IgG1 or IgG4) and comprise at least one mutation in E233, L234, G236, D265, D270, N297, E318, K320, K322, A327, A330, P331, and/or P329 (numbering according to the EU index). In some embodiments, the antibodies comprise the mutations L234A/L235A or D265A/N297A.

Antibodies of the IgG4 isotype are shown to be dynamic molecules, undergoing Fab arm exchange in vivo and in vitro. The ability to engage in Fab arm exchange appears to be an inherent feature of IgG4 that involves the third constant domain in addition to the hinge region and that only requires a reducing environment to be activated. In some embodiments, the antibodies of the invention are characterized by S228P mutation in the IgG4 core-hinge that was demonstrated to be involved in the reduction in IgG4 half antibody formation.

The antibodies of the invention bind (such as specifically bind) TrkA and in some embodiments, they modulate (e.g., inhibit) one or more aspects of TrkA signaling (such as TrkA phosphorylation) and/or neutralization of any biologically relevant TrkA and/or TrkA ligand biological pathway and/or treatment or prevention of a disorder associated with TrkA activation (such as increased TrkA expression and/or activity).

The inventors have also found that an isolated full length IgG anti-TrkA antibody of the present invention generally binds human TrkA with a Kd in a nM range or stronger. As is well-established in the art, binding affinity of a ligand to its receptor can be determined using any of a variety of assays, and expressed in terms of a variety of quantitative values. Accordingly, the binding affinity is expressed as Kd values and reflects intrinsic binding affinity (e.g., with minimized avidity effects). Generally and preferably, binding affinity is measured in vitro, whether in a cell-free or cell-associated setting. Any of a number of assays known in the art, including those described herein, can be used to obtain binding affinity measurements, including, for example, Biacore and ELISA.

In some embodiments, the anti-TrkA antibody of the present invention specifically binds to a polypeptide consisting of or consisting essentially of a TrkA (e.g., a human or mouse TrkA), preferably with a Kd of $1 \times 10^{-8}$ M or stronger.

The anti-TrkA antibody of the present invention, as well as the derivatives and fragments thereof, which are capable of recognising and binding the NGF-binding site of TrkA, are advantageously effective in a number of applications, including those discussed herein below.

In a further aspect of the invention there is provided a compound of the invention for the treatment of a disorder for which a TrkA inhibitor is indicated.

In a further aspect of the invention there is provided use of a compound of the invention for the preparation of a medicament for the treatment of a disorder for which a TrkA inhibitor is indicated.

In a further aspect of the invention there is provided a method of treating a disorder in an animal (preferably a mammal, more preferably a human) for which a TrkA inhibitor is indicated, comprising administering to said animal a therapeutically effective amount of a compound of the invention.

Disorder for which a TrkA inhibitor is indicated to include pain, particularly neuropathic, nociceptive and inflammatory pain.

The antibody, recombinant or synthetic antigen-binding fragments thereof according to the present invention are effective in the treatment of both chronic pain and acute pain. The treatment of chronic pain is preferred. The pain may for example be associated with any of the following: pancreatitis, kidney stones, IBD, Crohn's disease, post surgical adhesions, gall bladder stones, headaches, dysmenorrhea, musculoskeletal pain, sprains, visceral pain, ovarian cysts, prostatitis (in particular the chronic abatteric variant), cystitis, interstitial cystitis, post-operative pain, pain due to vertebral fracture associated with osteoporosis, migraine, trigeminal neuralgia, pain from burns and/or wounds, pain associated with trauma, neuropathic pain, pain associated with musculoskeletal diseases, rheumatoid arthritis, ankylosing spondilitis, periarticular pathologies, HIV infection. Osteoarthritis, endometriosis, uterine leiomyomas, oncological pain and, in particular, pain from bone metastases are examples of pathological conditions in which associated pain is reduced by treatment with the anti-TrkA antibodies and derivatives of the present invention.

The antibody, recombinant or synthetic antigen-binding fragments thereof according to the present invention may also be employed to treat cancer. Several tumor types express TrkA. TrkA activation by NGF might underlie tumor growth (e.g. of prostate and pancreatic cancers). TrkA activation by NGF also facilitates the growth and infiltration of nerve fibers into tumor masses. By preventing TrkA activation, it is also possible to significantly reduce the formation of neuromas. Furthermore, the anti-trkA antibodies of the present invention and their derivatives could be coupled to a cytotoxic agent and employed to target cancer cells expressing TrkA.

The antibody, recombinant or synthetic antigen-binding fragments thereof according to the present invention may also be employed in the treatment of various neuronal disorders. It is known that NGF can be used in the treatment of Alzheimer's disease (Cattaneo et al., 2008. *J Alzheimers Dis.* 15:255-283). Unfortunately, it also induces hyperalgesia, due to its action on peripheral TrkA receptors. The antibody, recombinant or synthetic antigen-binding fragments thereof according to the present invention may therefore be used in combination with NGF-based treatments to reduce undesired NGF-evoked hyperalgesia.

The antibody, recombinant or synthetic antigen-binding fragments thereof according to the present invention may also be employed in the treatment of inflammation-related diseases. NGF is released by mast cells, fibroblasts and other cell types in the peripheral sites where inflammatory processes occur. In particular, mast cells appear to play a fundamental role. They produce NGF and at the same time express functional TrkA receptors at their surface. The NGF/TrkA system appears to mediate mastocyte activation through an autocrine positive feedback mechanism which allows local amplification of the algogenic inflammatory signal. Examples of inflammatory disorders that may be treated include inflammatory forms of the urinary tract and of the pelvic region, osteoarthritis, rheumatoid arthritis, asthma.

BRIEF DESCRIPTION OF THE DRAWINGS

The invention will be described now by non-limiting examples referring to the following figures.

DETAILED DESCRIPTION OF THE INVENTION

Examples

Materials and Methods

SPLINT Library from Human Lymphocytes

Figure 1:
FIG. 1. shows the NGF bind TrkA extracellular domain (ECD); the loop chosen for the selection of SPLINT libraries on human TrkA ECD comprises sequence VEMHHW.

The development of therapeutic antibodies for use in the treatment of human diseases has long been a goal for many researchers in the antibody field. One way to obtain these antibodies is through SPLINT libraries constructed from human lymphocytes. SPLINT technology express human scFv (single chain antibody fragment) libraries cloned in pMV1 vector, a vector derived from pLinker220 vector (Visintin et al., 2004. J Immunol Methods. 290:135-153.), as fusion to the VP16 activation domain. The variable regions are linked with a small peptide linker (SGGSTSGSGKPGS-GEGSSGT, SEQ ID NO: 93). pMV1 contains LEU2 gene that permits maintenance of the plasmid and selection on media lacking leucine in yeast strain L40 and the bla gene that permits the selection of plasmid in *E. coli*.

For construction of human SPLINT libraries the peripheral blood donations from one hundred, non-immunized donors were used. Approximately 2-20 ml of blood samples from each donor were collected. B-lymphocytes were isolated from peripheral blood by using Ficoll plaque reagent (Amersham, USA). Briefly, the diluted blood sample (1:1 of blood per PBS) was carefully layered on top of the Ficoll plaque reagent, and then the two phase solution was centrifuged at 400×g for 30 minutes. B-lymphocytes were collected from the interface between the two phases. Total RNA was extracted from B-lymphocytes by RNeasy Mini Kit (Qiagen) according to manufacturer's instruction. Total RNA was prepared from the B lymphocytes and pooled together before being used for the isolation of mRNA. mRNA was prepared using Oligotex mRNA mini kit (Qiagen) according to manufacturer's instruction. ThermoScript™ RT-PCR System (Invitrogen) was used for cDNA synthesis reactions according to manufacturer's instruction. Oligo (dT)20 were used to synthesize cDNA of V-genes repertoire. In order to reduce amplification bias, we performed 62 independent PCR reactions to amplify V gene segments, using all possible combinations within a primer set (data not shown). The primer sequences, which in theory encompass the entire repertoire of human antibody genes, were obtained from IMGT/GENE-DB (Giudicelli et al., 2005. *Stud Health Technol Inform.* 116:3-8.), and modified according to previously published protocols (Sblattero and Bradbury, 1998. *Immunotechnology.* 3:271-278; Marks et al., 1991. *Eur J Immunol.* 21:985-991; Orlandi et al., 1992. *Biotechnology.* 24:527-531). In this method, the individual rearranged heavy- and light-chain variable regions are amplified separately and are linked through a series of overlap polymerase chain reaction (PCR) steps to give the final scFv products that are used for cloning (Visintin et al., 2004. *J Immunol Methods.* 290:135-153).

The PCR reactions included seven VH forward primers paired with four VH reverse primers which generated a total of twenty-eight reactions; whereas four Vκ forward primers paired with four reverse primers generated a total of sixteen reactions; and nine Vλ forward primers paired with two Vλ reverse primers generated a total of eighteen reactions. The PCRs led to the representation in the repertoire of variable regions derived from all conceivable framework assemblies. All primers contained either BssHII or NheI restriction sites or linker sequence. The final pull-through PCR could be done with two primers (PTfw&PTrv). After the final scFv gene repertoires had been sequentially digested with BssHII and NheI, they were ligated directly into pre-digested and dephosphorylated pMV1 vector. From one ligation reaction and thirty electroporations for the library, we were able to obtain the final huSPLINT_09 library consisting of ~$10^8$ different scFv molecules with 0.04% of clones from no-insert ligation. Preparation of TrkA Dimer Bait.

pMICBD1 (Visintin et al., 2004. *J Immunol Methods.* 290: 135-153) vector was used to clone I27 titin modified to expose two loop of human TrkA (SEQ ID NO 68; SEQ: ID NO: 69). The bait was constructed by assembly PCR. The oligodeoxynucleotides for the first step of assembly PCR (Table V upper panel; SEQ ID NOs: 80, 81, 82, 83, 84, 85, 86 and 87) were diluted to 0.125 µg/µL with double distilled water, while the oligodeoxynucleotides for the second PCR step (Table V lower panel; SEQ ID NOs: 88 and 89) were diluted to 0.25 µg/µL. For the first PCR reaction, 4 µL of each oligo, 4 µL of 5 mM dNTPs, 10 µL of 10×PFU buffer (Promega), 1.5 µL of PFU DNA polymerase (Promega, 3 U/µL), and 68.54 µL of double distilled water were combined. This mixture was then subjected to 8 cycles of amplification at 94° C. (1.5 min), 54° C. (2 min), and 72° C. (3 min). During the first cycle, the 94° C. step was performed for 7 min. After the last cycle completed, an additional 5 min 72° C. elongation step was performed. For the second PCR reaction, 1 µL of the crude mixture from the first PCR reaction was mixed with 4 μL of each primer, 4 μL of 5 mM dNTPs, 10 μL of 10×PFU buffer (Promega), 1.5 μL of PFU DNA polymerase (Promega, 3 U/μL), and 75.5 μL of double distilled water. This mixture was then subjected to 25 cycles of amplification. Each cycle consisted of a 30 second 94° C. step, a 2 min 54° C. step, and a 1.5 min 72° C. step. Prior to the first cycle, a 5 min 94° C. step was used. A 5 min 72° C. elongation step was included following the final cycle. The PCR mixtures were analyzed by 1.5% agarose gel electrophoresis and then purified by PCR purification kit (Qiagen). The purified cDNA was then first digested with restriction enzymes EcoRI-BamHI. The digested fragment was subsequently run by gel electrophoresis and the isolated DNA was subjected to gel extraction kit (Qiagen). The purified EcoRI-BamHI fragment was subsequently cloned in pMICBD1 vector. The final construct was checked by sequence analysis and western blot analysis and X-gal assay as previously described (Visintin and Cattaneo, 2001. *Antibody Engineering*. 1:790)(Visintin et al., 2002. *J Mol Biol*. 317:73-83.).

Selection of Anti-TrkAscFv from SPLINT Library.

L40 expressing bait TrkA dimer bait was transformed with 250 μg of human SPLINT library according to the protocol described below:

Day 1: inoculation of L40 containing the bait in 5 ml of YC-UW overnight;

Day 2: inoculation of 100 ml of YC-UW with an aliquot of the overnight culture in order to have a dilution that allows the algorithmic growth phase to be reached the next day; and Day 3: the overnight culture is transferred in 1 l of heated YPAD to obtain a culture with an OD 600=0.3; the yeast is grown at 30° C. for 3 h, the cells are centrifuged at 1500 rpm for 5 min at room temperature; the yeast pellet is washed with 500 ml of 1×TE and then centrifuged at 1500 rpm for 5 min at room temperature; the pellet is resuspended in 20 ml of 1×LiAC, 0.5×TE and transferred to a fresh flask; 250 μg of human SPLINT library and 1 ml of denatured salmon sperm are added; 140 ml of 1×LiAc, 40% PEG 3350, 1×TE; the product is mixed and incubated in a low-speed agitator for 30 min at 30° C.; 17.6 ml of DMSO are added and mixed. Thermal shock is performed for 10 min at 42° C. while agitating occasionally. The product is quickly cooled by adding 400 ml of YPA. The yeast is pelleted by centrifugation and washed once with 500 ml of YPA. After centrifugation, the pellet is resuspended in 1 l of YPAD preheated to 30° C. The product is incubated for 1 h at 30° C.; 1 ml of the culture is isolated and the pellet obtained by centrifugation of this ml is resuspended in 1 ml of YC-UWL. Dilutions of 1:10, 1:100, and 1:1000 are seeded on YC-UWL plates to calculate the efficiency of the transformation. The pellet obtained from the remaining culture is washed twice with YC-WHULK. The final pellet is resuspended in 10 ml of YC-WHULK. The aliquots are plated on YC-WHULK plates and after 3-4 days the colonies that have grown are analyzed to determine the interaction.

Thousand colonies grown on YC-WHULK and testing blue on beta-Gal assay were analyzed by PCR-fingerprinting analysis using the BstNI restriction enzyme. The analysis of digestion patterns and scFv sequences isolated from the HIS+ lacZ+colonies permit the isolation of 189 different scFv which 61 that recognize the bait in a secondary screening (specificity screening) (see Table I).

Expression, Refolding and Purification of scFv from *E. coli* Inclusion Bodies.

cDNA encoding isolated scFvs were cloned into pETM-13 vector (http://www.embl.de/ExternalInfo/protein_unit/draft_ frames_save/flowchart/clo_vector/frame_our_Ec_ vectors.html) for expression and induction of inclusion bodies into the cell cytoplasm of *E. coli*. Appropriate strain must me employed to maximize expression levels: standard choice is BL21(DE3) strain (Novagen). If the codon usage is very different Rosetta 2 (DE3) (Novagen) can be employed. Single colonies carrying the expression plasmid were cultured O/N at 37° C. Next day diluted overnight growths were grown to $OD_{600}$>0.75 and IPTG to 1.5 mM final concentration was added. After 4-5 hours incubation cell were collected and centrifuged at 6000 RPM for 15 minutes. Pellet were frozen at −80° C. Pellet were resuspended in 20 mL of Lysis Buffer (50 mM Tris pH 8, 0.5 mM EDTA, 10 mg/mL DNase, 20 mg/mL Lysozime). The lysates were incubated by shaking for 1 hour. Then the lysated were subsequently sonicated three times for 45 seconds and keep in ice for 1 minute after each sonication. The lysates were centrifuged at 6000 RPM. After centrifugation the supernatant were discarded. Pellets were then resuspended and vortex in 20 mL wash buffer (10 mM Tris pH 8, 1 mM EDTA, 1% Triton X100). After centrifugation at 10000 RPM for 10 minutes the pellets were subsequently resuspended in 20 mL wash buffer 2 (10 mM Tris pH 8, 1 mM EDTA, 1M NaCl). After centrifugation at 10000 RPM for 10 minutes the pellets were subsequently resuspended in 20 mL wash buffer 3 (10 mM Tris pH 8, 1 mM EDTA). After centrifugation at 10000 RPM for 10 minutes the pellets were subsequently resuspended and vortex in 5 mL/g of solubilization buffer (6M Guanidinum, 100 mM Tris pH 8, 1 mM EDTA, 100 mM DTT). The solubilized samples were incubated shaking for 2 hours at room temperature. After centrifugation at 10000 RPM for 10 minutes the supernatant were pH lowered to 3-4 by adding acetic acid. The samples were dialyzed against 250 mL of 6M Guanidinium pH 3.5 (4 hours at RT or 12 hours at 4° C.), three times changing buffer. After the inclusion bodies have been solubilized by high concentrations of denaturing agents, refolding is then accomplished by the controlled removal of excess denaturant. This was allowed to occur in the presence of a suitable redox system and of other folding promotion agents according to the model of "pulse renaturation". Dilution of the solubilized protein (35 mg/L) directly stirring into the renaturation buffer (0.5M Arginine, 100 mM Tris pH 8.5, 5 mM EDTA, 375 mM L-glutathione oxidized (freshly added) was performed every 50 minutes (incubation at 4° C. in the meantime) till all the solubilized sample has been added. After incubation at 4° C. overnight, the samples were dialyzed against 5 L of IEXA buffer (according to the pI of scFv and thus to ionic exchange protocol subsequently employed) 4 hours at RT or overnight at 4° C., with two buffer changes. Centrifuge at 10000 RPM for 10 min and filter were necessary before ion exchange chromatography. The purified proteins were aliquoted and stored at −80° C. after quantification and analysis by Bioanalyzer 2100 (Agilent).

Preparation of TrkA Immunoadhesins.

Soluble human and murine TrkA, TrkB, TrkC and p75NTR receptors were engineered as immunoadhesins (Chamow and Ashkenazi, 1996. *Trends Biotechnol*. 14:52-60) by linking the extracellular domain of the receptors to the Fc portion (immunoglobulin heavy chain constant region) of IgG2a camel antibody (*Camelus dromedarius*) (SEQ ID NOs: 70, 71, 72, 73 and 74). The DNA sequences coding for the immunoadhesins were cloned into pCDNA3 vector (Invitrogen) for expression in mammalian cell lines and the proteins were purified by Protein A-Sepharose chromatography from culture medium. The purified proteins were aliquoted and stored at −80° C. after quantification and analysis by Bioanalyzer 2100 (Agilent).

Figure 7:
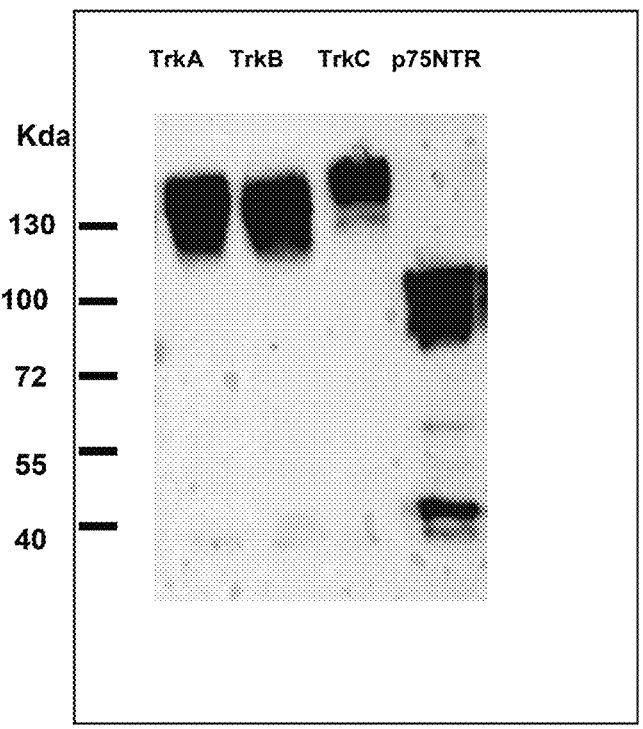
FIG. 7. Western blot analysis of human TrkA, TrkB, TrkC and p75NTR immunoadhesins.

The purified proteins were also subjected to western blot analysis using an anti-Camel antibody (Bethyl) as primary antibody (1:4000) and an anti-rabbit-HRP secondary antibody diluted 1:2000 (DAKO). ECL reagents (Amersham) was used for the detection of the protein according to the manufacturing instruction (FIG. 7).

Specificity ELISA.

Microtitre plate wells were coated with 50 µl of 2 µg/mL human TrkA immunoadhesin, 10 µg/ml bovine serum albumin (BSA) or PBS (the uncoated well). After preblock of the microtitre plates, 50 µl of soluble scFv from each selected clones (at 50-5 µg/mL concentration) was added to a well coated with hTrkA, BSA or an uncoated well. HRP activity was visualized using TMB (Sigma). The results of eight isolated clones are shown in FIG. 7.

Crossreactivity ELISA.

Microtitre plate wells were coated with 50 µl of either 2 µg/ml human TrkA immunoadhesin, 2 µg/ml mouse TrkA immunoadhesin, 10 µg/ml bovine serum albumin (BSA) or PBS (the uncoated well). After preblock of the microtitre plates, 50 µl of soluble scFv from each isolated clone was added to a well coated with either hTrkA, mTrkA, BSA or an uncoated well. As above, HRP activity was visualized using TMB (Sigma). Clones were considered to be cross-reacting with human and mouse TrkA if the ELISA signal generated in the mTrkA coated well was at least 0.5-fold less than the signal on hTrkA (data not shown).

Specificity Determination by BIACore X100™.

The antibodies were also shown to be specific for hTrkA and mTrkA by relative binding to the BIACore sensor chips coated with the appropriate antigen. Antibodies were immobilized by ammine coupling to Biosensor CM5 sensorchips (Pharmacia) according to the manufacturers instructions. Anti-TrkA scFv proteins were diluted at 20-50 µg/ml in suitable pre-concentration buffer (at least 2 pH unit below the pI of the scFv in order to get a net positive charge), chosen among the Acetate buffers. The scFvs were immobilized at 100 RU to get a low density immobilization. As binder, the recombinant protein consisting of D4-D5 domain of human and murine TrkA receptor (hTrkA Ig1,2 and mTrkA Ig1,2 respectively) were injected over the immobilized scFv with a contact time of 60 seconds and with a dissociation time of 400 seconds and the assay workflow placed 5 serial dilutions of the TrkA Ig1,2 (starting in the micromolar range and diluting 1:2 each time). The regeneration condition were mild (contact time 30 seconds, 10 mM Glycine pH2). On the basis of the resulting sensorgrams, the concentrations of TrkA Ig1,2 were adjusted to optimize, contact time, dissociation time and rigeneration. Data were analysed by Bioevaluation Software (see results on Table II and Table III). The quality of the data fitting were checked by the value of $Chi^2$ and of the U-value.

NGF Biological Assay with TF1 Cells.

This is a quantitative assay to measure the functional effect of anti-NGF/TrkA antibodies on the interaction between human NGF and the human TrkA receptor in vitro. TF-1 cells, a human hematopoietic cell line which expresses the native human TrkA receptor but not the p75 NGF-receptor, proliferate in response to exogenous human NGF (Chevalier et al., Blood 1994, vol. 83:1479-85). The TF-1 proliferation assay as described by Chevalier et al., formed the basis for a potency assay to measure the effects of NGF/TrkA neutralising antibodies on the NGF-mediated proliferation of TF1 cells. Before testing with a MTT cell proliferation assay kit (ATCC), TF1 cells are cultured for 1 week in RPMI-1640 containing 10% FBS with 2 ng/ml GM-CSF. Cells for testing are centrifuged (1000 rpm, 5 min), washed (RPMI-1640), centrifuged again and resuspended in RPMI-1640+10% FBS to a concentration of 300,000-400,000 cells/ml. They are then replated on 96-well microplates (15,000-20,000 cells per well in 50 ml) and TrkA neutralising antibodies are added soon after seeding. After 60 min (pre-incubation with TrkA neutralising antibodies), TF1 are exposed to 10 ng/mL NGF in RPMI-1640 containing 10% FBS (50 ml of 2×NGF is added per well, each well has a final volume of 100 ml). Control wells are included, either containing medium alone, or containing TF1 cells in the absence of NGF ("cellular blank"). Each treatment is performed in triplicate. After a 40 h incubation period, at 37° C., 5% $CO_2$, 10 µA of MTT reagent (MTT cell proliferation assay kit) is added for 4 h incubation at 37° C. Thereafter, wells are incubated with Detergent Reagent (MTT cell proliferation assay kit: 100 µl per well; gently mixing, no pipetting) for overnight (O/N) incubation at room temperature in the dark. Absorbance is recorded at 570 nm. 100% inhibition is set as the value of inhibition corresponding to the average O.D. value observed for cells cultured without NGF, in the absence of antibody. 0% inhibition is set as the value of inhibition corresponding to the average O.D. value observed for cells exposed to 10 ng/ml NGF, in the absence of anti-TrkA antibodies.

FACS Analysis of Anti-TrkAscFvs.

Fluorescence activated cell sorter (FACS) is a powerful tool to measure and analyze cell surface molecules of single cells which flow in fluid stream through a beam of light to detect the fluorescences of the cells. FACS was applied to determine the binding profiling of the various scFv onto TF-1 receptor TrkA. FACS Tests are performed only on population with cell viability >95%. Method is an adaptation of protocols reported on the Application Note "Detection of antibody-stained cell surface and intracellular protein targets with Agilent 2100 Bioanalyzer".

$10^6$ cells/sample=tot: $6×10^6$ cells are first centrifuged at 350 g for 5 min at room temperature (RT) and wash with 12 ml of Staining Buffer (SB) at RT. The pellet was resuspended in 3 ml of SB at 4° C. and aliquote 0.5 ml of suspension in 1.5 ml conical tubes. Cells were centrifuged again at 350 g for 5 min at 4° C. and the pellet was resuspended in 1 ml HBSS at 4° C. 125 µl 16% p-formaldehyde (final conc 1.7%) was added into each tube and then the sample was incubated for 10 min at 4° C. on tube rotator. After 10 minutes, 75 µl of 10% detergent solution-Tween 20 (final conc 0.6%) was added and the samples were then incubated for 10 min at 4° C. on tube rotator. Samples were then washed once with FACS Buffer (0.8 ml/sample) at 4° C. and then centrifuged at 350 g for 5 min at 4° C. Cells were resuspended with 80 µl/sample of FACS Buffer. 20 µl of a 5× primary antibody solution were added (final concentration of scFvs is 5 µg/ml). After incubation for 1 hour at 4° C. on tube rotator samples were washed with FACS Buffer (0.5 ml/sample) at 4° C. and then centrifuged 5 min at 350 g at 4° C. Cells were resuspended with 80 µl/sample of FACS Buffer. 20 µl of a 5× secondary antibody solution were added. Final concentration of mouse anti-V5 antibody is 0.20 µg/ml. The samples were incubated for 1 hour at 4° C. on tube rotator. After incubation for 1 hour at 4° C. on tube rotator samples were washed with FACS Buffer (0.5 ml/sample) at 4° C. and then centrifuged 5 min at 350 g at 4° C. Cells were resuspended with 80 µl/sample of FACS Buffer. 20 µl of a 5× tertiary antibody solution were added. Final concentration of anti-mouse IgG-Cy5 is 4 µg/ml (1:250 diluted). The samples were incubated for 1 hour at 4° C. on tube rotator. After incubation for 1 hour at 4° C. on tube rotator samples were washed with FACS Buffer (0.5 ml/sample) at 4° C. and then centrifuged 5 min at 350 g at 4° C. Samples were then resuspended in 300 µl of 304 SYTO16 diluted in FACS Buffer and incubated for 30 min at 37° C. (no mix). After incubation samples were washed with FACS Buffer (0.5 ml/sample) at 4° C. and then centrifuged 5 min at 350 g at 4° C. Cells were then counted in order to obtain a cell suspension of about 2 million cells/ml diluting the pellet with Cell Buffer (Agilent Cell Kit) (100-50 µl depending on the cell pellet). Cells were loaded into the chip as reported in the Agilent Cell Assay Guide. Samples were analysed by the 2100 Expert Software Assay "Antibody Staining Series II". Gates are chosen according to results obtained from negative controls (unrelated primary antibody).

FACS Analysis of Anti-TrkA mAbs.

FACS Tests are performed only on population with cell viability >95%. Method is an adaptation of protocols reported on the Application Note "Detection of antibody-stained cell surface and intracellular protein targets with Agilent 2100 Bioanalyzer".

$10^6$ cells/sample=tot: $6 \times 10^6$ cells are first centrifuged at 350 g for 5 min at room temperature (RT) and wash with 12 ml of Dye Loading Buffer at RT. Cell pellets were resuspended in 2 ml of Dye Loading Buffer. 1 µl of CALCEIN_AM was added then 330 µl/sample are aliquoted in eppendorf and incubated for 30 min at 37° C. in termoblock under dim light. After incubation the samples were washed with FACS Buffer (0.5 ml/sample) at 4° C. and then centrifuged 5 min at 350 g at RT. Cells were resuspended in 100 µl/sample of Antibody Solution (con:0.2-20 µg/ml in FACS Buffer) and then incubated for 1 hour at 4° C. on rotating wheel. Proper controls are included (FACS Buffer). After incubation the samples were washed with FACS Buffer (0.5 ml/sample) at 4° C. and then centrifuged 5 min at 350 g at RT. Cells were resuspended in 100 µl/sample of Antibody Solution in FACS buffer 4 µg/ml (1:500) and incubated for 30 minutes at 4° C. on rotating wheel. After incubation the samples were washed with FACS Buffer (0.5 ml/sample) at 4° C. and then centrifuged 5 min at 350 g at RT. Cells were resuspended in 100 µl/sample of Cell Buffer (Component of Agilent Cell Reagents) and proceeded with the loading of the chip as reported in the Agilent Cell Assay Kit Guide).

NGF Biological Assay with 3T3TrkA Cells.

This assay is described in (Ugolini et al., 2007. *Proc Natl Acad Sci USA*. 104:2985-2990). 3T3-TrkA cells are cultured in DMEM (+10% FBS+1× GlutaMAX+100 units/ml penicillin and 0.1 mg/ml streptomycin) and can be used for the test from 3 days up to 2 months following seeding. The day before the test, cells are seeded in a 6 multi-well plate (2 ml of a suspension containing $5 \times 10^5$ cells per well). The day after, growth medium is removed and adherent cells are washed with PBS (+Ca/Mg) before being incubated with serum-free medium supplemented with 0.05% BSA for 1 h at 37° C. in $CO_2$ incubator. At this step, antibodies or other compounds neutralizing NGF/TrkA are added to the corresponding wells at the diluition/s to be evaluated, so that they are present in the medium for 1 h before testing. At the end of such pre-incubation step, 100 ng/ml of NGF are added to each well (except for negative control) for 10 min at 37° C. in $CO_2$ incubator. After PBS (+Ca/Mg) wash, cells are scraped on ice in 250 ml of cold RIPA buffer supplemented with phosphatases and proteases inhibitors and insoluble material is removed by 5 min 10000 g centrifugation (4° C.). Extracts are separated on SDS polyacrylamide 10% gels and transferred to nitrocellulose using standard protocols. After blocking 1 h at RT with PBS (+5% non fat dry milk) with gentle agitation, filter are incubated O/N at 4° C. with either anti-phospho TrkA antibody (1:1000) or anti-TrkA antibody (1:1000), followed by the corresponding HRP-conjugated secondary antibody (anti-rabbit/anti-goat 1:1000) for 1 h at RT. After 3 washes in PBS containing 0.1% Tween20 and 3 washes in PBS at RT (gentle agitation), the HRP conjugates are detected by ECL.

Reformatting of Anti-TrkA scFvs to Entire IgG Antibodies

Anti-TrkA CRB0089 scFv was reformatted to entire IgG antibodies. The cDNA encoding the light and heavy chain (human $IgG_4$) were generated by GENEART (Germany) with suitable restriction sites for subcloning. Sequences were optimized for mammalian expression (CHO-S cell line) (SEQ ID NOs: 90 for heavy chain and 91 for light chain). After synthesis of both chains, the cDNAs were sub-cloned in expression plasmids (pcDNA3.1 derivates containing an extended CMV promoter for expression of the gene of interest) using HindIII and XhoI as cloning sites. For each antibody chain, two expression plasmids were generated: one plasmid containing the cDNA encoding the light chain, one containing the cDNA encoding the heavy chain. The expression plasmid containing the correct inserts were verified by restriction analysis and DNA sequence analysis of the insert.

Production of Recombinant CRB0089_IgG4 Antibody from Transfected Cells

Anti-TrkA antibody was produced from transfected cells. CHO-S cells were transfected with plasmids encoding CRB0089 heavy and light chains. Conditioned media from transfected cells were recovered by removing cells and debris. Clarified conditioned media were loaded onto protein A-sepharose column. Non-specific bindings were removed by extensively binding buffer washes (20 mM sodium phosphate pH 7.0). Bound antibody proteins on the protein A column were recovered by acidic antibody elution from protein A (0.1 M glycine-HCl pH 3.0). Eluted proteins were immediately neutralized with 1M Tris-HCl pH 9.0 (100 mL per mL eluted fractions). Pooled eluted fractions were dialyzed against PBS. Aggregated antibody proteins were removed by size exclusion chromatography.

Formalin-Induced Licking Behavior in Mice.

The experiment was performed in two days sessions, between 9 and 16 hours, 8 animals/groups of treatment. On the day before the experiment, 16 mice were weighed and allocated 4 per cage; 20 µl of formalin solution (1% in saline) were subcutaneously injected into the plantar surface of the right hind paw using an Hamilton micro-syringe equipped with a 26-gauge needle; four animals at a time were placed in a transparent plexiglass box (11×12×12 cm), allowed to move freely, and the observation period started. A mirror was placed behind the boxes to allow an unimpeded view of the animals hind paws. The licking activity, i.e. the total amount of time the animal spent licking the injected paw, was taken as index of pain. The licking activity was recorded continuously for 1 hour, calculated in blocks of consecutive 5-minutes periods and analyzed as the early (0-5 min) and the late (15-35 min) phases of the formalin test. Each mouse was subcutaneously injected into the dorsal surface of the right hind paw using an Hamilton micro-syringe (26-gauge needle) with 20 µl anti-TrkA (5-20 mg/paw) mAb or PBS as control group, 18 hours before the test.

Alternatively, mice were subcutaneously injected (systemically) with 300 µl CRB0089_IgG4 (5-20 mg) or PBS as control group, 18 hours before the test.

CFA-Induced Inflammatory Pain in Rats.

Male Wistar rats were injected into the right hind footpad with 300 µg of *Mycobacterium tuberculosis* in 100 µL of liquid paraffin (Complete Freund's Adjuvant; CFA). Seventy-two hours later, CRB0089_IgG4 (5 or 20 µg) was administered subcutaneously and 18 h after the administration, the response to noxious mechanical stimulation was assessed by measuring paw withdrawal threshold (PWT) with an analgesimeter of the Randall-Selitto type. Animals were gently restrained, and steadily increasing pressure was applied to the dorsal surface of both the ipsilateral (CFA-treated) and the controlateral paw via a dome-shaped plastic tip.

To evaluate the paw edema induced by the CFA injury, CRB0089_IgG4 was administered in the right hind paw 72 hours later the CFA injection. Eighteen hours after CRB0089_IgG4 administration, the paw volume was measured by means of a Plethysmometer (UgoBasile, Italy).

Chronic Constriction Injury (CCI)—Induced Neuropathic Pain in Rats.

Experiments were performed on male Wistar rats (Charles River) weighing 225-250 g at the time of surgery. A minimum of 7 days was allowed for acclimatization before the beginning of the experiments. On each test day, the rats were brought into the experimental room 2 hours prior to the session in order to habituate them to the environment. The experiments were performed by a single experimenter. The CCI was carried out as described previously by Bennet and Xie (Bennett and Xie, 1988. *Pain.* 33:87-107). Rats were anesthetized with sodium pentobarbital (50 mg/kg i.p.). The common right sciatic nerve was exposed at mid-thigh level, proximal to the sciatic trifurcation. Four chronic gut ligatures (4/0 silk) with about 1 mm spacing were loosely tied around the nerve, so that the vascular supply was not compromised. The overlying muscle was closed in layers with 4/0 synthetic absorbable surgical suture. The skin was closed by application of acrylic glue. In sham animals, an identical dissection was performed, except that the sciatic nerve was not ligated. The tests were conducted on animals at least 1 week after surgery. The response to noxious mechanical stimulation was assessed by measuring PWT with an analgesimeter. Animals were gently restrained, and steadily increasing pressure was applied to the dorsal surface of the ipsilateral (CFA-treated) paw via a dome-shaped plastic tip. The latency to paw withdrawal was determined before surgery, after surgery and at a selected time after test compound or vehicle injection.

A Non-Inflammatory Model of Chronic Muscle Pain in Rats: Bilateral Allodynia Induced by Unilateral Injection of Acidic Saline in the Gastrocnemius Muscle.

The acidic saline animal model of pain is thought to mimic human chronic pain syndromes such as fibromyalgia. Repeated intramuscular injections of acidic saline is a model of non-inflammatory pain characterized by bilateral long-lasting allodynia of the paw which is believed to be centrally mediated.

Male Wistar rats were brought to the behavioral testing room 1 h before the test. The right gastrocnemius muscle was injected with 150 μL of preservative-free sterile saline (pH=4). Five days later (5 d), the same gastrocnemius muscle was re-injected. As a control for the injection procedure, a separate group of animals were injected with sterile saline. Ipsilateral and contralateral paw withdrawal thresholds in response to mechanical stimuli were measured on Days 0 (baseline—0 d), 5 (5 d), 6 (6 d), 9 (9 d), and 12 (12 d). Nociceptive thresholds, expressed in grams (g), were measured with a Dynamic Plantar Aesthesiometer by applying increasing pressure to the right and left hind paw until the rat withdrew the paw. A maximal cut-off of 50 g was used to prevent tissue damage. The threshold was tested three times for each paw and the mean value was calculated. On Day 5, 6 h after the second saline injection, CRB0089_IgG4 was administered subcutaneously at a dose of 20 μg/rat. A saline subcutaneous injection was used as vehicle control. Mechanical withdrawal thresholds of both hind paws were measured 18 h (6 d), 90 h (9 d), and 162 h (12 d) after CRB0089_IgG4 injection. Two injections of acidic saline into the gastrocnemius muscle produced bilateral decreases in the mechanical withdrawal threshold of the paw 24 h after the second injection.

Results

Selection of Specific Anti-VEMHHW Epitope of Human TrkAscFvs Using SPLINT Technology.

To select specific anti-VEMHHW epitope of human TrkA receptor by SPLINT technology, the VEMHHW peptide (SEQ ID NO: 66) was engineered to be part of the two loops of the immunoglobulin like (Ig-like) domain of 127 Titin protein (SEQ ID NOs: 68, 69). Ig-like domain is a common structural unit across many protein families that are functionally unrelated (Wright et al., 2004. *Protein Eng Des Sel.* 17:443-453. Epub 2004 June 2018). The beta-sandwich fold provides a very robust structural scaffold upon which it is possible to insert long peptides without altering either the structure or folding of the domain. VEMHHW peptide was inserted between A76-N77 and E27-D29 of 127 Ig-like domain of titin protein (SEQ ID NO: 92). The recombinant 2×VEMHHW-127 protein was subsequently cloned at the 3' of LexA and used to challenge a mouse SPLINT (mSPLINT) and a human SPLINT libraries (huSPLINT_09) (Visintin et al., 2004. *J Immunol Methods.* 290:135-153).

From the selection procedure using hSPLINT_09 a total of 189 colonies able to grow in the absence of histidine and showing activation of β-Galactosidase were obtained. The scFv-VP16 plasmids were isolated and sorted by their restriction patterns and sequences. The specificity of scFvs with different DNA fingerprints were re-analyzed using yeast strains expressing LexA-2×VEMHHW-127 and LexA-127, as non-relevant antigen. 61 different anti-VEMHHW scFvs were thus identified. Analysis of the V region nucleotide sequences of the selected anti-VEMHHW scFvs revealed that they were derived from germline V region genes. The amino acid sequence of V regions of the isolated anti-VEMHHW scFvs are in the group of sequences consisting of SEQ ID NO: 1, 2, 3, 4 from the selection of mSPLINT and SEQ ID NOs: 5, 6, 7, 8, 9, 10, 11, 12, 13, 14, 15 and 16 from the selection of hSPLINT 09.

Expression and Refolding of Anti-TrkA in the Cytoplasm of *E. Coli*

To identify potential anti-TrkA in vivo binders cDNA expressing anti-VEMHHW scFv were cloned into *E. coli* pETM-13 expression vector. The proteins were well expressed in the cytoplasm and mostly retained in inclusion bodies (IB). scFv fragments can be refolded by dialysis after solubilization of IB (Umetsu et al., 2003. *J Biol Chem.* 278: 8979-8987. Epub 2003 January 8977). We performed the technique of refolding by dilution (Patil et al., 2008. *J Biotechnol.* 134:218-221. Epub 2008 January 2018). The refolding condition of scFv was optimized for each sample. Refolded scFv were subsequently quantified by Bioanalyzer 2100 (Agilent) and tested by ELISA and Biacore analysis.

Binding Specificity and Cross-Reactivity of Anti-TrkA to Human and murineTrkA

Figure 2:
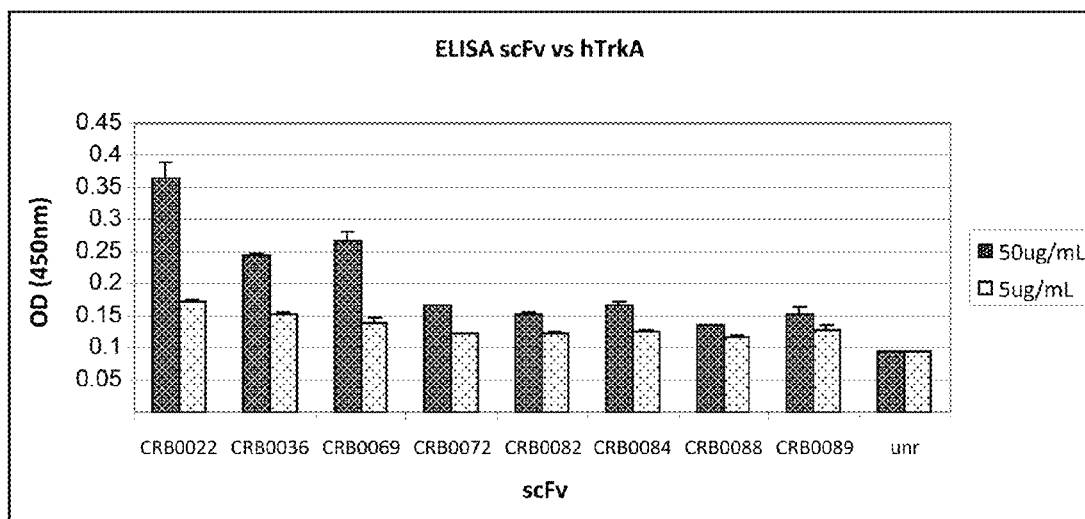
FIG. 2. ELISA reactivity of isolated anti-TrkA scFvs versus human TrkA immunoadhesin (hTrkA-Fc) and an unrelated scFv (unr) as negative control. hTrkA-Fc antigen was coated at 2 mg/mL. Anti-TrkA scFvs were used at 50 and/or 5 mg/mL. The mean absorbance at 450 nm of the experiments performed in duplicate wells is shown with SD indicated by the bars.
Figure 3:
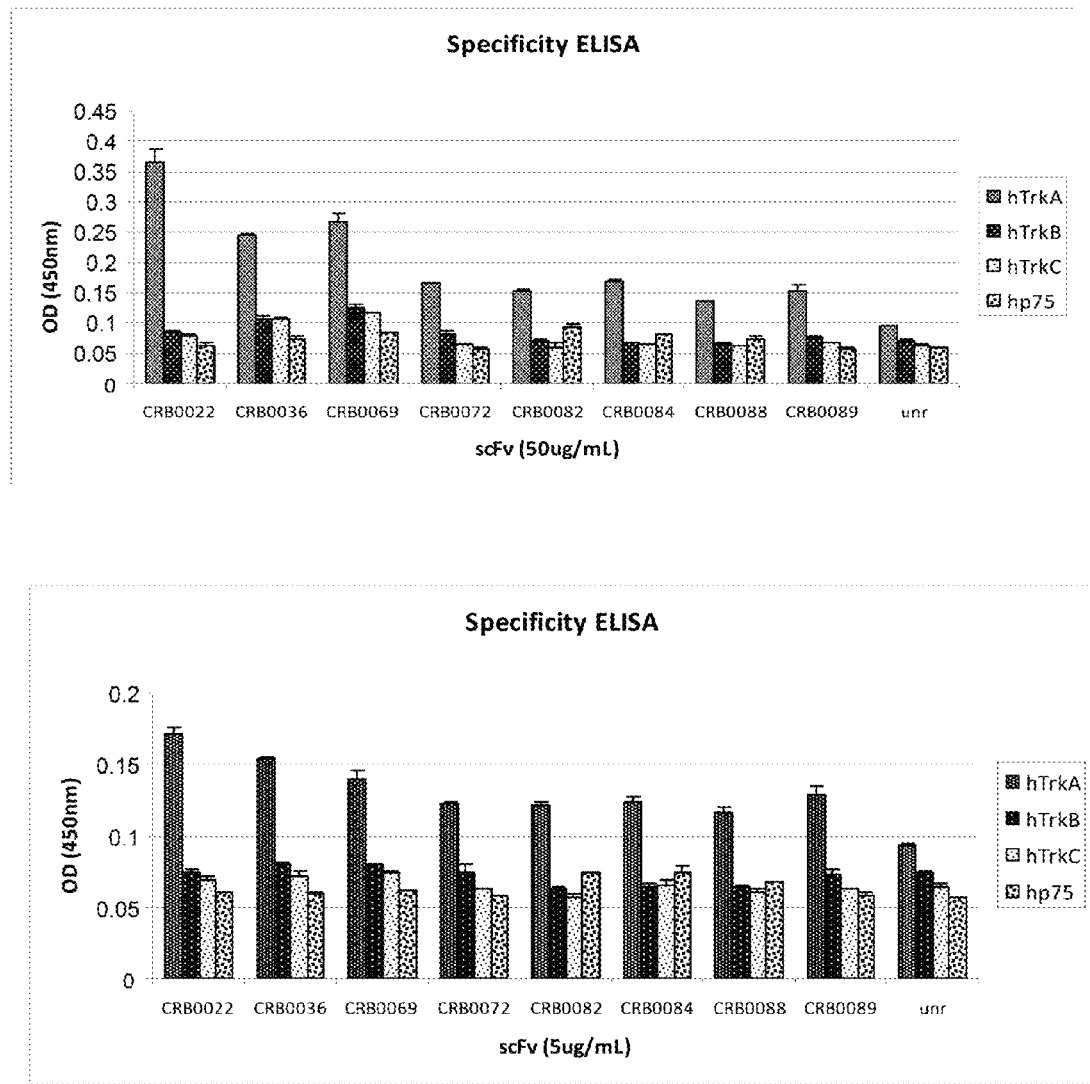
FIG. 3. Specificity ELISA of isolated anti-TrkA scFvs versus human TrkA immunoadhesin (hTrkA-Fc), human TrkB immunoadhesins (hTrkB-Fc), human TrkC immunoadhesins (hTrkC-Fc) and human p75 immunoadhesins (hp75-Fc). Human antigens were coated at 2 µg/mL. Anti-TrkA scFvs were used at 50 µg/mL (upper panel) and/or 5 µg/mL (lower panel). The mean absorbance at 450 nm of the experiments performed in duplicate wells is shown with SD indicated by the bars.
Figure 4:
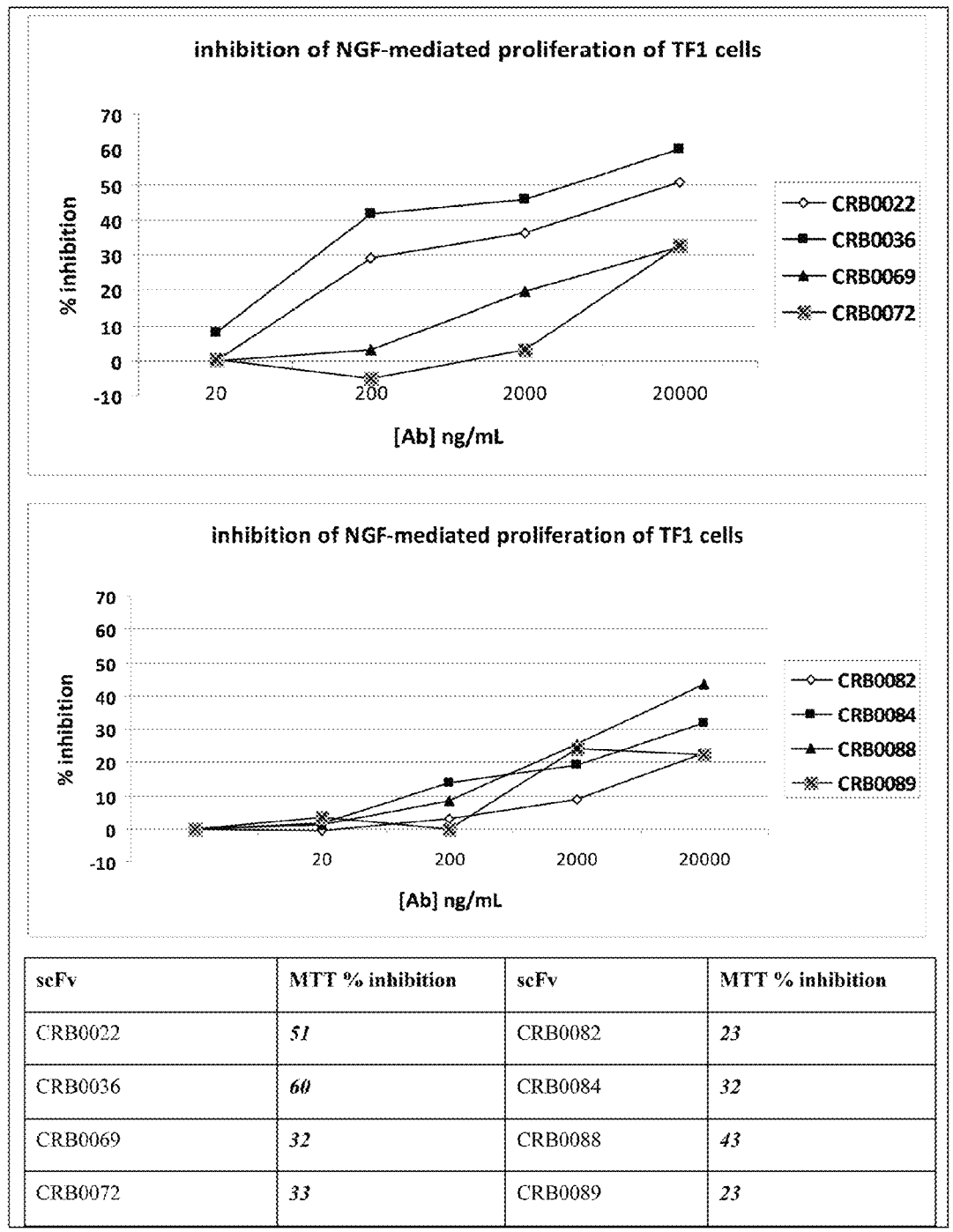
FIG. 4. MTT assay of isolated anti-TrkA scFvs. Cell proliferation in TF1 was measured following incubation with NGF and the indicated anti-TrkA scFvs. The MTT assay is a colorimetric assay for measuring the activity of enzymes that reduce MTT (3-(4,5-Dimethylthiazol-2-yl)-2,5-diphenyltetrazolium bromide, a yellow tetrazole) to formazan dyes, giving a purple color. It is apply in this experiment to assess the proliferation of TF1 cells. Cells were challenged with various concentrations of scFv (20 ng/mL; 200 ng/mL; 2,000 ng/mL and 20,000 ng/mL). % of inhibition of TF1 proliferation was calculated using 10 ng/ml as 100% standard. All anti-TrkA scFvs inhibit NGF-mediated proliferation in a dose-dependent manner.

The purified anti-TrkA scFv were first analysed by FACS analysis for binding to TrkA receptor. TrkA binding analysis by flow cytometry on 3T3-TrkA and TF1 expressing TrkA receptor was performed with the panel of isolated anti-TrkA scFvs. All the anti-TrkA scFvs were able to recognize the TrkA receptor under physiological condition. Following identification of TrkA expressing cells by anti-TrkA scFv, we analyzed the panel of scFv for specificity and crossreactivity with mouse TrkA by ELISA assay. In order to use the extracellular domain (ECD) of Trk receptor we have engineered a panel of human Trk receptors (TrkA, TrkB, TrkC and p75NTR) as immunoadhesin proteins. These recombinant proteins were constructed to have the ECD domain of the Trk receptors linked to the Fc portion of a IgG2a camel antibody (*Camelus dromedaries*) (SEQ ID NOs: 70, 71, 72, 73 and 74). The recombinant protein were expressed in mammalian cell line (CHO-S cell line) and purified by protein A column. After purification the receptor chimera were analysed by SDS-PAGE western blot analysis under reducing condition (FIG. 7). The purified immunoadhesins were used as ligand in ELISA. As shown in FIG. 2, all the scFv were able to recognize at the concentration of 50 μg/mL and 5 μg/mL the TrkA immunoadhesins. The same scFvs were tested against the Trk family immunoadhesins. The anti-TrkA seems to be specific for TrkA only, even if a slight crossreactivity was shown for some scFv (CRB0036 and CRB0069) on TrkB and TrkC immunoadhesins (FIG. 3).

Like other receptor tyrosine kinases, TrkA undergoes dimerization and activation upon ligand binding. In the absence of NGF, some domains of the receptor, perhaps the same ones responsible for ligand binding, impede its spontaneous dimerization at the cell surface (Arevalo et al., 2000. *Mol Cell Biol.* 20:5908-5916). It was demonstrated that a recombinant deleted protein of TrkA receptor, Ig-1,2 which express both Ig-1 and Ig-2 domains of the extracellular domain (ECD) of the receptor TrkA was able to dimerize also in the absence of NGF (Arevalo et al., 2000. *Mol Cell Biol.* 20:5908-5916.). We have used two recombinant proteins engineered to express both Ig-likes domains and able to dimerize in the absence of NGF for Biacore analysis.

We have carried out surface plasmon resonance (SPR) analyses to determine the binding kinetics of a panel of isolated anti-TrkA scFvs (SEQ ID NOs: 1, 2, 3, 4, 5, 6, 7, 8, 9, 10, 11, 12, 13, 14, 15 and 16). The scFvs were immobilized on a CM5 chip followed by injections at various concentration of human and murine Ig 1,2 TrkA (SEQ ID NO: 78) and mouse Ig1,2 TrkA (SEQ ID NO: 79). As shown in Table II and III, all the scFvs were able to recognize both human and mouse Ig 1,2 recombinant TrkA proteins in the range of nanomolar affinity.

Measurement of Antagonism of NGF Activity of Anti-TrkA scFvs.

Figure 5:
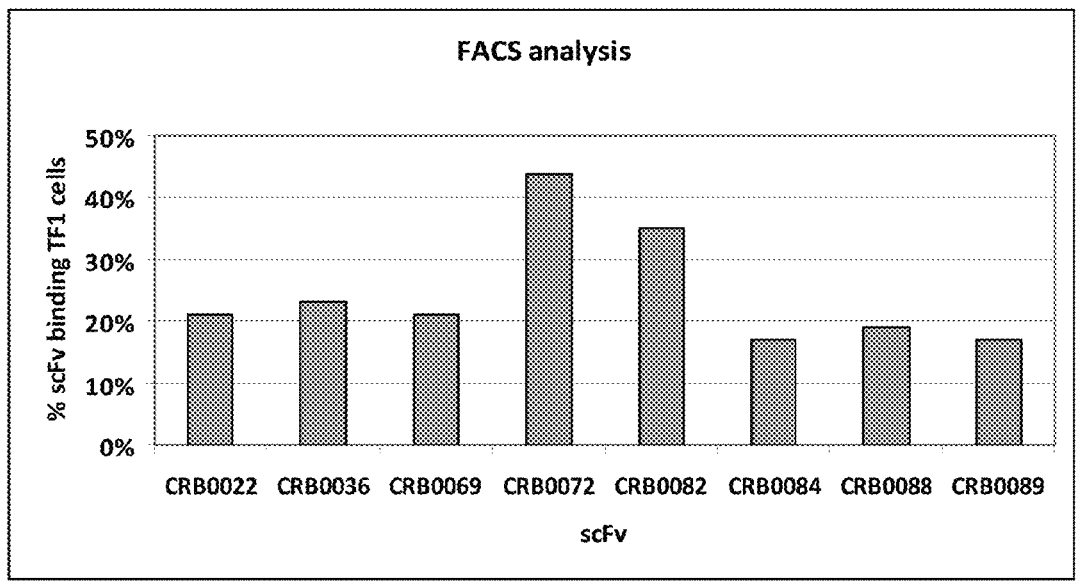
FIG. 5. FACS analysis performed with Bioanalyzer 2100. A cell fluid chip-based fluorescent cytometric assay that runs on Bioanalyzer 2100 (Agilent) for fast characterization of small population cell phenotypes was assessed. The assay determines the expression of specific cell surface markers. In this experiment, the specificity of scFvs on TF-1 cell line expressing human TrkA receptor was assessed. Six samples can be analyzed on each chip in one automated process. Results were in good agreement with conventional flow cytometry in quantisation.

In order to evaluate the potency of anti-TrkA scFvs, the TF1 cell proliferation assay (MTT cell proliferation kit, ATCC) was used (concentration/response study). Final average OD values for triplicate measurements were calculated by subtraction of the average values for the cellular blank. Maximal inhibition was set corresponding to the average OD value observed for cells cultured without NGF, in the absence of test antibody. Zero inhibition was set corresponding to the average OD value observed for cells exposed to 10 ng/ml NGF in the absence of test scFv. As shown in FIG. 5, all the isolated anti-TrkA scFv were able to inhibit TF1 cell proliferation mediated by human NGF in a range between 20-60%.

Figure 8:
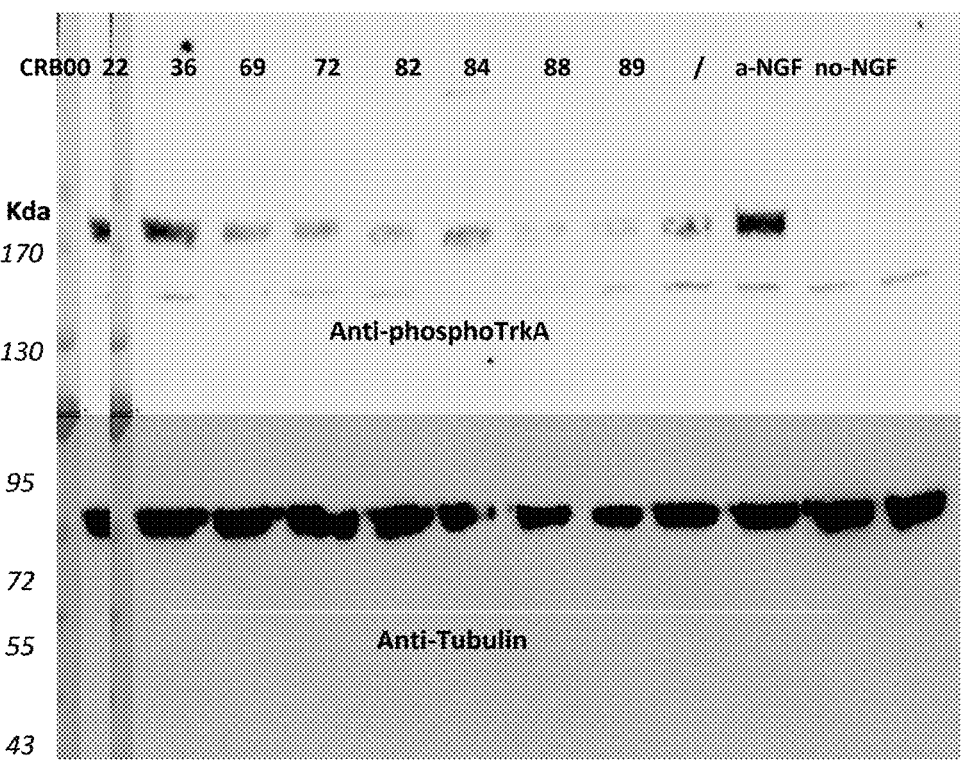
FIG. 8. NGF biological assay performed with 3T3TrkA cells. Western blot results showing that CRB0022, CRB0036, CRB0069, CRB0072, CRB0082, CRB0084, CRB0088 and CRB0089 lead a differential reduction of phospho-TrkA levels after NGF stimulation in mouse 3T3 cells overexpressing TrkA.

To test whether the anti-TrkA scFvs were also able to inhibit NGF triggered phosphorylation on Tyr residues under physiological condition in 3T3TrkA cell line, we treated the cell line with NGF and 100 mg/mL anti-TrkA for 1 hour. As shown in FIG. 8 all the scFv tested were able to inhibit the phosphorylation of TrkA at Tyr 490. As a positive control, a strong antagonist of NGF that totally inhibit the phosphorylation of TrkA was used (anti-NGF).

Figure 6:
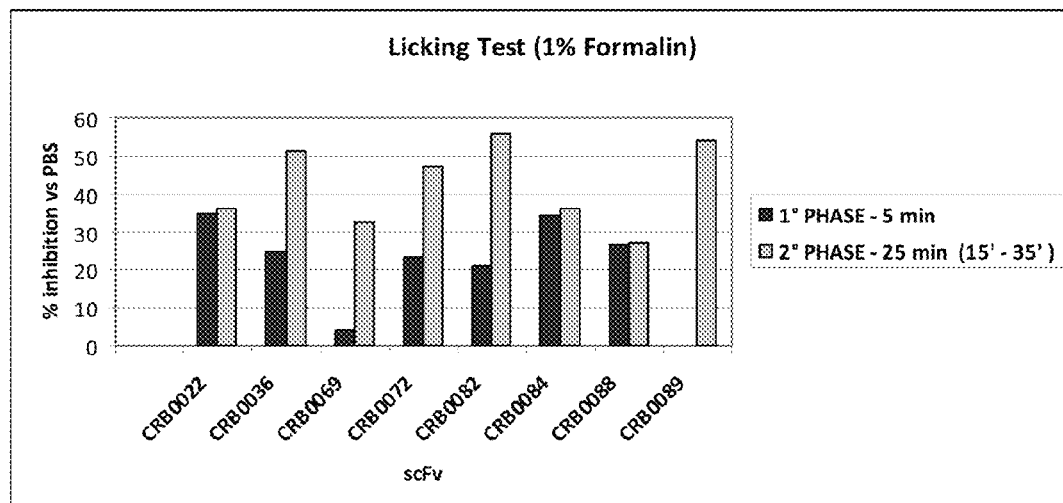
FIG. 6. Evaluation of analgesic activity in the formalin test in the mouse. The licking activity was recorded continuously for 1 hour, calculated in blocks of consecutive 5-minutes periods and analyzed as the early (0-5 min) and the late (15-35 min) phases of the formalin test. Each mouse was subcutaneus injected into the dorsal surface of the right hind paw one hour before the test with 20 µl (40 µg) anti-TrkA scFv or PBS as control groups. The two phases characterizing the formalin test were separately analyzed by unpaired Student's t test (for two groups).

To test whether the anti-TrkA scFvs were able to inhibit inflammatory pain induced by subcutaneous injection of formalin in mouse model, 20 mg of each purified anti-TrkA scFv was injected subcutaneously in the mouse hind paw. The injection resulted in a biphasic licking response: the first phase represents a basic pain response to direct stimulation of the nerve endings, the second phase represents a tonic pain response to subsequent inflammation. The effect of different anti-TrkA scFv is summarized in FIG. 6. All anti-TrkA scFv were able to inhibit the second phase of formalin induced pain with a percent of analgesic effect in a range between 27-55%.

mAb CRB0089_IgG4: Biochemical Characterization of the Reformatted Immunoglobulin A complete IgG4 immunoglobulin was assembled by amplifying the individual V-regions of isolated anti-TrkA CRB0089 into a vector enabling the transfer of V-regions from scFv to full length immunoglobulin for mammalian expression.

Figure 9:
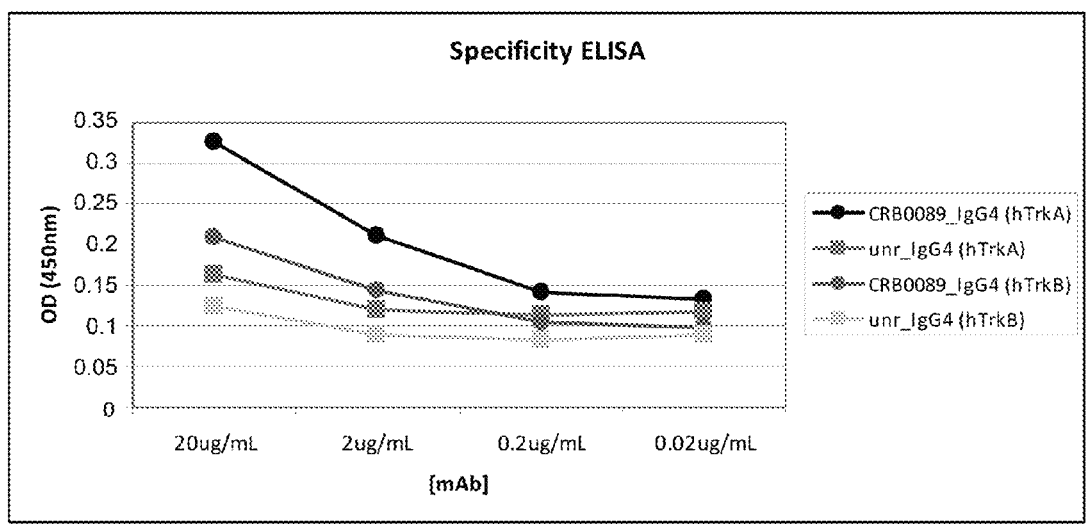
FIG. 9. Specificity ELISA of anti-TrkA CRB0089_IgG4 mAb versus human TrkA immunoadhesin (hTrkA-Fc) and human TrkB immunoadhesins (hTrkB-Fc), Human antigens were coated at 2 µg/mL. CRB0089_IgG4 was used at different concentration (20 µg/mL-0.02 µg/mL). The mean absorbance at 450 nm of the experiments performed in duplicate wells is shown with SD indicated by the bars. CRB0089_IgG4 binds hTrkA-Fc in a dose-dependent manner. A minimal binding activity was shown also for hTrkB-Fc but only at higher doses.

Whole IgG4 was produced and purified from transfected CHO cell line. The anti-TrkA CRB0089_IgG4 was tested for binding in ELISA. As shown in FIG. 9, the antibody was able to bind in a dose specific way TrkA receptor. A weak interaction with TrkB receptor was also detected even if the specificity of this binding must be confirmed by other specific binding assay.

Furthermore, the kinetic analysis of CRB0089 IgG4 to TrkA Ig1,2 on Biacore X-100 was performed. As shown in Table IV, the kinetics rates of association and dissociation and affinity constants were calculated both for human and murine TrkA receptor. mAb CRB0089_IgG4 cross reacts with similar affinity both human and murine receptor thus indicated that murine models of pain can be used for further preclinical development of the antibody.

Figure 10:
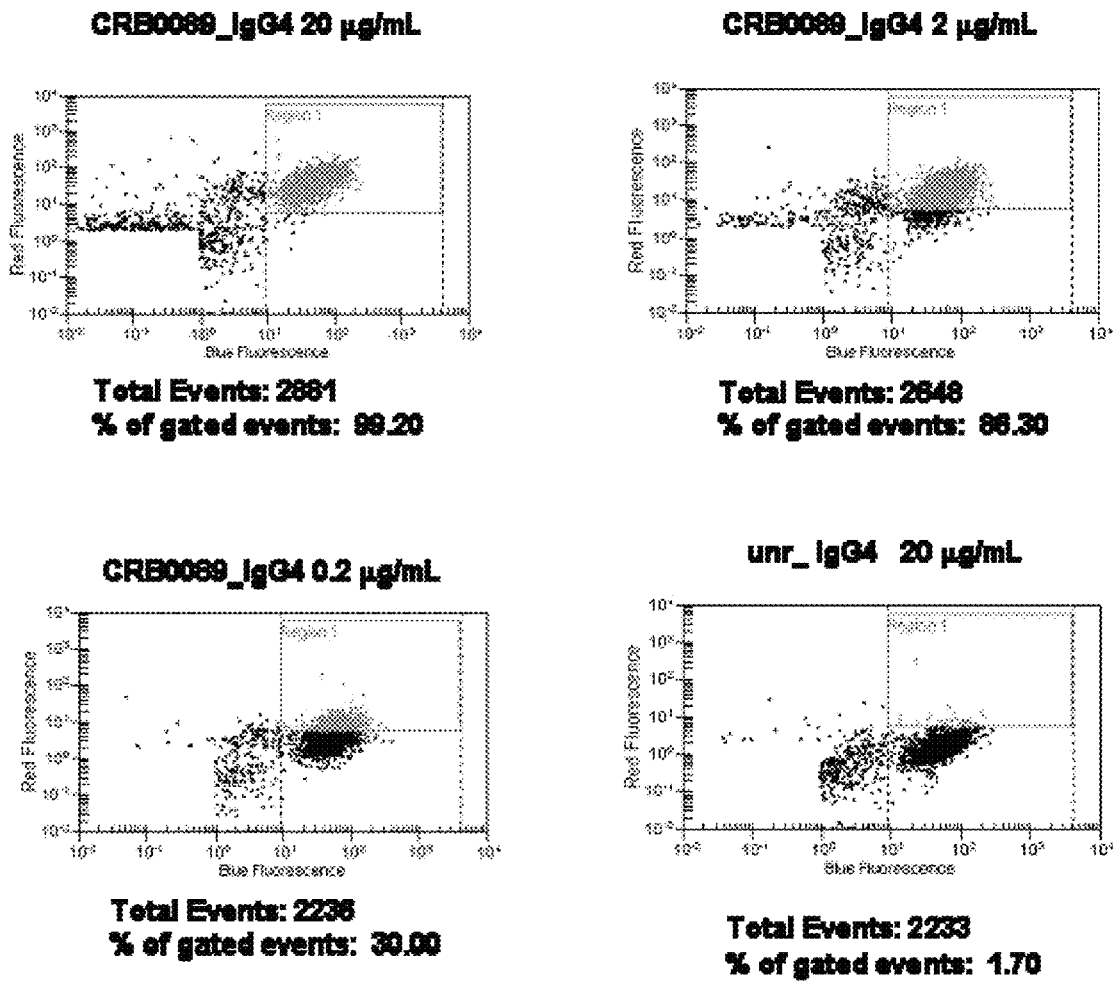
FIG. 10. FACS analysis performed with Bioanalyzer 2100. A cell fluid chip-based fluorescent cytometric assay that runs on Bioanalyzer 2100 (Agilent) for fast characterization of small population cell phenotypes was assessed. In this experiment, the specificity of anti-TrkA CRB0089_IgG4 on TF-1 cell line expressing human TrkA receptor was assessed. Results were in good agreement with conventional flow cytometry in quantisation.

Mab CRB0089_IgG4 was also tested to bind TF1 expressing TrkA receptor by FACS analysis. The antibody was able to bind to TrkA receptor in a dose dependent manner. At higher concentration (20 mg/mL) the antibody display 99% gated events on more than 2800 cells tested. The antibody strongly bind to TrkA receptor even at lower concentrations (FIG. 10) as compared with an unrelated antibody (unr-IgG4) used as negative control.

Measurement of Anti-TrkA Antagonism Activity of CRB0089_IgG4.

In order to evaluate the potency of anti-TrkA CRB0089_IgG4, a TF1 cell proliferation assay was employed (concentration response study). The inhibitory potency of anti-TrkA CRB0089_IgG4 antibody was quantified as $IC_{50}$ values (i.e., the concentration of antibody required to reduce the NGF-mediated proliferative response by 50%) using Sigma Plot software. Inhibition curves were plotted individually in order to obtain discrete $IC_{50}$ values for each test antibody in each experiment. Measures of cell proliferation were normalized with respect to maximum OD values obtained within that assay, in the absence of added test antibody. Normalized responses were then plotted against test antibody concentration on a log scale, and $IC_{50}$ values were derived using the Sigma Plot nonlinear curve fitting function "log(inhibitor) vs response-variable slope".

Figure 11:
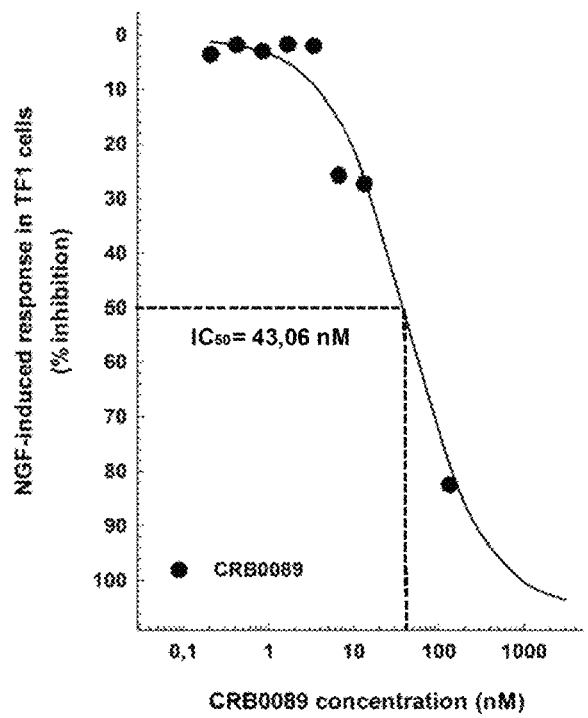
FIG. 11. Dose response curve with IC50 determination. MTT potency assay was used for the determination of potency of CRB0089_IgG4. Cell proliferation of TF1 cells was measured following incubation with NGF and the indicated concentration of CRB0089_IgG4. CRB0089_IgG4 inhibited NGF-mediated proliferation in a dose-dependent manner. Half-maximal inhibition (IC50) by CRB0089 IgG4 was calculated around 40 nM.

As shown in FIG. 11, CRB0089_IgG4 was able to inhibit NGF-mediated proliferative response in a dose dependent manner with an $IC_{50}$ of approximately 43 nM.

In Vivo Activity of CRB0089_IgG4 in Inhibiting NGF-Mediated Pain

A series of in vivo experiments were conducted to assess the activity of CRB0089_IgG4 in rodent models of inflammatory/neurogenic and neuropathic pain.

Figure 12:
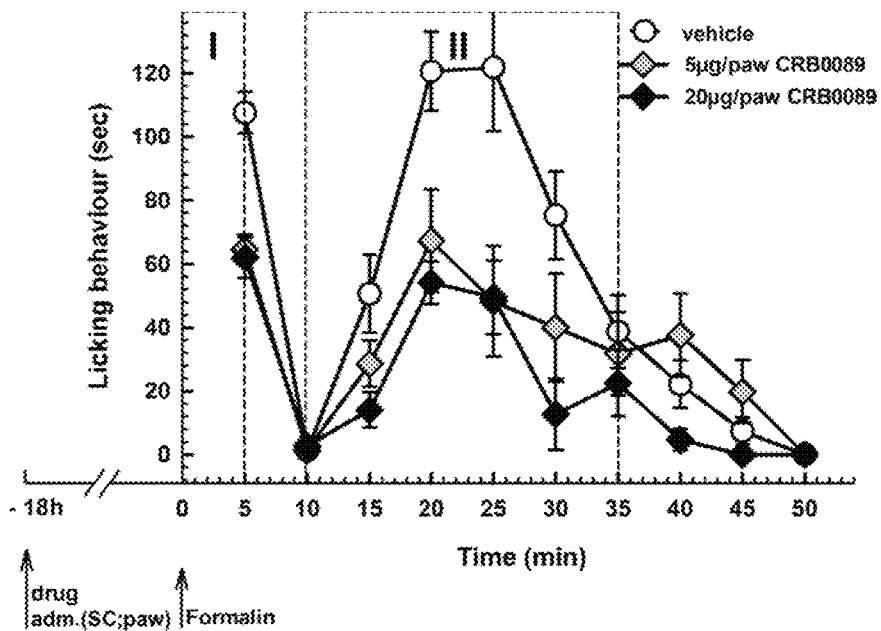
FIG. 12. Formalin-induced licking behavior in mice: effect of increasing doses of CRB0089_IgG4 injected locally in the right dorsal paw. Each mouse was subcutaneus injected with CRB0089_IgG4 at the indicated doses (5-20 µg of mAb) into the dorsal surface of the right hind paw eighteen hours before formalin injection (1% formalin). The licking activity was recorded continuously for 1 hour, calculated in blocks of consecutive 5-minutes periods and analyzed as the early (0-5 min) and the late (15-35 min) phases of the formalin test. The two phases characterizing the formalin test were separately analyzed by unpaired Student's t test (for two groups).

Two "classical" screening models were initially used to evaluate the analgesic properties of CRB0089_IgG4: a) the formalin-induced licking behavior in the mouse, b) the complete Freund's adjuvant (CFA)-induced mechanical hyperalgesia in the rat.

a) The experiment was performed in two days sessions with 8 animals/groups of treatment. CRB0089_IgG4, injected into the dorsal surface of the paw, showed to be active at both used dose (5-20 µg/paw) to inhibit both the early and the late phase of the formalin-induced behavior in mice (FIG. 12). In another experiment, each mouse was subcutaneously injected with 300 µl CRB0089_IgG4 or PBS as control group, 18 hours before the test. As internal control of the experiment, a group of mice (n=8) was treated locally in the right dorsal paw with 20 µg (1 µg/µl) CRB0089_IgG4 as in the previous experiment.

Figure 13:
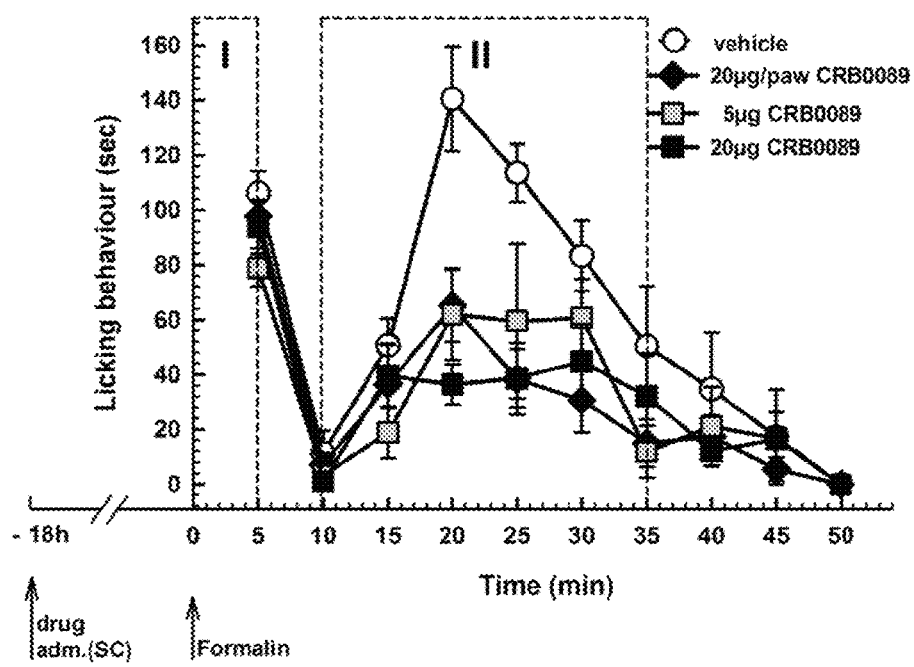
FIG. 13. Formalin-induced licking behavior in mice: effect of increasing doses of CRB0089_IgG4 subcutaneously injected. Each mouse was subcutaneously injected (systemically) with 300 µl CRB0089_IgG4 or PBS as control group, 18 hours before the test. As internal control of the experiment, a group of mice (n=8) was treated locally in the right dorsal paw with 20 µg (1 µg/µl) CRB0089_IgG4 as in the previous experiment shown in FIG. 11.

CRB0089_IgG4, injected s.c. in the range 5-20 µg, showed to inhibit the late phase of the formalin-induced behavior in mice at both the used doses (FIG. 13). No treatments induced significant changes related to the early phase of the formalin-induced behavior in mice.

b) Male Wistar rats were injected into the right hind footpad with *Mycobacterium tuberculosis* in liquid paraffin (Complete Freund's Adjuvant; CFA). Seventy-two hours later, CRB0089_IgG4 (5 or 20 µg) was administered subcutaneously and 18 h after the administration, the response to noxious mechanical stimulation was assessed by measuring PWT with an analgesimeter of the Randall-Selitto type. Animals were gently restrained, and steadily increasing pressure was applied to the dorsal surface of both the ipsilateral (CFA-treated) and the controlateral paw via a dome-shaped plastic tip.

Figure 14:
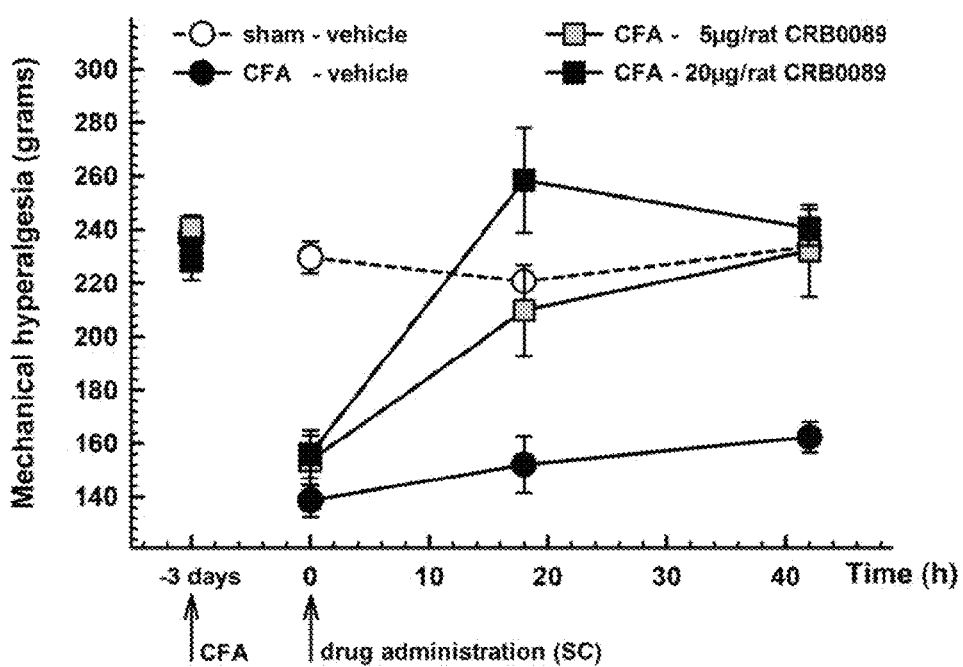
FIG. 14. CFA-induced inflammatory pain in rats: effect of increasing subcutaneous doses of CRB0089_IgG4. Male Wistar rats were injected into the right hind footpad with 300 µg of *Mycobacterium tuberculosis* in 100 µL of liquid paraffin (Complete Freund's Adjuvant; CFA). Seventy-two hours later, CRB0089_IgG4 (5 or 20 µg) was administered subcutaneously and 18 h after the administration, the response to noxious mechanical stimulation was assessed by measuring PWT with an analgesimeter of the Randall-Selitto type.
Figure 15:
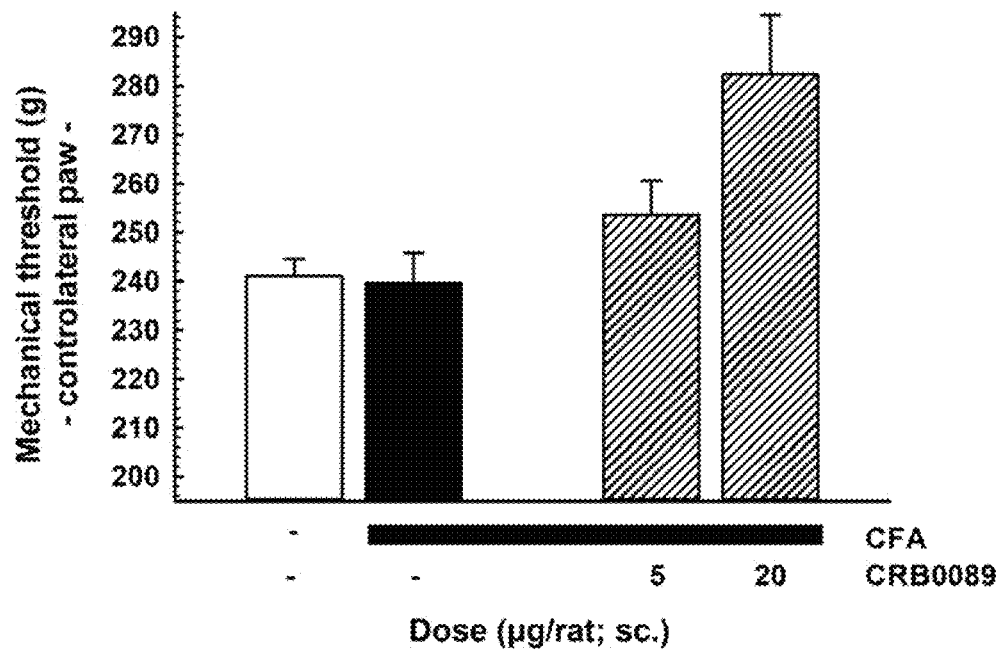
FIG. 15. CFA-induced inflammatory pain in rats: effect of increasing subcutaneous doses of CRB0089_IgG4 in the controlateral paw 18 h after injection. The response to noxious mechanical stimulation mechanical threshold was measured also in the controlateral non-injured hind paw. A slight but significant hypoalgesic-like effect was recognized after treatment with 20 µg/rat dose of CRB0089_IgG4.

In this experimental model of inflammatory pain, CRB0089_IgG4 dose-dependently reduced mechanical hyperalgesia in the CFA-injured hind paw 18 h after the antibody injection ($ED_{50}$=~5 µg/rat, $ED_{100}$=~20 µg/rat; FIG. 14). When the mechanical threshold was measured in the controlateral non-injured hind paw, a slight but significant hypoalgesic-like effect was recognized after treatment with 20 µg/rat dose of CRB0089_IgG4 (FIG. 15).

Figure 16:
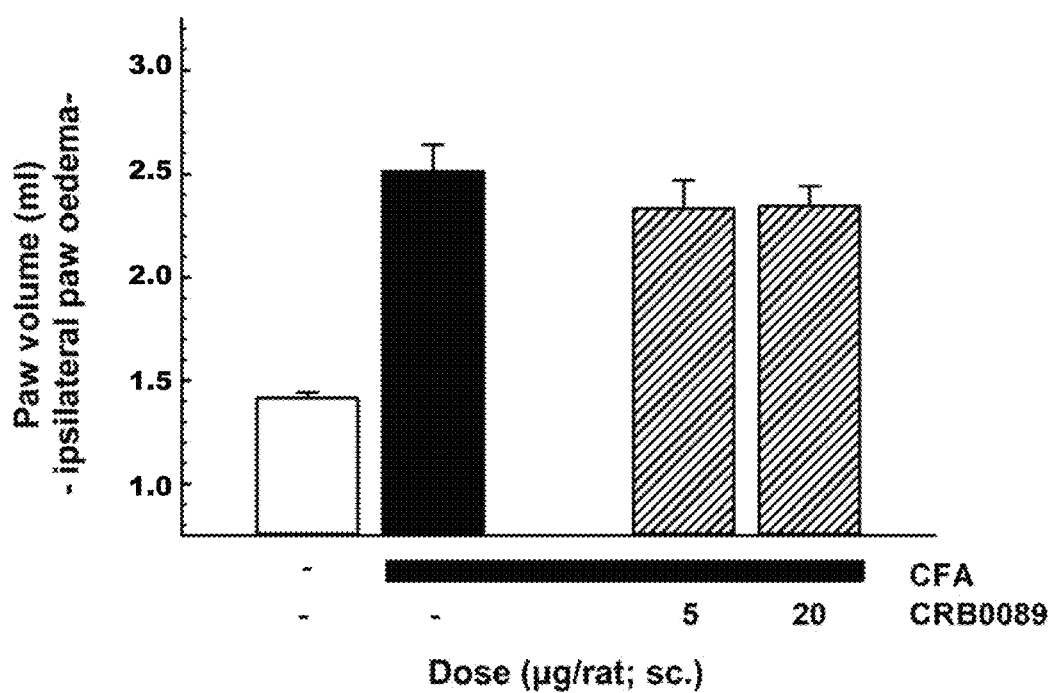
FIG. 16. CFA-induced paw edema in rats: effect of increasing subcutaneous doses of CRB0089_IgG4 in the ipsilateral paw 18 h after injection. The paw edema induced by the CFA injury in the right hind paw was evaluated. As for the hyperalgesic test, CRB0089_IgG4 was administered 72 h after the CFA injection. Eighteen hours after CRB0089_IgG4 administration the paw volume was measured by means of a Plethysmometer (UgoBasile, Italy).

In this experiment it was also evaluated the paw edema induced by the CFA injury in the right hind paw. As for the hyperalgesic test previous described, we administered CRB0089_IgG4 72 h later the CFA injection. Eighteen hours after CRB0089_IgG4 administration the paw volume was measured by means of a Plethysmometer. As shown in FIG. 16, both concentrations of CRB0089_IgG4 did not reduced paw edema in treated rats.

Figure 17:
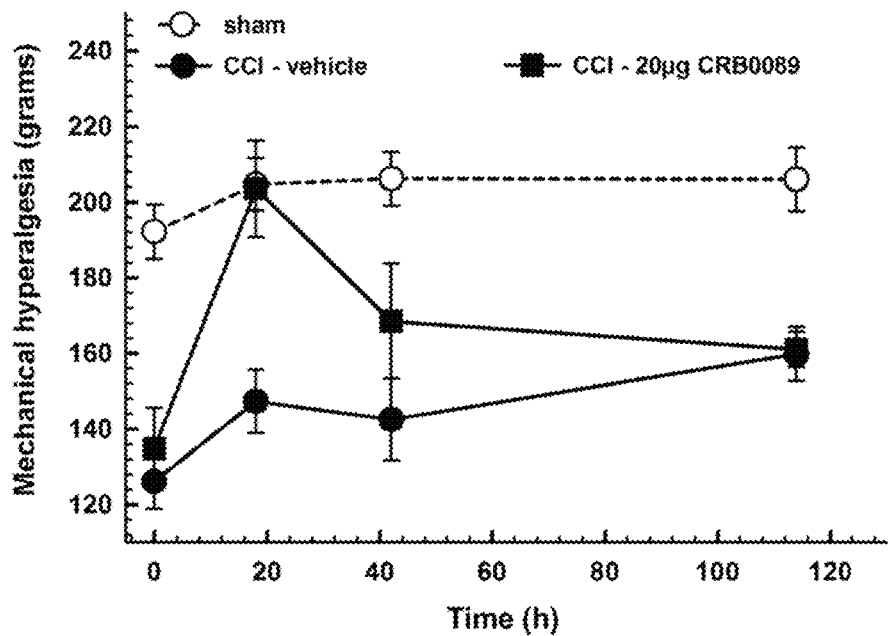
FIG. 17. CCI-induced neuropathic pain in rats: effect of a single injection of 20 µg/rat CRB0089_IgG4 on mechanical hyperalgesia. Experiments were performed on male Wistar rats. The response to noxious mechanical stimulation was assessed by measuring PWT with an analgesimeter.
Figure 18:
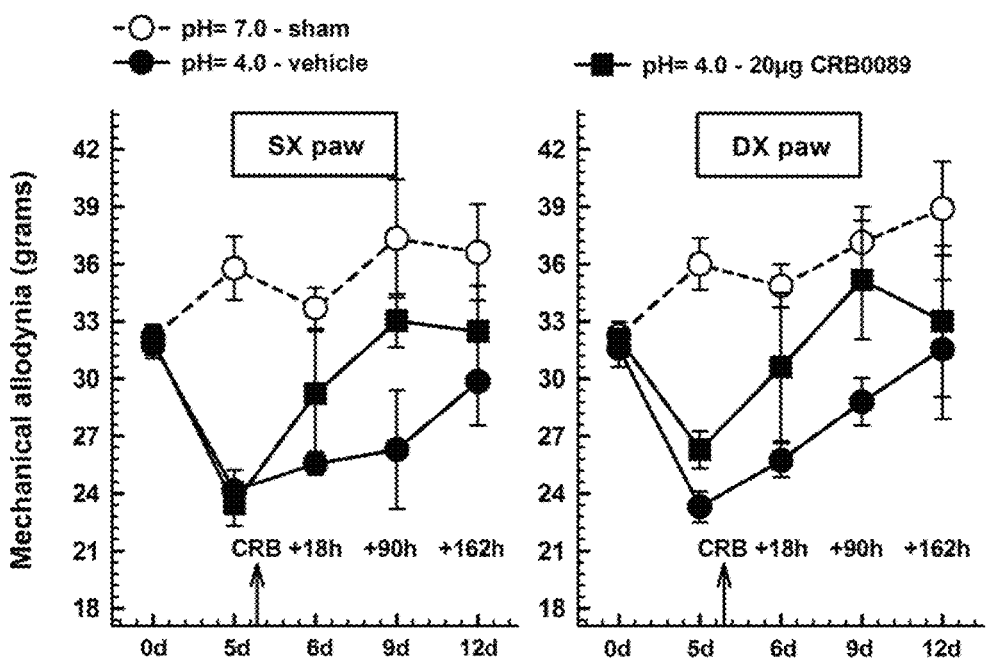
FIG. 18. Acidic saline-induced pain in rats: effect of a single injection of 20 µg/rat CRB0089_IgG4 on mechanical allodynia. Ipsilateral and contralateral paw withdrawal thresholds in response to mechanical stimuli were measured on Days 0 (baseline—0 d), 5 (5 d), 6 (6 d), 9 (9 d), and 12 (12 d). Nociceptive thresholds, expressed in grams (g), were measured with a Dynamic Plantar Aesthesiometer by applying increasing pressure to the right and left hind paw until the rat withdrew the paw.

To test neuropatic pain, two different animal models were used: c) chronic constriction injury (CCI)-induced neuropathic pain in rats and d) a non-inflammatory model of chronic muscle pain in rats-bilateral allodynia induced by unilateral injection of acidic saline in the gastrocnemius muscle.

c) Experiments were performed on male Wistar rats (Charles River) weighing 225-250 g at the time of surgery. The CCI was carried out as described previously (Bennett and Xie, 1988. *Pain*. 33:87-107). The tests were conducted on animals at least 1 week after surgery. The response to noxious mechanical stimulation was assessed by measuring PWT with an analgesimeter. Animals were gently restrained, and steadily increasing pressure was applied to the dorsal surface of the ipsilateral (CFA-treated) paw via a dome-shaped plastic tip. The latency to paw withdrawal was determined before surgery, after surgery and at a selected time after test compound or vehicle injection. As shown in FIG. 17, CRB0089_IgG4 at the concentration of 20 mg/rat induced 100% reversion of hyperalgesia after 18 h post injection.

d) The acidic saline animal model of pain is thought to mimic human chronic pain syndromes such as fibromyalgia. Repeated intramuscular injections of acidic saline is a model of non-inflammatory pain characterized by bilateral long-lasting allodynia of the paw which is believed to be centrally mediated. Ipsilateral and contralateral paw withdrawal thresholds in response to mechanical stimuli were measured on Days 0 (baseline—0 d), 5 (5 d), 6 (6 d), 9 (9 d), and 12 (12 d). Nociceptive thresholds, expressed in grams (g), were measured with a Dynamic Plantar Aesthesiometer by applying increasing pressure to the right and left hind paw until the rat withdrew the paw. CRB0089_IgG4 was administered subcutaneously at a dose of 20 µg/rat 6 h after the second acidic saline injection. Mechanical withdrawal thresholds of both hind paws were measured 18 h (6 d), 90 h (9 d), and 162 h (12 d) after CRB0089_IgG4 injection. Two injections of acidic saline into the gastrocnemius muscle produced bilateral decreases in the mechanical withdrawal threshold of the paw 24 h after the second injection. CRB0089_IgG4 (20 µg/rat), injected subcutaneously 18 h before the measure of mechanical allodynia (6 d), increased the withdrawal threshold of both hind paws. The anti-nociceptive effects of a single injection of 20 µg/rat CRB0089_IgG4 lasted almost 90 h before returning to basal allodynic parameters. As shown in FIG. 18 CRB0089_IgG4 at the concentration of 20 µg/rat induced 100% reversion of hyperalgesia after 90 h of injection in the ipsilateral paw. Moreover, at the same concentration and at the same time, CRB0089_IgG4 induced 60% reversion hyperalgesia also in the controlateral paw.

Tables

TABLE I

Results of anti-TrkA SPLINT screening:

| BAIT | N. ≠clones (I screening) | N. positive clones (II screening) |
|---|---|---|
| TrkA_loopA | 189 | 61 |

TABLE II

Biacore analysis of anti-TrkA scFvs vs human TrkA: Human Ig1, 2 TrkA

| scFv | ka (1/Ms) | kd (1/s) | KD (M) |
|---|---|---|---|
| CRB0022 | 9192 | 2.94E−05 | 3.2 nM |
| CRB0036 | 2731 | 3.75E−05 | 13.7 nM |
| CRB0069 | 6266 | 3.57E−05 | 5.7 nM |
| CRB0072 | 3675 | 7.48E−06 | 2.04 nM |
| CRB0082 | 2090 | 8.79.E−05 | 42.1 nM |
| CRB0084 | 9602 | 1.63E−02 | 1.70 µM |
| CRB0088 | 2755 | 3.2E−06 | 1.16 nM |
| CRB0089 | 4598 | 7.76E−05 | 16.9 nM |

TABLE III

Biacore analysis of anti-TrkA scFvs vs mouse TrkA: Mouse Ig1, 2 TrkA

| scFv | ka (1/Ms) | kd (1/s) | KD (M) |
|---|---|---|---|
| CRB0022 | 9426 | 1.09E−05 | 1.16 nM |
| CRB0036 | 6440 | 7.07E−06 | 1.10 nM |
| CRB0069 | 6120 | 1.02E−05 | 1.67 nM |
| CRB0072 | 2907 | 4.93E−05 | 17 nM |
| CRB0082 | 2630 | 344.E−04 | 131 nM |
| CRB0084 | 1.07E+04 | 2.33E−05 | 2.18 nM |
| CRB0088 | 3413 | 1.31E−04 | 38.5 nM |
| CRB0089 | 2247 | 3.19E−05 | 14.2 nM |

TABLE IV

| Biacore analysis of CRB0089_IgG4: | | | |
|---|---|---|---|
| mAb | ka (1/Ms) | kd (1/s) | KD (M) |
| Human Ig1, 2 TrkA | | | |
| CRB0089_IgG4 | 6424 | 1.03E−04 | 1.61E−08 |
| Mouse Ig1, 2 TrkA | | | |
| CRB0089_IgG4 | 4950 | 1.36E−04 | 2.76E−08 |

TABLE V

TrkA_bait PCR assembly primers:

SEQ ID NO

I PCR-assembly 80 5'-CATCATGAATTCCTAATAGAAGTGGAAAAGCCTCTGTACGGAGTAGAGGTG-3'
81 5'-CACAGAAAGTTCAATTTCAAAGTGGGCTGTTTCACCAACAAACACCTCTACTCCGTACAGAGG-3'
82 5'-CCACTTTGAAATTGAACTTTCTGTGGAGATGCACCACTGGGTTCACGGCCAGTGGAAGCTG-3'
83 5'-CAATGATTTCACAGTCAGGGGAAGCTGTCAAAGGCTGTCCTTTCAGCTTCCACTGGCCGT-3'
84 5'-CTTCCCCTGACTGTGAAATCATTGAGGATGGAAAGAAGCATATTCTGATCCTTCATAACTGTCAGC-3'
85 5'-TCTCCACCTGGAAGGAAACCTCTCCTGTCATACCCAGCTGACAGTTATGAAGGATCAGAATAT-3'
86 5'-GGTTTCCTTCCAGGTGGAGATGCACCACTGGAAATCTGCAGCCAATCTGAAAGTGAAAGAATT-3'
87 5'-TAATACGACTCACTATAGTCGACGGATCCTTACAATTCTTTCACTTTCAGATTGGCTG-3'

II PCR-assembly 88 5'-CATCATGAATTCCTAATAGAAGTGGAAAAG-3'
89 5'-TAATACGACTCACTATAGTCGACGG-3'

---

The invention claimed is:

1. An antibody, recombinant or synthetic antigen-binding fragments thereof, comprising a heavy chain variable region comprising SEQ ID NO: 15 and a light chain variable region comprising SEQ ID NO: 16.

2. The antibody, recombinant or synthetic antigen-binding fragments thereof according to claim 1, which is an NGF antagonist.

3. A pharmaceutical composition comprising at least one antibody, recombinant or synthetic antigen-binding fragments thereof according to claim 1, and pharmaceutically acceptable excipients.

4. A method of inhibiting TrkA in a subject in need thereof, comprising administering an effective amount of at least one of an antibody, recombinant or synthetic antigen-binding fragments thereof according to claim 1.

5. The antibody according to claim 1.

* * * * *

SEQUENCE LISTING

<160> NUMBER OF SEQ ID NOS: 102

<210> SEQ ID NO 1
<211> LENGTH: 120
<212> TYPE: PRT
<213> ORGANISM: Artificial Sequence
<220> FEATURE:
<223> OTHER INFORMATION: CRB0022VH

<400> SEQUENCE: 1

Gln Val Gln Leu Gln Gln Ser Gly Ala Glu Leu Val Lys Pro Gly Ala
1               5                   10                  15

Ser Val Glu Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Gly Ile Asp Pro Ala Asn Gly Asn Thr Ile Tyr Val Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Gly Tyr Asp Phe Asp Tyr Ala Met Asp Tyr Trp Gly Gln
            100                 105                 110

Gly Thr Ser Val Thr Val Ser Ser
        115                 120

```
<210> SEQ ID NO 2
<211> LENGTH: 106
<212> TYPE: PRT
<213> ORGANISM: Artificial Sequence
<220> FEATURE:
<223> OTHER INFORMATION: CRB0022VK

<400> SEQUENCE: 2

Asp Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Arg Thr Arg Leu Glu Ile Lys
            100                 105

<210> SEQ ID NO 3
<211> LENGTH: 116
<212> TYPE: PRT
<213> ORGANISM: Artificial Sequence
<220> FEATURE:
<223> OTHER INFORMATION: CRB0036VH

<400> SEQUENCE: 3

Gln Val Gln Leu Gln Gln Ser Gly Ala Glu Leu Leu Lys Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Ala His Tyr Ser Glu Lys Phe
    50                  55                  60

Lys Asp Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Phe Cys
                85                  90                  95

Thr Arg Ser Pro Pro Asn Pro Gly Tyr Trp Gly Gln Gly Thr Ser Val
            100                 105                 110

Thr Val Ser Ser
        115

<210> SEQ ID NO 4
<211> LENGTH: 112
<212> TYPE: PRT
<213> ORGANISM: Artificial Sequence
<220> FEATURE:
<223> OTHER INFORMATION: CRB0036VK

<400> SEQUENCE: 4

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
```

```
            20                  25                  30
Ser Gly Ile Thr Ser Leu Tyr Trp Tyr Leu Gln Arg Pro Gly Gln Ser
            35                  40                  45

Pro Gln Leu Pro Ile Tyr Arg Met Ser Ser Leu Ala Ser Gly Val Pro
    50                  55                  60

Asp Arg Phe Ser Val Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110
```

<210> SEQ ID NO 5
<211> LENGTH: 123
<212> TYPE: PRT
<213> ORGANISM: Artificial Sequence
<220> FEATURE:
<223> OTHER INFORMATION: CRB0069VH

<400> SEQUENCE: 5

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Arg Leu Gly Arg Thr Tyr Tyr Arg Ser Lys Trp Tyr Asn Asp Tyr Ala
    50                  55                  60

Glu Ser Val Lys Ser Arg Ile Ile Ile Asn Ser Gly Thr Ser Lys Asn
65                  70                  75                  80

Gln Phe Ser Leu His Leu Asn Ser Val Thr Pro Glu Asp Thr Ala Val
                85                  90                  95

Tyr Tyr Cys Gly Arg Ala Lys Asp Gly Trp Tyr Asp Ala Phe Asp Ile
            100                 105                 110

Trp Gly Gln Gly Thr Thr Val Thr Val Ser Ser
        115                 120
```

<210> SEQ ID NO 6
<211> LENGTH: 110
<212> TYPE: PRT
<213> ORGANISM: Artificial Sequence
<220> FEATURE:
<223> OTHER INFORMATION: CRB0069VK

<400> SEQUENCE: 6

```
Gln Pro Gly Leu Thr Gln Pro Pro Ser Ala Ser Gly Thr Pro Gly Gln
1               5                   10                  15

Arg Val Thr Ile Ser Cys Thr Gly Ser Ser Ser Asn Val Gly Ala Gly
            20                  25                  30

Tyr Thr Val His Trp Tyr Gln Gln Leu Pro Gly Thr Ala Pro Thr Leu
        35                  40                  45

Leu Ile Tyr Asp Asn Asn Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Arg Ala Glu Asp Glu Ala Asp Tyr Tyr Cys Gln Ser Tyr Asp Arg Ser
                85                  90                  95
```

Arg Val Tyr Val Phe Gly Thr Gly Thr Lys Leu Thr Val Leu
        100                 105                 110

<210> SEQ ID NO 7
<211> LENGTH: 127
<212> TYPE: PRT
<213> ORGANISM: Artificial Sequence
<220> FEATURE:
<223> OTHER INFORMATION: CRB0072VH

<400> SEQUENCE: 7

Glu Val Gln Leu Val Glu Thr Gly Gly Gly Leu Val Gln Pro Gly Ser
1               5                   10                  15

Ser Leu Arg Leu Ser Cys Ala Thr Ser Gly Phe Thr Phe Ile Asn Tyr
            20                  25                  30

Gly Val His Trp Val Arg Gln Pro Pro Gly Lys Gly Leu Glu Trp Val
        35                  40                  45

Ala Ser Ile Trp Tyr Glu Gly Ser Asn Glu Lys Tyr Ala Asp Ser Val
    50                  55                  60

Lys Gly Arg Phe Thr Ile Ser Arg Asp Asn Ser Arg Tyr Thr Leu His
65                  70                  75                  80

Leu Gln Leu Asn Ser Leu Arg Ala Glu Asp Thr Ala Asp Tyr Tyr Cys
                85                  90                  95

Val Arg Asp Arg Gly Thr Gly Asp Tyr Arg Asn Ser Arg Phe Tyr Tyr
            100                 105                 110

Gly Met Asp Val Trp Gly Gln Gly Thr Thr Val Thr Val Ser Ser
        115                 120                 125

<210> SEQ ID NO 8
<211> LENGTH: 107
<212> TYPE: PRT
<213> ORGANISM: Artificial Sequence
<220> FEATURE:
<223> OTHER INFORMATION: CRB0072VK

<400> SEQUENCE: 8

Asp Ile Gln Met Thr Gln Ser Pro Ile Ser Leu Ser Ala Thr Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
    50                  55                  60

Ser Gly Ser Gly Thr Val Phe Thr Leu Thr Ile Ser Gly Leu Gln Pro
65                  70                  75                  80

Glu Asp Phe Ala Thr Tyr Cys Cys Gln Gln Ser His Ser Thr Ala Trp
                85                  90                  95

Thr Phe Gly Gln Gly Thr Lys Val Glu Ile Lys
            100                 105

<210> SEQ ID NO 9
<211> LENGTH: 117
<212> TYPE: PRT
<213> ORGANISM: Artificial Sequence
<220> FEATURE:
<223> OTHER INFORMATION: CRB0082VH

<400> SEQUENCE: 9

Gln Val Gln Leu Gln Gln Ser Gly Pro Gly Leu Val Lys Pro Ser Gln

```
               1               5                  10                 15
            Thr Leu Ser Leu Thr Cys Ala Ile Ser Gly Asp Ser Val Ser Phe
                            20                 25                 30

Thr Val Ala Trp Asn Trp Ile Arg Gln Ser Pro Ser Arg Gly Leu Glu
                        35                 40                 45

Arg Leu Gly Arg Thr Tyr Arg Arg Ser Lys Asp Tyr Ala Glu Tyr Met
                    50                 55                 60

Arg Ser Arg Leu Thr Ile Asn Ala Asp Thr Ser Lys Asn Gln Leu Ser
             65                 70                 75                 80

Leu Gln Leu Asp Ser Val Thr Pro Asp Thr Ala Val Tyr Tyr Cys
                            85                 90                 95

Ala Arg Gly Gln Asn Ser Ala Phe Asp Leu Trp Gly Gln Arg Thr Met
                        100                105                110

Val Thr Val Ser Ser
                        115

<210> SEQ ID NO 10
<211> LENGTH: 108
<212> TYPE: PRT
<213> ORGANISM: Artificial Sequence
<220> FEATURE:
<223> OTHER INFORMATION: CRB0082VL

<400> SEQUENCE: 10

Ser Tyr Val Leu Thr Gln Pro Pro Ser Val Ser Val Ala Pro Gly Thr
             1               5                  10                 15

Thr Ala Arg Leu Ser Cys Glu Ala Thr Lys Ile Gly Ser Gln Arg Leu
                            20                 25                 30

His Trp Tyr Gln Gln Lys Pro Gly Gln Ala Pro Val Met Val Ile Ser
                        35                 40                 45

Phe Asp Ser Asp Arg Pro Ser Gly Ile Pro Arg Phe Ser Gly Ser
                    50                 55                 60

Arg Ser Gly Asn Thr Ala Thr Leu Thr Ile Ser Gly Val Glu Ala Gly
             65                 70                 75                 80

Asp Glu Ala Asp Tyr Tyr Cys Asn Ser Arg Asp Ser Ser Gly Tyr His
                            85                 90                 95

Leu Val Phe Gly Gly Gly Thr Lys Leu Thr Val Leu
                        100                105

<210> SEQ ID NO 11
<211> LENGTH: 120
<212> TYPE: PRT
<213> ORGANISM: Artificial Sequence
<220> FEATURE:
<223> OTHER INFORMATION: CRB0084VH

<400> SEQUENCE: 11

Gln Val Gln Leu Gln Gln Trp Gly Ala Gly Leu Leu Arg Pro Ser Glu
             1               5                  10                 15

Thr Leu Ser Leu Thr Cys Thr Val Ser Gly Gly Ser Phe Ser Asp Ser
                            20                 25                 30

Tyr Trp Thr Trp Ile Arg Gln Ser Pro Gly Lys Gly Leu Glu Trp Ile
                        35                 40                 45

Gly Glu Asn Asn His Arg Gly Ser Thr Asn Tyr Ser Pro Thr Leu Arg
                    50                 55                 60

Ser Arg Leu Ser Ile Ser Ile Asp Ser Ser Lys Asn Gln Phe Ser Leu
             65                 70                 75                 80
```

```
Lys Leu Ser Ser Val Thr Ala Ala Asp Thr Ala Val Tyr Tyr Cys Ala
                85                  90                  95

Arg Val Pro Tyr Arg Leu Arg Ser Arg Ile Phe Asp Val Trp Gly Gln
            100                 105                 110

Gly Thr Met Val Thr Val Ser Ser
        115                 120

<210> SEQ ID NO 12
<211> LENGTH: 108
<212> TYPE: PRT
<213> ORGANISM: Artificial Sequence
<220> FEATURE:
<223> OTHER INFORMATION: CRB0084VL

<400> SEQUENCE: 12

Gln Pro Val Leu Thr Gln Pro Pro Ser Val Ser Val Ala Pro Arg Gln
1               5                   10                  15

Thr Ala Thr Ile Thr Cys Gly Gly Asn Tyr Ile Gly Ser Lys Ser Val
            20                  25                  30

His Trp Tyr Gln Gln Lys Pro Gly Gln Asp Pro Val Leu Val Val Asn
        35                  40                  45

Asp Asp Ser Asp Arg Pro Ser Gly Ile Pro Glu Arg Phe Ser Gly Ser
50                  55                  60

Asn Ser Ala Asn Thr Ala Thr Leu Thr Ile Ser Gly Val Glu Ala Gly
65                  70                  75                  80

Asp Glu Ala Asp Tyr Tyr Cys Gln Val Trp Asp Ser Ser Thr Glu Pro
                85                  90                  95

Val Val Phe Gly Gly Gly Thr Lys Leu Thr Val Leu
            100                 105

<210> SEQ ID NO 13
<211> LENGTH: 121
<212> TYPE: PRT
<213> ORGANISM: Artificial Sequence
<220> FEATURE:
<223> OTHER INFORMATION: CRB0088VH

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Ile Arg Asn Lys Ala Asn Ser Tyr Thr Thr Glu Tyr Ala Ala
50                  55                  60

Ser Val Lys Gly Arg Phe Thr Ile Ser Arg Asp Asp Ser Lys Lys Thr
65                  70                  75                  80

Leu Tyr Leu Gln Met Thr Ser Leu Lys Thr Asp Asp Thr Ala Leu Tyr
                85                  90                  95

Tyr Cys Ala Arg Asp Leu Gly Ala Ser Asp Ala Phe Asp Leu Trp Gly
            100                 105                 110

Gln Gly Thr Met Val Thr Val Ser Ser
        115                 120

<210> SEQ ID NO 14
<211> LENGTH: 111
<212> TYPE: PRT
<213> ORGANISM: Artificial Sequence
```

```
<220> FEATURE:
<223> OTHER INFORMATION: CRB0088VL

<400> SEQUENCE: 14

Gln Pro Val Leu Thr Gln Ser Pro Ala Ser Ala Ser Leu Gly Ala
1               5                  10                  15

Ser Val Lys Leu Thr Cys Thr Leu Ser Ser Gly His Ser Ser Tyr Ala
            20                  25                  30

Ile Ala Trp His Gln Gln Pro Glu Lys Gly Pro Arg Tyr Leu Met
        35                  40                  45

Lys Val Asn Ser Asp Gly Ser His Asn Lys Gly Asp Gly Ile Pro Asp
    50                  55                  60

Arg Phe Ser Gly Ser Arg Ser Gly Ala Glu Arg Tyr Leu Thr Ile Ser
65                  70                  75                  80

Ser Leu His Ser Glu Asp Glu Ala Asp Tyr Tyr Cys Gln Thr Trp Gly
                85                  90                  95

Ala Gly Gly Val Val Phe Gly Gly Gly Thr Lys Leu Thr Val Leu
            100                 105                 110

<210> SEQ ID NO 15
<211> LENGTH: 122
<212> TYPE: PRT
<213> ORGANISM: Artificial Sequence
<220> FEATURE:
<223> OTHER INFORMATION: CRB0089VH

<400> SEQUENCE: 15

Gln Val Gln Leu Gln Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Phe His Arg Ser Arg Trp Tyr Asn Glu Tyr Pro
    50                  55                  60

Val Ser Val Arg Ser Arg Ile Thr Ile Asn Pro Asp Thr Ser Asn Asn
65                  70                  75                  80

Gln Phe Thr Leu Gln Leu Asn Ser Val Thr Pro Asp Asp Thr Ala Val
                85                  90                  95

Tyr Tyr Cys Ala Arg Ala Pro Val Ala Gly Leu Thr Phe Asp Ile Trp
            100                 105                 110

Gly Gln Gly Thr Met Val Thr Val Ser Ser
        115                 120

<210> SEQ ID NO 16
<211> LENGTH: 105
<212> TYPE: PRT
<213> ORGANISM: Artificial Sequence
<220> FEATURE:
<223> OTHER INFORMATION: CRB0089VL

<400> SEQUENCE: 16

Gln Thr Val Val Thr Gln Glu Pro Ser Val Ser Gly Ala Pro Gly Gln
1               5                   10                  15

Arg Val Thr Ile Ser Cys Thr Gly Ser Ser Ile Ile Gly Ala Gly
            20                  25                  30

Tyr Glu Val His Trp Tyr Gln His Leu Pro Gly Thr Ala Pro Lys Leu
        35                  40                  45
```

```
Leu Ile Tyr Asp Ser Ile Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Ser Ala Ile Phe
                 85                  90                  95

Gly Gly Gly Thr Lys Leu Thr Val Leu
            100                 105

<210> SEQ ID NO 17
<211> LENGTH: 10
<212> TYPE: PRT
<213> ORGANISM: Artificial Sequence
<220> FEATURE:
<223> OTHER INFORMATION: CDRL1_22

<400> SEQUENCE: 17

Ser Ala Ser Ser Ser Val Ser Tyr Met Tyr
1               5                   10

<210> SEQ ID NO 18
<211> LENGTH: 7
<212> TYPE: PRT
<213> ORGANISM: Artificial Sequence
<220> FEATURE:
<223> OTHER INFORMATION: CDRL2_22

<400> SEQUENCE: 18

Leu Thr Ser Asn Leu Ala Ser
1               5

<210> SEQ ID NO 19
<211> LENGTH: 9
<212> TYPE: PRT
<213> ORGANISM: Artificial Sequence
<220> FEATURE:
<223> OTHER INFORMATION: CDRL3_22

<400> SEQUENCE: 19

Gln Gln Trp Ser Ser Asn Pro Tyr Thr
1               5

<210> SEQ ID NO 20
<211> LENGTH: 16
<212> TYPE: PRT
<213> ORGANISM: Artificial Sequence
<220> FEATURE:
<223> OTHER INFORMATION: CDRL1_36

<400> SEQUENCE: 20

Arg Ser Ser Lys Ser Leu Leu His Ser Ser Gly Ile Thr Ser Leu Tyr
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: CDRL2_36

<400> SEQUENCE: 21

Arg Met Ser Ser Leu Ala Ser
1               5

<210> SEQ ID NO 22
```

```
<211> LENGTH: 9
<212> TYPE: PRT
<213> ORGANISM: Artificial Sequence
<220> FEATURE:
<223> OTHER INFORMATION: CDRL3_36

<400> SEQUENCE: 22

Met Gln His Leu Glu Tyr Pro Leu Thr
1               5

<210> SEQ ID NO 23
<211> LENGTH: 14
<212> TYPE: PRT
<213> ORGANISM: Artificial Sequence
<220> FEATURE:
<223> OTHER INFORMATION: CDRL1_69

<400> SEQUENCE: 23

Thr Gly Ser Ser Ser Asn Val Gly Ala Gly Tyr Thr Val His
1               5                   10

<210> SEQ ID NO 24
<211> LENGTH: 7
<212> TYPE: PRT
<213> ORGANISM: Artificial Sequence
<220> FEATURE:
<223> OTHER INFORMATION: CDRL2_69

<400> SEQUENCE: 24

Asp Asn Asn Asn Arg Pro Ser
1               5

<210> SEQ ID NO 25
<211> LENGTH: 10
<212> TYPE: PRT
<213> ORGANISM: Artificial Sequence
<220> FEATURE:
<223> OTHER INFORMATION: CDRL3_69

<400> SEQUENCE: 25

Gln Ser Tyr Asp Arg Ser Arg Val Tyr Val
1               5                   10

<210> SEQ ID NO 26
<211> LENGTH: 11
<212> TYPE: PRT
<213> ORGANISM: Artificial Sequence
<220> FEATURE:
<223> OTHER INFORMATION: CDRL1_72

<400> SEQUENCE: 26

Arg Ala Ser Gln Ser Ile Gly Arg Tyr Leu Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: CDRL2_72

<400> SEQUENCE: 27

Gly Ala Ser Ser Leu Glu Ser
1               5

<210> SEQ ID NO 28
<211> LENGTH: 9
```

```
<212> TYPE: PRT
<213> ORGANISM: Artificial Sequence
<220> FEATURE:
<223> OTHER INFORMATION: CDRL3_72

<400> SEQUENCE: 28

Gln Gln Ser His Ser Thr Ala Trp Thr
1               5

<210> SEQ ID NO 29
<211> LENGTH: 11
<212> TYPE: PRT
<213> ORGANISM: Artificial Sequence
<220> FEATURE:
<223> OTHER INFORMATION: CDRL1_82

<400> SEQUENCE: 29

Glu Ala Thr Lys Ile Gly Ser Gln Arg Leu His
1               5                   10

<210> SEQ ID NO 30
<211> LENGTH: 7
<212> TYPE: PRT
<213> ORGANISM: Artificial Sequence
<220> FEATURE:
<223> OTHER INFORMATION: CDRL2_82

<400> SEQUENCE: 30

Phe Asp Ser Asp Arg Pro Ser
1               5

<210> SEQ ID NO 31
<211> LENGTH: 11
<212> TYPE: PRT
<213> ORGANISM: Artificial Sequence
<220> FEATURE:
<223> OTHER INFORMATION: CDRL3_82

<400> SEQUENCE: 31

Asn Ser Arg Asp Ser Ser Gly Tyr His Leu Val
1               5                   10

<210> SEQ ID NO 32
<211> LENGTH: 11
<212> TYPE: PRT
<213> ORGANISM: Artificial Sequence
<220> FEATURE:
<223> OTHER INFORMATION: CDRL1_84

<400> SEQUENCE: 32

Gly Gly Asn Tyr Ile Gly Ser Lys Ser Val His
1               5                   10

<210> SEQ ID NO 33
<211> LENGTH: 7
<212> TYPE: PRT
<213> ORGANISM: Artificial Sequence
<220> FEATURE:
<223> OTHER INFORMATION: CDRL2_84

<400> SEQUENCE: 33

Asp Asp Ser Asp Arg Pro Ser
1               5

<210> SEQ ID NO 34
<211> LENGTH: 11
<212> TYPE: PRT
```

<213> ORGANISM: Artificial Sequence
<220> FEATURE:
<223> OTHER INFORMATION: CDRL3_84

<400> SEQUENCE: 34

Gln Val Trp Asp Ser Ser Thr Glu Pro Val Val
1               5                   10

<210> SEQ ID NO 35
<211> LENGTH: 12
<212> TYPE: PRT
<213> ORGANISM: Artificial Sequence
<220> FEATURE:
<223> OTHER INFORMATION: CDRL1_88

<400> SEQUENCE: 35

Thr Leu Ser Ser Gly His Ser Ser Tyr Ala Ile Ala
1               5                   10

<210> SEQ ID NO 36
<211> LENGTH: 11
<212> TYPE: PRT
<213> ORGANISM: Artificial Sequence
<220> FEATURE:
<223> OTHER INFORMATION: CDRL2_88

<400> SEQUENCE: 36

Val Asn Ser Asp Gly Ser His Asn Lys Gly Asp
1               5                   10

<210> SEQ ID NO 37
<211> LENGTH: 9
<212> TYPE: PRT
<213> ORGANISM: Artificial Sequence
<220> FEATURE:
<223> OTHER INFORMATION: CDRL3_88

<400> SEQUENCE: 37

Gln Thr Trp Gly Ala Gly Gly Val Val
1               5

<210> SEQ ID NO 38
<211> LENGTH: 14
<212> TYPE: PRT
<213> ORGANISM: Artificial Sequence
<220> FEATURE:
<223> OTHER INFORMATION: CDRL1_89

<400> SEQUENCE: 38

Thr Gly Ser Ser Ser Ile Ile Gly Ala Gly Tyr Glu Val His
1               5                   10

<210> SEQ ID NO 39
<211> LENGTH: 7
<212> TYPE: PRT
<213> ORGANISM: Artificial Sequence
<220> FEATURE:
<223> OTHER INFORMATION: CDRL2_89

<400> SEQUENCE: 39

Asp Ser Ile Asn Arg Pro Ser
1               5

<210> SEQ ID NO 40
<211> LENGTH: 5
<212> TYPE: PRT
<213> ORGANISM: Artificial Sequence

```
<220> FEATURE:
<223> OTHER INFORMATION: CDRL3_89

<400> SEQUENCE: 40

Gln Ser Ser Ala Ile
1               5

<210> SEQ ID NO 41
<211> LENGTH: 5
<212> TYPE: PRT
<213> ORGANISM: Artificial Sequence
<220> FEATURE:
<223> OTHER INFORMATION: CDRH1_22

<400> SEQUENCE: 41

Asp Thr Tyr Met His
1               5

<210> SEQ ID NO 42
<211> LENGTH: 17
<212> TYPE: PRT
<213> ORGANISM: Artificial Sequence
<220> FEATURE:
<223> OTHER INFORMATION: CDRH2_22

<400> SEQUENCE: 42

Gly Ile Asp Pro Ala Asn Gly Asn Thr Ile Tyr Val Pro Lys Phe Gln
1               5                   10                  15

Gly

<210> SEQ ID NO 43
<211> LENGTH: 11
<212> TYPE: PRT
<213> ORGANISM: Artificial Sequence
<220> FEATURE:
<223> OTHER INFORMATION: CDRH3_22

<400> SEQUENCE: 43

Gly Gly Tyr Asp Phe Asp Tyr Ala Met Asp Tyr
1               5                   10

<210> SEQ ID NO 44
<211> LENGTH: 5
<212> TYPE: PRT
<213> ORGANISM: Artificial Sequence
<220> FEATURE:
<223> OTHER INFORMATION: CDRH1_36

<400> SEQUENCE: 44

Asn Tyr Trp Ile Glu
1               5

<210> SEQ ID NO 45
<211> LENGTH: 17
<212> TYPE: PRT
<213> ORGANISM: Artificial Sequence
<220> FEATURE:
<223> OTHER INFORMATION: CDRH2_36

<400> SEQUENCE: 45

Glu Ile Leu Pro Gly Ser Gly Ser Ala His Tyr Ser Glu Lys Phe Lys
1               5                   10                  15

Asp

<210> SEQ ID NO 46
```

```
<211> LENGTH: 7
<212> TYPE: PRT
<213> ORGANISM: Artificial Sequence
<220> FEATURE:
<223> OTHER INFORMATION: CDRH3_36

<400> SEQUENCE: 46

Ser Pro Pro Asn Pro Gly Tyr
1               5

<210> SEQ ID NO 47
<211> LENGTH: 7
<212> TYPE: PRT
<213> ORGANISM: Artificial Sequence
<220> FEATURE:
<223> OTHER INFORMATION: CDRH1_69

<400> SEQUENCE: 47

Ser Asn Ser Ala Ala Trp Asn
1               5

<210> SEQ ID NO 48
<211> LENGTH: 18
<212> TYPE: PRT
<213> ORGANISM: Artificial Sequence
<220> FEATURE:
<223> OTHER INFORMATION: CDRH2_69

<400> SEQUENCE: 48

Arg Thr Tyr Tyr Arg Ser Lys Trp Tyr Asn Asp Tyr Ala Glu Ser Val
1               5                   10                  15

Lys Ser

<210> SEQ ID NO 49
<211> LENGTH: 11
<212> TYPE: PRT
<213> ORGANISM: Artificial Sequence
<220> FEATURE:
<223> OTHER INFORMATION: CDRH3_69

<400> SEQUENCE: 49

Ala Lys Asp Gly Trp Tyr Asp Ala Phe Asp Ile
1               5                   10

<210> SEQ ID NO 50
<211> LENGTH: 5
<212> TYPE: PRT
<213> ORGANISM: Artificial Sequence
<220> FEATURE:
<223> OTHER INFORMATION: CDRH1_72

<400> SEQUENCE: 50

Asn Tyr Gly Val His
1               5

<210> SEQ ID NO 51
<211> LENGTH: 17
<212> TYPE: PRT
<213> ORGANISM: Artificial Sequence
<220> FEATURE:
<223> OTHER INFORMATION: CDRH2_72

<400> SEQUENCE: 51

Ser Ile Trp Tyr Glu Gly Ser Asn Glu Lys Tyr Ala Asp Ser Val Lys
1               5                   10                  15

Gly
```

```
<210> SEQ ID NO 52
<211> LENGTH: 18
<212> TYPE: PRT
<213> ORGANISM: Artificial Sequence
<220> FEATURE:
<223> OTHER INFORMATION: CDRH3_72

<400> SEQUENCE: 52

Asp Arg Gly Thr Gly Asp Tyr Arg Asn Ser Arg Phe Tyr Tyr Gly Met
1               5                   10                  15
Asp Val

<210> SEQ ID NO 53
<211> LENGTH: 7
<212> TYPE: PRT
<213> ORGANISM: Artificial Sequence
<220> FEATURE:
<223> OTHER INFORMATION: CDRH1_82

<400> SEQUENCE: 53

Ser Phe Thr Val Ala Trp Asn
1               5

<210> SEQ ID NO 54
<211> LENGTH: 15
<212> TYPE: PRT
<213> ORGANISM: Artificial Sequence
<220> FEATURE:
<223> OTHER INFORMATION: CDRH2_82

<400> SEQUENCE: 54

Arg Thr Tyr Arg Arg Ser Lys Asp Tyr Ala Glu Tyr Met Arg Ser
1               5                   10                  15

<210> SEQ ID NO 55
<211> LENGTH: 8
<212> TYPE: PRT
<213> ORGANISM: Artificial Sequence
<220> FEATURE:
<223> OTHER INFORMATION: CDRH3_82

<400> SEQUENCE: 55

Gly Gln Asn Ser Ala Phe Asp Leu
1               5

<210> SEQ ID NO 56
<211> LENGTH: 5
<212> TYPE: PRT
<213> ORGANISM: Artificial Sequence
<220> FEATURE:
<223> OTHER INFORMATION: CDRH1_84

<400> SEQUENCE: 56

Asp Ser Tyr Trp Thr
1               5

<210> SEQ ID NO 57
<211> LENGTH: 16
<212> TYPE: PRT
<213> ORGANISM: Artificial Sequence
<220> FEATURE:
<223> OTHER INFORMATION: CDRH2_84

<400> SEQUENCE: 57

Glu Asn Asn His Arg Gly Ser Thr Asn Tyr Ser Pro Thr Leu Arg Ser
```

-continued

```
<210> SEQ ID NO 58
<211> LENGTH: 12
<212> TYPE: PRT
<213> ORGANISM: Artificial Sequence
<220> FEATURE:
<223> OTHER INFORMATION: CDRH3_84

<400> SEQUENCE: 58

Val Pro Tyr Arg Leu Arg Ser Arg Ile Phe Asp Val
1               5                   10

<210> SEQ ID NO 59
<211> LENGTH: 5
<212> TYPE: PRT
<213> ORGANISM: Artificial Sequence
<220> FEATURE:
<223> OTHER INFORMATION: CDRH1_88

<400> SEQUENCE: 59

Asp His Tyr Met Asp
1               5

<210> SEQ ID NO 60
<211> LENGTH: 19
<212> TYPE: PRT
<213> ORGANISM: Artificial Sequence
<220> FEATURE:
<223> OTHER INFORMATION: CDRH2_88

<400> SEQUENCE: 60

Arg Ile Arg Asn Lys Ala Asn Ser Tyr Thr Thr Glu Tyr Ala Ala Ser
1               5                   10                  15

Val Lys Gly

<210> SEQ ID NO 61
<211> LENGTH: 10
<212> TYPE: PRT
<213> ORGANISM: Artificial Sequence
<220> FEATURE:
<223> OTHER INFORMATION: CDRH3_88

<400> SEQUENCE: 61

Asp Leu Gly Ala Ser Asp Ala Phe Asp Leu
1               5                   10

<210> SEQ ID NO 62
<211> LENGTH: 7
<212> TYPE: PRT
<213> ORGANISM: Artificial Sequence
<220> FEATURE:
<223> OTHER INFORMATION: CDRH1_89

<400> SEQUENCE: 62

Ser Asn Ser Ala Ala Trp Asn
1               5

<210> SEQ ID NO 63
<211> LENGTH: 18
<212> TYPE: PRT
<213> ORGANISM: Artificial Sequence
<220> FEATURE:
<223> OTHER INFORMATION: CDRH2_89

<400> SEQUENCE: 63
```

```
Arg Thr Phe His Arg Ser Arg Trp Tyr Asn Glu Tyr Pro Val Ser Val
 1               5                  10                  15

Arg Ser

<210> SEQ ID NO 64
<211> LENGTH: 10
<212> TYPE: PRT
<213> ORGANISM: Artificial Sequence
<220> FEATURE:
<223> OTHER INFORMATION: CDRH3_89

<400> SEQUENCE: 64

Ala Pro Val Ala Gly Leu Thr Phe Asp Ile
 1               5                  10

<210> SEQ ID NO 65
<211> LENGTH: 796
<212> TYPE: PRT
<213> ORGANISM: Homo sapiens

<400> SEQUENCE: 65

Met Leu Arg Gly Gly Arg Arg Gly Gln Leu Gly Trp His Ser Trp Ala
 1               5                  10                  15

Ala Gly Pro Gly Ser Leu Leu Ala Trp Leu Ile Leu Ala Ser Ala Gly
                20                  25                  30

Ala Ala Pro Cys Pro Asp Ala Cys Cys Pro His Gly Ser Ser Gly Leu
            35                  40                  45

Arg Cys Thr Arg Asp Gly Ala Leu Asp Ser Leu His His Leu Pro Gly
        50                  55                  60

Ala Glu Asn Leu Thr Glu Leu Tyr Ile Glu Asn Gln Gln His Leu Gln
 65                  70                  75                  80

His Leu Glu Leu Arg Asp Leu Arg Gly Leu Gly Glu Leu Arg Asn Leu
                85                  90                  95

Thr Ile Val Lys Ser Gly Leu Arg Phe Val Ala Pro Asp Ala Phe His
                100                 105                 110

Phe Thr Pro Arg Leu Ser Arg Leu Asn Leu Ser Phe Asn Ala Leu Glu
            115                 120                 125

Ser Leu Ser Trp Lys Thr Val Gln Gly Leu Ser Leu Gln Glu Leu Val
        130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
            180                 185                 190

Val Pro Thr Leu Lys Val Gln Val Pro Asn Ala Ser Val Asp Val Gly
        195                 200                 205

Asp Asp Val Leu Leu Arg Cys Gln Val Glu Gly Arg Gly Leu Glu Gln
    210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
            260                 265                 270

Arg Ala Glu Val Ser Val Gln Val Asn Val Ser Phe Pro Ala Ser Val
        275                 280                 285
```

```
Gln Leu His Thr Ala Val Glu Met His His Trp Cys Ile Pro Phe Ser
    290                 295                 300

Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
                340                 345                 350

His Val Asn Asn Gly Asn Tyr Thr Leu Leu Ala Ala Asn Pro Phe Gly
            355                 360                 365

Gln Ala Ser Ala Ser Ile Met Ala Ala Phe Met Asp Asn Pro Phe Glu
    370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Lys Asp Glu Thr Pro Phe
                405                 410                 415

Gly Val Ser Val Ala Val Gly Leu Ala Val Phe Ala Cys Leu Phe Leu
                420                 425                 430

Ser Thr Leu Leu Leu Val Leu Asn Lys Cys Gly Arg Arg Asn Lys Phe
            435                 440                 445

Gly Ile Asn Arg Pro Ala Val Leu Ala Pro Glu Asp Gly Leu Ala Met
    450                 455                 460

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
                485                 490                 495

Phe Ser Asp Ala Cys Val His His Ile Lys Arg Arg Asp Ile Val Leu
                500                 505                 510

Lys Trp Glu Leu Gly Glu Gly Ala Phe Gly Lys Val Phe Leu Ala Glu
            515                 520                 525

Cys His Asn Leu Leu Pro Glu Gln Asp Lys Met Leu Val Ala Val Lys
    530                 535                 540

Ala Leu Lys Glu Ala Ser Glu Ser Ala Arg Gln Asp Phe Gln Arg Glu
545                 550                 555                 560

Ala Glu Leu Leu Thr Met Leu Gln His Gln His Ile Val Arg Phe Phe
                565                 570                 575

Gly Val Cys Thr Glu Gly Arg Pro Leu Leu Met Val Phe Glu Tyr Met
                580                 585                 590

Arg His Gly Asp Leu Asn Arg Phe Leu Arg Ser His Gly Pro Asp Ala
            595                 600                 605

Lys Leu Leu Ala Gly Gly Glu Asp Val Ala Pro Gly Pro Leu Gly Leu
    610                 615                 620

Gly Gln Leu Leu Ala Val Ala Ser Gln Val Ala Ala Gly Met Val Tyr
625                 630                 635                 640

Leu Ala Gly Leu His Phe Val His Arg Asp Leu Ala Thr Arg Asn Cys
                645                 650                 655

Leu Val Gly Gln Gly Leu Val Val Lys Ile Gly Asp Phe Gly Met Ser
                660                 665                 670

Arg Asp Ile Tyr Ser Thr Asp Tyr Tyr Arg Val Gly Gly Arg Thr Met
            675                 680                 685

Leu Pro Ile Arg Trp Met Pro Pro Glu Ser Ile Leu Tyr Arg Lys Phe
    690                 695                 700
```

```
Thr Thr Glu Ser Asp Val Trp Ser Phe Gly Val Leu Trp Glu Ile
705                 710                 715                 720

Phe Thr Tyr Gly Lys Gln Pro Trp Tyr Gln Leu Ser Asn Thr Glu Ala
            725                 730                 735

Ile Asp Cys Ile Thr Gln Gly Arg Glu Leu Glu Arg Pro Arg Ala Cys
                740                 745                 750

Pro Pro Glu Val Tyr Ala Ile Met Arg Gly Cys Trp Gln Arg Glu Pro
            755                 760                 765

Gln Gln Arg His Ser Ile Lys Asp Val His Ala Arg Leu Gln Ala Leu
            770                 775                 780

Ala Gln Ala Pro Pro Val Tyr Leu Asp Val Leu Gly
785                 790                 795

<210> SEQ ID NO 66
<211> LENGTH: 6
<212> TYPE: PRT
<213> ORGANISM: Homo sapiens

<400> SEQUENCE: 66

Val Glu Met His His Trp
1               5

<210> SEQ ID NO 67
<211> LENGTH: 6
<212> TYPE: PRT
<213> ORGANISM: Mus musculus

<400> SEQUENCE: 67

Val Glu Gln His His Trp
1               5

<210> SEQ ID NO 68
<211> LENGTH: 285
<212> TYPE: DNA
<213> ORGANISM: Homo sapiens

<400> SEQUENCE: 68
ctaatagaag tggaaaagcc tctgtacgga gtagaggtgt tgttggtga aacagcccac      60 tttgaaattg aactttctgt ggagatgcac cactgggttc acggccagtg aagctgaaa     120 ggacagcctt tgacagcttc ccctgactgt gaaatcattg aggatggaaa gaagcatatt    180
ctgatccttc ataactgtca gctgggtatg acaggagagg tttccttcca ggtggagatg    240
caccactgga atctgcagc caatctgaaa gtgaaagaat tgtaa                     285

<210> SEQ ID NO 69
<211> LENGTH: 94
<212> TYPE: PRT
<213> ORGANISM: Homo sapiens

<400> SEQUENCE: 69

Leu Ile Glu Val Glu Lys Pro Leu Tyr Gly Val Glu Val Phe Val Gly
1               5                   10                  15

Glu Thr Ala His Phe Glu Ile Glu Leu Ser Val Glu Met His His Trp
            20                  25                  30

Val His Gly Gln Trp Lys Leu Lys Gly Gln Pro Leu Thr Ala Ser Pro
        35                  40                  45

Asp Cys Glu Ile Ile Glu Asp Gly Lys Lys His Ile Leu Ile Leu His
    50                  55                  60

Asn Cys Gln Leu Gly Met Thr Gly Glu Val Ser Phe Gln Val Glu Met
```

```
                65                  70                  75                  80
His His Trp Lys Ser Ala Ala Asn Leu Lys Val Lys Glu Leu
                    85                  90

<210> SEQ ID NO 70
<211> LENGTH: 667
<212> TYPE: PRT
<213> ORGANISM: Artificial Sequence
<220> FEATURE:
<223> OTHER INFORMATION: Human TrkA-CamelFc

<400> SEQUENCE: 70

Met Leu Arg Gly Gly Arg Arg Gly Gln Leu Gly Trp His Ser Trp Ala
1               5                   10                  15

Ala Gly Pro Gly Ser Leu Leu Ala Trp Leu Ile Leu Ala Ser Ala Gly
                20                  25                  30

Ala Ala Pro Cys Pro Asp Ala Cys Cys Pro His Gly Ser Ser Gly Leu
            35                  40                  45

Arg Cys Thr Arg Asp Gly Ala Leu Asp Ser Leu His His Leu Pro Gly
        50                  55                  60

Ala Glu Asn Leu Thr Glu Leu Tyr Ile Glu Asn Gln Gln His Leu Gln
65                  70                  75                  80

His Leu Glu Leu Arg Asp Leu Arg Gly Leu Gly Glu Leu Arg Asn Leu
                85                  90                  95

Thr Ile Val Lys Ser Gly Leu Arg Phe Val Ala Pro Asp Ala Phe His
                100                 105                 110

Phe Thr Pro Arg Leu Ser Arg Leu Asn Leu Ser Phe Asn Ala Leu Glu
            115                 120                 125

Ser Leu Ser Trp Lys Thr Val Gln Gly Leu Ser Leu Gln Glu Leu Val
        130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
                180                 185                 190

Val Pro Thr Leu Lys Val Gln Val Pro Asn Ala Ser Val Asp Val Gly
            195                 200                 205

Asp Asp Val Leu Leu Arg Cys Gln Val Glu Gly Arg Gly Leu Glu Gln
        210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
                260                 265                 270

Arg Ala Glu Val Ser Val Gln Val Asn Val Ser Phe Pro Ala Ser Val
            275                 280                 285

Gln Leu His Thr Ala Val Glu Met His His Trp Cys Ile Pro Phe Ser
        290                 295                 300

Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
```

```
                        340                 345                 350
His Val Asn Asn Gly Asn Tyr Thr Leu Leu Ala Ala Asn Pro Phe Gly
                355                 360                 365

Gln Ala Ser Ala Ser Ile Met Ala Ala Phe Met Asp Asn Pro Phe Glu
            370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Ala Ala Asp Arg Lys
                405                 410                 415

Ile Pro Gln Pro Gln Pro Lys Pro Gln Pro Gln Pro Gln Pro
                420                 425                 430

Lys Pro Gln Pro Lys Pro Glu Pro Glu Cys Thr Cys Pro Lys Cys Pro
                435                 440                 445

Ala Pro Glu Leu Pro Gly Gly Pro Ser Val Phe Val Phe Pro Pro Lys
            450                 455                 460

Pro Lys Asp Val Leu Ser Ile Ser Gly Arg Pro Glu Val Thr Cys Val
465                 470                 475                 480

Val Val Asp Val Gly Lys Lys Asp Pro Glu Val Asn Phe Asn Trp Tyr
                485                 490                 495

Val Asp Gly Val Glu Val Arg Thr Ala Asn Thr Lys Pro Lys Glu Glu
            500                 505                 510

Gln Phe Asn Ser Thr Tyr Arg Val Val Ser Val Leu Thr Ile Gln His
            515                 520                 525

Gln Asp Trp Leu Thr Gly Lys Glu Phe Lys Cys Lys Val Asn Asn Lys
        530                 535                 540

Ala Leu Pro Ala Pro Ile Glu Arg Thr Ile Ser Lys Ala Lys Gly Gln
545                 550                 555                 560

Thr Arg Glu Pro Gln Val Tyr Thr Leu Ala Pro His Arg Glu Glu Leu
                565                 570                 575

Ala Lys Asp Thr Val Ser Val Thr Cys Leu Val Lys Gly Phe Tyr Pro
            580                 585                 590

Pro Asp Ile Asn Val Glu Trp Gln Arg Asn Arg Gln Pro Glu Ser Glu
            595                 600                 605

Gly Ala Tyr Ala Thr Thr Leu Pro Gln Leu Asp Asn Asp Gly Thr Tyr
            610                 615                 620

Phe Leu Tyr Ser Lys Leu Ser Val Gly Lys Asn Thr Trp Gln Arg Gly
625                 630                 635                 640

Glu Thr Phe Thr Cys Val Val Met His Glu Ala Leu His Asn His Tyr
                645                 650                 655

Thr Gln Lys Ser Ile Thr Gln Ser Ser Gly Lys
                660                 665

<210> SEQ ID NO 71
<211> LENGTH: 687
<212> TYPE: PRT
<213> ORGANISM: Artificial Sequence
<220> FEATURE:
<223> OTHER INFORMATION: human TrkB-CamelFc

<400> SEQUENCE: 71

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
```

```
                35                  40                  45
Ser Pro Gly Ile Val Ala Phe Pro Arg Leu Glu Pro Asn Ser Val Asp
 50                  55                  60
Pro Glu Asn Ile Thr Glu Ile Phe Ile Ala Asn Gln Lys Arg Leu Glu
 65                  70                  75                  80
Ile Ile Asn Glu Asp Asp Val Glu Ala Tyr Val Gly Leu Arg Asn Leu
                 85                  90                  95
Thr Ile Val Asp Ser Gly Leu Lys Phe Val Ala His Lys Ala Phe Leu
                100                 105                 110
Lys Asn Ser Asn Leu Gln His Ile Asn Phe Thr Arg Asn Lys Leu Thr
            115                 120                 125
Ser Leu Ser Arg Lys His Phe Arg His Leu Asp Leu Ser Glu Leu Ile
        130                 135                 140
Leu Val Gly Asn Pro Phe Thr Cys Ser Cys Asp Ile Met Trp Ile Lys
145                 150                 155                 160
Thr Leu Gln Glu Ala Lys Ser Ser Pro Asp Thr Gln Asp Leu Tyr Cys
                165                 170                 175
Leu Asn Glu Ser Ser Lys Asn Ile Pro Leu Ala Asn Leu Gln Ile Pro
            180                 185                 190
Asn Cys Gly Leu Pro Ser Ala Asn Leu Ala Ala Pro Asn Leu Thr Val
        195                 200                 205
Glu Glu Gly Lys Ser Ile Thr Leu Ser Cys Ser Val Ala Gly Asp Pro
210                 215                 220
Val Pro Asn Met Tyr Trp Asp Val Gly Asn Leu Val Ser Lys His Met
225                 230                 235                 240
Asn Glu Thr Ser His Thr Gln Gly Ser Leu Arg Ile Thr Asn Ile Ser
                245                 250                 255
Ser Asp Asp Ser Gly Lys Gln Ile Ser Cys Val Ala Glu Asn Leu Val
            260                 265                 270
Gly Glu Asp Gln Asp Ser Val Asn Leu Thr Val His Phe Ala Pro Thr
        275                 280                 285
Ile Thr Phe Leu Glu Ser Pro Thr Ser Asp His His Trp Cys Ile Pro
290                 295                 300
Phe Thr Val Lys Gly Asn Pro Lys Pro Ala Leu Gln Trp Phe Tyr Asn
305                 310                 315                 320
Gly Ala Ile Leu Asn Glu Ser Lys Tyr Ile Cys Thr Lys Ile His Val
                325                 330                 335
Thr Asn His Thr Glu Tyr His Gly Cys Leu Gln Leu Asp Asn Pro Thr
            340                 345                 350
His Met Asn Asn Gly Asp Tyr Thr Leu Ile Ala Lys Asn Glu Tyr Gly
        355                 360                 365
Lys Asp Glu Lys Gln Ile Ser Ala His Phe Met Gly Trp Pro Gly Ile
    370                 375                 380
Asp Asp Gly Ala Asn Pro Asn Tyr Pro Asp Val Ile Tyr Glu Asp Tyr
385                 390                 395                 400
Gly Thr Ala Ala Asn Asp Ile Gly Asp Thr Thr Asn Arg Ser Asn Glu
                405                 410                 415
Ile Pro Ser Thr Asp Val Thr Asp Lys Thr Gly Arg Glu His Ala Ala
            420                 425                 430
Ala Asp Arg Lys Ile Pro Gln Pro Gln Pro Lys Pro Gln Pro Gln Pro
        435                 440                 445
Gln Pro Gln Pro Lys Pro Gln Pro Lys Pro Glu Pro Glu Cys Thr Cys
450                 455                 460
```

```
Pro Lys Cys Pro Ala Pro Glu Leu Pro Gly Gly Pro Ser Val Phe Val
465                 470                 475                 480

Phe Pro Pro Lys Pro Lys Asp Val Leu Ser Ile Ser Gly Arg Pro Glu
                485                 490                 495

Val Thr Cys Val Val Val Asp Val Gly Lys Lys Asp Pro Glu Val Asn
            500                 505                 510

Phe Asn Trp Tyr Val Asp Gly Val Glu Val Arg Thr Ala Asn Thr Lys
            515                 520                 525

Pro Lys Glu Glu Gln Phe Asn Ser Thr Tyr Arg Val Val Ser Val Leu
530                 535                 540

Thr Ile Gln His Gln Asp Trp Leu Thr Gly Lys Glu Phe Lys Cys Lys
545                 550                 555                 560

Val Asn Asn Lys Ala Leu Pro Ala Pro Ile Glu Arg Thr Ile Ser Lys
                565                 570                 575

Ala Lys Gly Gln Thr Arg Glu Pro Gln Val Tyr Thr Leu Ala Pro His
            580                 585                 590

Arg Glu Glu Leu Ala Lys Asp Thr Val Ser Val Thr Cys Leu Val Lys
            595                 600                 605

Gly Phe Tyr Pro Pro Asp Ile Asn Val Glu Trp Gln Arg Asn Arg Gln
610                 615                 620

Pro Glu Ser Glu Gly Ala Tyr Ala Thr Thr Leu Pro Gln Leu Asp Asn
625                 630                 635                 640

Asp Gly Thr Tyr Phe Leu Tyr Ser Lys Leu Ser Val Gly Lys Asn Thr
                645                 650                 655

Trp Gln Arg Gly Glu Thr Phe Thr Cys Val Val Met His Glu Ala Leu
            660                 665                 670

His Asn His Tyr Thr Gln Lys Ser Ile Thr Gln Ser Ser Gly Lys
            675                 680                 685
```

<210> SEQ ID NO 72
<211> LENGTH: 686
<212> TYPE: PRT
<213> ORGANISM: Artificial Sequence
<220> FEATURE:
<223> OTHER INFORMATION: human TrkC-CamelFc

<400> SEQUENCE: 72

```
Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
            20                  25                  30

Pro Ala Asn Cys Val Cys Ser Lys Thr Glu Ile Asn Cys Arg Arg Pro
        35                  40                  45

Asp Asp Gly Asn Leu Phe Pro Leu Leu Glu Gly Gln Asp Ser Gly Asn
    50                  55                  60

Ser Asn Gly Asn Ala Ser Ile Asn Ile Thr Asp Ile Ser Arg Asn Ile
65                  70                  75                  80

Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
            100                 105                 110

Ser Gly Leu Arg Ser Ile Gln Pro Arg Ala Phe Ala Lys Asn Pro His
        115                 120                 125

Leu Arg Tyr Ile Asn Leu Ser Ser Asn Arg Leu Thr Thr Leu Ser Trp
    130                 135                 140
```

-continued

```
Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu
                165                 170                 175

Gln Gly Glu Ala Lys Leu Asn Ser Gln Asn Leu Tyr Cys Ile Asn Ala
            180                 185                 190

Asp Gly Ser Gln Leu Pro Leu Phe Arg Met Asn Ile Ser Gln Cys Asp
            195                 200                 205

Leu Pro Glu Ile Ser Val Ser His Val Asn Leu Thr Val Arg Glu Gly
210                 215                 220

Asp Asn Ala Val Ile Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
                245                 250                 255

Asn Leu Asn Trp Thr Asn Val His Ala Ile Asn Leu Thr Leu Val Asn
                260                 265                 270

Val Thr Ser Glu Asp Asn Gly Phe Thr Leu Thr Cys Ile Ala Glu Asn
            275                 280                 285

Val Val Gly Met Ser Asn Ala Ser Val Ala Leu Thr Val Tyr Tyr Pro
290                 295                 300

Pro Arg Val Val Ser Leu Glu Glu Pro Glu Leu Arg Leu Glu His Cys
305                 310                 315                 320

Ile Glu Phe Val Val Arg Gly Asn Pro Pro Pro Thr Leu His Trp Leu
                325                 330                 335

His Asn Gly Gln Pro Leu Arg Glu Ser Lys Ile Ile His Val Glu Tyr
            340                 345                 350

Tyr Gln Glu Gly Glu Ile Ser Glu Gly Cys Leu Leu Phe Asn Lys Pro
            355                 360                 365

Thr His Tyr Asn Asn Gly Asn Tyr Thr Leu Ile Ala Lys Asn Pro Leu
    370                 375                 380

Gly Thr Ala Asn Gln Thr Ile Asn Gly His Phe Leu Lys Glu Pro Phe
385                 390                 395                 400

Pro Glu Ser Thr Asp Asn Phe Ile Leu Phe Asp Glu Val Ser Pro Thr
                405                 410                 415

Pro Pro Ile Thr Val Thr His Lys Pro Glu Glu Asp Thr Ala Ala Ala
            420                 425                 430

Asp Arg Lys Ile Pro Gln Pro Gln Lys Pro Gln Pro Gln Pro Gln
            435                 440                 445

Pro Gln Pro Lys Pro Gln Pro Lys Pro Glu Pro Glu Cys Thr Cys Pro
    450                 455                 460

Lys Cys Pro Ala Pro Glu Leu Pro Gly Gly Pro Ser Val Phe Val Phe
465                 470                 475                 480

Pro Pro Lys Pro Lys Asp Val Leu Ser Ile Ser Gly Arg Pro Glu Val
                485                 490                 495

Thr Cys Val Val Val Asp Val Gly Lys Lys Asp Pro Glu Val Asn Phe
            500                 505                 510

Asn Trp Tyr Val Asp Gly Val Glu Val Arg Thr Ala Asn Thr Lys Pro
            515                 520                 525

Lys Glu Glu Gln Phe Asn Ser Thr Tyr Arg Val Val Ser Val Leu Thr
            530                 535                 540

Ile Gln His Gln Asp Trp Leu Thr Gly Lys Glu Phe Lys Cys Lys Val
545                 550                 555                 560
```

```
Asn Asn Lys Ala Leu Pro Ala Pro Ile Glu Arg Thr Ile Ser Lys Ala
                565                 570                 575

Lys Gly Gln Thr Arg Glu Pro Gln Val Tyr Thr Leu Ala Pro His Arg
            580                 585                 590

Glu Glu Leu Ala Lys Asp Thr Val Ser Val Thr Cys Leu Val Lys Gly
        595                 600                 605

Phe Tyr Pro Pro Asp Ile Asn Val Glu Trp Gln Arg Asn Arg Gln Pro
    610                 615                 620

Glu Ser Glu Gly Ala Tyr Ala Thr Thr Leu Pro Gln Leu Asp Asn Asp
625                 630                 635                 640

Gly Thr Tyr Phe Leu Tyr Ser Lys Leu Ser Val Gly Lys Asn Thr Trp
                645                 650                 655

Gln Arg Gly Glu Thr Phe Thr Cys Val Val Met His Glu Ala Leu His
            660                 665                 670

Asn His Tyr Thr Gln Lys Ser Ile Thr Gln Ser Ser Gly Lys
        675                 680                 685

<210> SEQ ID NO 73
<211> LENGTH: 506
<212> TYPE: PRT
<213> ORGANISM: Artificial Sequence
<220> FEATURE:
<223> OTHER INFORMATION: human p75NTR-CamelFc

<400> SEQUENCE: 73

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
            35                  40                  45

Leu Gly Glu Gly Val Ala Gln Pro Cys Gly Ala Asn Gln Thr Val Cys
        50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Glu Gln Asp Leu Ile
210                 215                 220

Ala Ser Thr Val Ala Gly Val Val Thr Thr Val Met Gly Ser Ser Gln
225                 230                 235                 240
```

Pro Val Val Thr Arg Gly Thr Thr Asp Ala Ala Asp Arg Lys Ile
              245                 250                 255

Pro Gln Pro Gln Pro Lys Pro Gln Pro Gln Pro Gln Pro Gln Pro Lys
        260                 265                 270

Pro Gln Pro Lys Pro Glu Pro Glu Cys Thr Cys Pro Lys Cys Pro Ala
        275                 280                 285

Pro Glu Leu Pro Gly Gly Pro Ser Val Phe Val Phe Pro Pro Lys Pro
        290                 295                 300

Lys Asp Val Leu Ser Ile Ser Gly Arg Pro Glu Val Thr Cys Val Val
305                 310                 315                 320

Val Asp Val Gly Lys Lys Asp Pro Glu Val Asn Phe Asn Trp Tyr Val
                325                 330                 335

Asp Gly Val Glu Val Arg Thr Ala Asn Thr Lys Pro Lys Glu Glu Gln
                340                 345                 350

Phe Asn Ser Thr Tyr Arg Val Val Ser Val Leu Thr Ile Gln His Gln
            355                 360                 365

Asp Trp Leu Thr Gly Lys Glu Phe Lys Cys Lys Val Asn Asn Lys Ala
        370                 375                 380

Leu Pro Ala Pro Ile Glu Arg Thr Ile Ser Lys Ala Lys Gly Gln Thr
385                 390                 395                 400

Arg Glu Pro Gln Val Tyr Thr Leu Ala Pro His Arg Glu Glu Leu Ala
                405                 410                 415

Lys Asp Thr Val Ser Val Thr Cys Leu Val Lys Gly Phe Tyr Pro Pro
            420                 425                 430

Asp Ile Asn Val Glu Trp Gln Arg Asn Arg Gln Pro Glu Ser Glu Gly
        435                 440                 445

Ala Tyr Ala Thr Thr Leu Pro Gln Leu Asp Asn Asp Gly Thr Tyr Phe
    450                 455                 460

Leu Tyr Ser Lys Leu Ser Val Gly Lys Asn Thr Trp Gln Arg Gly Glu
465                 470                 475                 480

Thr Phe Thr Cys Val Val Met His Glu Ala Leu His Asn His Tyr Thr
                485                 490                 495

Gln Lys Ser Ile Thr Gln Ser Ser Gly Lys
            500                 505

<210> SEQ ID NO 74
<211> LENGTH: 670
<212> TYPE: PRT
<213> ORGANISM: Artificial Sequence
<220> FEATURE:
<223> OTHER INFORMATION: mouse TrkA-CamelFc

<400> SEQUENCE: 74

Met Leu Arg Gly Gln Arg Leu Gly Gln Leu Gly Trp His Arg Pro Ala
1               5                   10                  15

Ala Gly Leu Gly Ser Leu Met Thr Ser Leu Met Leu Ala Cys Ala Ser
                20                  25                  30

Ala Ala Ser Cys Arg Glu Val Cys Pro Val Gly Pro Ser Gly Leu
            35                  40                  45

Arg Cys Thr Arg Ala Gly Ser Leu Asp Thr Leu Arg Gly Leu Arg Gly
    50                  55                  60

Ala Gly Asn Leu Thr Glu Leu Tyr Val Glu Asn Gln His Leu Gln
65                  70                  75                  80

Arg Leu Glu Phe Glu Asp Leu Gln Gly Leu Gly Glu Leu Arg Ser Leu
                85                  90                  95

```
Thr Ile Val Lys Ser Gly Leu Arg Phe Val Ala Pro Asp Ala Phe Arg
            100                 105                 110

Phe Thr Pro Arg Leu Ser His Leu Asn Leu Ser Ser Asn Ala Leu Glu
        115                 120                 125

Ser Leu Ser Trp Lys Thr Val Gln Gly Leu Ser Leu Gln Asp Leu Thr
    130                 135                 140

Leu Ser Gly Asn Pro Leu His Cys Ser Cys Ala Leu Phe Trp Leu Gln
145                 150                 155                 160

Arg Trp Glu Gln Glu Gly Leu Cys Gly Val His Thr Gln Thr Leu His
                165                 170                 175

Asp Ser Gly Pro Gly Asp Gln Phe Leu Pro Leu Gly His Asn Thr Ser
            180                 185                 190

Cys Gly Val Pro Thr Val Lys Ile Gln Met Pro Asn Asp Ser Val Glu
        195                 200                 205

Val Gly Asp Asp Val Phe Leu Gln Cys Gln Val Glu Gly Leu Ala Leu
    210                 215                 220

Gln Gln Ala Asp Trp Ile Leu Thr Glu Leu Glu Gly Ala Ala Thr Val
225                 230                 235                 240

Lys Lys Phe Gly Asp Leu Pro Ser Leu Gly Leu Ile Leu Val Asn Val
                245                 250                 255

Thr Ser Asp Leu Asn Lys Lys Asn Val Thr Cys Trp Ala Glu Asn Asp
            260                 265                 270

Val Gly Arg Ala Glu Val Ser Val Gln Val Ser Val Ser Phe Pro Ala
        275                 280                 285

Ser Val His Leu Gly Leu Ala Val Glu Gln His His Trp Cys Ile Pro
    290                 295                 300

Phe Ser Val Asp Gly Gln Pro Ala Pro Ser Leu Arg Trp Leu Phe Asn
305                 310                 315                 320

Gly Ser Val Leu Asn Glu Thr Ser Phe Ile Phe Thr Gln Phe Leu Glu
                325                 330                 335

Ser Ala Leu Thr Asn Glu Thr Met Arg His Gly Cys Leu Arg Leu Asn
            340                 345                 350

Gln Pro Thr His Val Asn Asn Gly Asn Tyr Thr Leu Leu Ala Ala Asn
        355                 360                 365

Pro Tyr Gly Gln Ala Ala Ala Ser Val Met Ala Ala Phe Met Asp Asn
    370                 375                 380

Pro Phe Glu Phe Asn Pro Glu Asp Pro Ile Pro Val Ser Phe Ser Pro
385                 390                 395                 400

Val Asp Gly Asn Ser Thr Ser Arg Asp Pro Val Glu Lys Ala Ala Ala
                405                 410                 415

Asp Arg Lys Ile Pro Gln Pro Gln Pro Lys Pro Gln Pro Gln Pro Gln
            420                 425                 430

Pro Gln Pro Lys Pro Gln Pro Lys Pro Glu Pro Glu Cys Thr Cys Pro
        435                 440                 445

Lys Cys Pro Ala Pro Glu Leu Pro Gly Gly Pro Ser Val Phe Val Phe
    450                 455                 460

Pro Pro Lys Pro Lys Asp Val Leu Ser Ile Ser Gly Arg Pro Glu Val
465                 470                 475                 480

Thr Cys Val Val Val Asp Val Gly Lys Lys Asp Pro Glu Val Asn Phe
                485                 490                 495

Asn Trp Tyr Val Asp Gly Val Glu Val Arg Thr Ala Asn Thr Lys Pro
            500                 505                 510

Lys Glu Glu Gln Phe Asn Ser Thr Tyr Arg Val Val Ser Val Leu Thr
```

```
            515                 520                 525
Ile Gln His Gln Asp Trp Leu Thr Gly Lys Glu Phe Lys Cys Lys Val
530                 535                 540

Asn Asn Lys Ala Leu Pro Ala Pro Ile Glu Arg Thr Ile Ser Lys Ala
545                 550                 555                 560

Lys Gly Gln Thr Arg Glu Pro Gln Val Tyr Thr Leu Ala Pro His Arg
                565                 570                 575

Glu Glu Leu Ala Lys Asp Thr Val Ser Val Thr Cys Leu Val Lys Gly
            580                 585                 590

Phe Tyr Pro Pro Asp Ile Asn Val Glu Trp Gln Arg Asn Arg Gln Pro
            595                 600                 605

Glu Ser Glu Gly Ala Tyr Ala Thr Thr Leu Pro Gln Leu Asp Asn Asp
        610                 615                 620

Gly Thr Tyr Phe Leu Tyr Ser Lys Leu Ser Val Gly Lys Asn Thr Trp
625                 630                 635                 640

Gln Arg Gly Glu Thr Phe Thr Cys Val Val Met His Glu Ala Leu His
                645                 650                 655

Asn His Tyr Thr Gln Lys Ser Ile Thr Gln Ser Ser Gly Lys
            660                 665                 670

<210> SEQ ID NO 75
<211> LENGTH: 799
<212> TYPE: PRT
<213> ORGANISM: Mus musculus

<400> SEQUENCE: 75

Met Leu Arg Gly Gln Arg Leu Gly Gln Leu Gly Trp His Arg Pro Ala
1               5                   10                  15

Ala Gly Leu Gly Ser Leu Met Thr Ser Leu Met Leu Ala Cys Ala Ser
            20                  25                  30

Ala Ala Ser Cys Arg Glu Val Cys Cys Pro Val Gly Pro Ser Gly Leu
        35                  40                  45

Arg Cys Thr Arg Ala Gly Ser Leu Asp Thr Leu Arg Gly Leu Arg Gly
    50                  55                  60

Ala Gly Asn Leu Thr Glu Leu Tyr Val Glu Asn Gln Gln His Leu Gln
65                  70                  75                  80

Arg Leu Glu Phe Glu Asp Leu Gln Gly Leu Gly Glu Leu Arg Ser Leu
                85                  90                  95

Thr Ile Val Lys Ser Gly Leu Arg Phe Val Ala Pro Asp Ala Phe Arg
            100                 105                 110

Phe Thr Pro Arg Leu Ser His Leu Asn Leu Ser Ser Asn Ala Leu Glu
        115                 120                 125

Ser Leu Ser Trp Lys Thr Val Gln Gly Leu Ser Leu Gln Asp Leu Thr
    130                 135                 140

Leu Ser Gly Asn Pro Leu His Cys Ser Cys Ala Leu Phe Trp Leu Gln
145                 150                 155                 160

Arg Trp Glu Gln Glu Gly Leu Cys Gly Val His Thr Gln Thr Leu His
                165                 170                 175

Asp Ser Gly Pro Gly Asp Gln Phe Leu Pro Leu Gly His Asn Thr Ser
            180                 185                 190

Cys Gly Val Pro Thr Val Lys Ile Gln Met Pro Asn Asp Ser Val Glu
        195                 200                 205

Val Gly Asp Asp Val Phe Leu Gln Cys Gln Val Glu Gly Leu Ala Leu
    210                 215                 220
```

```
Gln Gln Ala Asp Trp Ile Leu Thr Glu Leu Glu Gly Ala Ala Thr Val
225                 230                 235                 240

Lys Lys Phe Gly Asp Leu Pro Ser Leu Gly Leu Ile Leu Val Asn Val
            245                 250                 255

Thr Ser Asp Leu Asn Lys Lys Asn Val Thr Cys Trp Ala Glu Asn Asp
        260                 265                 270

Val Gly Arg Ala Glu Val Ser Val Gln Val Ser Val Ser Phe Pro Ala
    275                 280                 285

Ser Val His Leu Gly Leu Ala Val Glu Gln His His Trp Cys Ile Pro
        290                 295                 300

Phe Ser Val Asp Gly Gln Pro Ala Pro Ser Leu Arg Trp Leu Phe Asn
305                 310                 315                 320

Gly Ser Val Leu Asn Glu Thr Ser Phe Ile Phe Thr Gln Phe Leu Glu
            325                 330                 335

Ser Ala Leu Thr Asn Glu Thr Met Arg His Gly Cys Leu Arg Leu Asn
            340                 345                 350

Gln Pro Thr His Val Asn Asn Gly Asn Tyr Thr Leu Leu Ala Ala Asn
            355                 360                 365

Pro Tyr Gly Gln Ala Ala Ala Ser Val Met Ala Ala Phe Met Asp Asn
    370                 375                 380

Pro Phe Glu Phe Asn Pro Glu Asp Pro Ile Pro Val Ser Phe Ser Pro
385                 390                 395                 400

Val Asp Gly Asn Ser Thr Ser Arg Asp Pro Val Glu Lys Lys Asp Glu
                405                 410                 415

Thr Pro Phe Gly Val Ser Val Ala Val Gly Leu Ala Val Ser Ala Ala
            420                 425                 430

Leu Phe Leu Ser Ala Leu Leu Leu Val Leu Asn Lys Cys Gly Gln Arg
            435                 440                 445

Ser Lys Phe Gly Ile Asn Arg Pro Ala Val Leu Ala Pro Glu Asp Gly
    450                 455                 460

Leu Ala Met Ser Leu His Phe Met Thr Leu Gly Gly Ser Ser Leu Ser
465                 470                 475                 480

Pro Thr Glu Gly Lys Gly Ser Gly Leu Gln Gly His Ile Met Glu Asn
            485                 490                 495

Pro Gln Tyr Phe Ser Asp Thr Cys Val His His Ile Lys Arg Gln Asp
        500                 505                 510

Ile Ile Leu Lys Trp Glu Leu Gly Glu Gly Ala Phe Gly Lys Val Phe
            515                 520                 525

Leu Ala Glu Cys Tyr Asn Leu Leu Asn Asp Gln Asp Lys Met Leu Val
    530                 535                 540

Ala Val Lys Ala Leu Lys Glu Ala Ser Glu Asn Ala Arg Gln Asp Phe
545                 550                 555                 560

Gln Arg Glu Ala Glu Leu Leu Thr Met Leu Gln His Gln His Ile Val
            565                 570                 575

Arg Phe Phe Gly Val Cys Thr Glu Gly Gly Pro Leu Leu Met Val Phe
            580                 585                 590

Glu Tyr Met Arg His Gly Asp Leu Asn Arg Phe Leu Arg Ser His Gly
        595                 600                 605

Pro Asp Ala Lys Leu Leu Ala Gly Gly Glu Asp Val Ala Pro Gly Pro
    610                 615                 620

Leu Gly Leu Gly Gln Leu Leu Ala Val Ala Ser Gln Val Ala Ala Gly
625                 630                 635                 640

Met Val Tyr Leu Ala Ser Leu His Phe Val His Arg Asp Leu Ala Thr
```

```
                 645                 650                 655
Arg Asn Cys Leu Val Gly Gln Gly Leu Val Val Lys Ile Gly Asp Phe
            660                 665                 670

Gly Met Ser Arg Asp Ile Tyr Ser Thr Asp Tyr Tyr Arg Val Gly Gly
            675                 680                 685

Arg Thr Met Leu Pro Ile Arg Trp Met Pro Pro Glu Ser Ile Leu Tyr
            690                 695                 700

Arg Lys Phe Ser Thr Glu Ser Asp Val Trp Ser Phe Gly Val Val Leu
705                 710                 715                 720

Trp Glu Ile Phe Thr Tyr Gly Lys Gln Pro Trp Tyr Gln Leu Ser Asn
                725                 730                 735

Thr Glu Ala Ile Glu Cys Ile Thr Gln Gly Arg Glu Leu Glu Arg Pro
            740                 745                 750

Arg Ala Cys Pro Pro Asp Val Tyr Ala Ile Met Arg Gly Cys Trp Gln
            755                 760                 765

Arg Glu Pro Gln Gln Arg Leu Ser Met Lys Val His Ala Arg Leu
            770                 775                 780

Gln Ala Leu Ala Gln Ala Pro Pro Ser Tyr Leu Asp Val Leu Gly
785                 790                 795

<210> SEQ ID NO 76
<211> LENGTH: 799
<212> TYPE: PRT
<213> ORGANISM: Rattus rattus

<400> SEQUENCE: 76

Met Leu Arg Gly Gln Arg His Gly Gln Leu Gly Trp His Arg Pro Ala
1               5                   10                  15

Ala Gly Leu Gly Gly Leu Val Thr Ser Leu Met Leu Ala Cys Ala Cys
            20                  25                  30

Ala Ala Ser Cys Arg Glu Thr Cys Cys Pro Val Gly Pro Ser Gly Leu
        35                  40                  45

Arg Cys Thr Arg Ala Gly Thr Leu Asn Thr Leu Arg Gly Leu Arg Gly
    50                  55                  60

Ala Gly Asn Leu Thr Glu Leu Tyr Val Glu Asn Gln Arg Asp Leu Gln
65                  70                  75                  80

Arg Leu Glu Phe Glu Asp Leu Gln Gly Leu Gly Glu Leu Arg Ser Leu
                85                  90                  95

Thr Ile Val Lys Ser Gly Leu Arg Phe Val Ala Pro Asp Ala Phe His
            100                 105                 110

Phe Thr Pro Arg Leu Ser His Leu Asn Leu Ser Ser Asn Ala Leu Glu
        115                 120                 125

Ser Leu Ser Trp Lys Thr Val Gln Gly Leu Ser Leu Gln Asp Leu Thr
    130                 135                 140

Leu Ser Gly Asn Pro Leu His Cys Ser Cys Ala Leu Leu Trp Leu Gln
145                 150                 155                 160

Arg Trp Glu Gln Glu Asp Leu Cys Gly Val Tyr Thr Gln Lys Leu Gln
                165                 170                 175

Gly Ser Gly Ser Gly Asp Gln Phe Leu Pro Leu Gly His Asn Asn Ser
            180                 185                 190

Cys Gly Val Pro Ser Val Lys Ile Gln Met Pro Asn Asp Ser Val Glu
        195                 200                 205

Val Gly Asp Asp Val Phe Leu Gln Cys Gln Val Glu Gly Gln Ala Leu
    210                 215                 220
```

Gln Gln Ala Asp Trp Ile Leu Thr Glu Leu Glu Gly Thr Ala Thr Met
225                 230                 235                 240

Lys Lys Ser Gly Asp Leu Pro Ser Leu Gly Leu Thr Leu Val Asn Val
            245                 250                 255

Thr Ser Asp Leu Asn Lys Lys Asn Val Thr Cys Trp Ala Glu Asn Asp
        260                 265                 270

Val Gly Arg Ala Glu Val Ser Val Gln Val Ser Val Ser Phe Pro Ala
    275                 280                 285

Ser Val His Leu Gly Lys Ala Val Glu Gln His His Trp Cys Ile Pro
        290                 295                 300

Phe Ser Val Asp Gly Gln Pro Ala Pro Ser Leu Arg Trp Phe Phe Asn
305                 310                 315                 320

Gly Ser Val Leu Asn Glu Thr Ser Phe Ile Phe Thr Gln Phe Leu Glu
            325                 330                 335

Ser Ala Leu Thr Asn Glu Thr Met Arg His Gly Cys Leu Arg Leu Asn
            340                 345                 350

Gln Pro Thr His Val Asn Asn Gly Asn Tyr Thr Leu Leu Ala Ala Asn
            355                 360                 365

Pro Tyr Gly Gln Ala Ala Ala Ser Ile Met Ala Ala Phe Met Asp Asn
    370                 375                 380

Pro Phe Glu Phe Asn Pro Glu Asp Pro Ile Pro Val Ser Phe Ser Pro
385                 390                 395                 400

Val Asp Thr Asn Ser Thr Ser Arg Asp Pro Val Glu Lys Lys Asp Glu
                405                 410                 415

Thr Pro Phe Gly Val Ser Val Ala Val Gly Leu Ala Val Ser Ala Ala
            420                 425                 430

Leu Phe Leu Ser Ala Leu Leu Leu Val Leu Asn Lys Cys Gly Gln Arg
        435                 440                 445

Ser Lys Phe Gly Ile Asn Arg Pro Ala Val Leu Ala Pro Glu Asp Gly
        450                 455                 460

Leu Ala Met Ser Leu His Phe Met Thr Leu Gly Gly Ser Ser Leu Ser
465                 470                 475                 480

Pro Thr Glu Gly Lys Gly Ser Gly Leu Gln Gly His Ile Met Glu Asn
            485                 490                 495

Pro Gln Tyr Phe Ser Asp Thr Cys Val His His Ile Lys Arg Gln Asp
            500                 505                 510

Ile Ile Leu Lys Trp Glu Leu Gly Glu Gly Ala Phe Gly Lys Val Phe
        515                 520                 525

Leu Ala Glu Cys Tyr Asn Leu Leu Asn Asp Gln Asp Lys Met Leu Val
    530                 535                 540

Ala Val Lys Ala Leu Lys Glu Thr Ser Glu Asn Ala Arg Gln Asp Phe
545                 550                 555                 560

His Arg Glu Ala Glu Leu Leu Thr Met Leu Gln His Gln His Ile Val
            565                 570                 575

Arg Phe Phe Gly Val Cys Thr Glu Gly Gly Pro Leu Leu Met Val Phe
            580                 585                 590

Glu Tyr Met Arg His Gly Asp Leu Asn Arg Phe Leu Arg Ser His Gly
        595                 600                 605

Pro Asp Ala Lys Leu Leu Ala Gly Gly Glu Asp Val Ala Pro Gly Pro
    610                 615                 620

Leu Gly Leu Gly Gln Leu Leu Ala Val Ala Ser Gln Val Ala Ala Gly
625                 630                 635                 640

Met Val Tyr Leu Ala Ser Leu His Phe Val His Arg Asp Leu Ala Thr

```
                        645                 650                 655
Arg Asn Cys Leu Val Gly Gln Gly Leu Val Val Lys Ile Gly Asp Phe
            660                 665                 670

Gly Met Ser Arg Asp Ile Tyr Ser Thr Asp Tyr Tyr Arg Val Gly Gly
            675                 680                 685

Arg Thr Met Leu Pro Ile Arg Trp Met Pro Pro Glu Ser Ile Leu Tyr
            690                 695                 700

Arg Lys Phe Ser Thr Glu Ser Asp Val Trp Ser Phe Gly Val Val Leu
705                 710                 715                 720

Trp Glu Ile Phe Thr Tyr Gly Lys Gln Pro Trp Tyr Gln Leu Ser Asn
                725                 730                 735

Thr Glu Ala Ile Glu Cys Ile Thr Gln Gly Arg Glu Leu Glu Arg Pro
            740                 745                 750

Arg Ala Cys Pro Pro Asp Val Tyr Ala Ile Met Arg Gly Cys Trp Gln
            755                 760                 765

Arg Glu Pro Gln Gln Arg Leu Ser Met Lys Val His Ala Arg Leu
            770                 775                 780

Gln Ala Leu Ala Gln Ala Pro Pro Ser Tyr Leu Asp Val Leu Gly
785                 790                 795

<210> SEQ ID NO 77
<211> LENGTH: 830
<212> TYPE: PRT
<213> ORGANISM: Macaca mulatta

<400> SEQUENCE: 77

Met Ser Ala Glu Ala Trp Gln Gln Gln Leu Arg Ala His Arg Arg Leu
1               5                   10                  15

Pro Arg Arg Ser Lys Ala Gly Ala Ala Ala Met Leu Arg Gly Gly Arg
            20                  25                  30

Arg Gly Gln Leu Gly Trp His Ser Trp Ala Ala Gly Pro Gly Ser Leu
            35                  40                  45

Leu Ala Trp Leu Met Leu Ala Ser Ala Gly Ala Ser Pro Cys Pro Asp
    50                  55                  60

Ala Cys Cys Pro His Gly Ser Ser Gly Leu Arg Cys Thr Arg Asp Gly
65                  70                  75                  80

Ala Leu Asp Ser Leu His His Leu Pro Gly Ala Glu Asn Leu Thr Glu
                85                  90                  95

Leu Val Gln Gly Ser Trp Ala Ala Gly Phe Arg Glu Ile Glu Gly Arg
            100                 105                 110

Ile Ser Gly His Gln Gly Lys Gly Gln Ala Ser Pro His Pro Leu Pro
            115                 120                 125

Cys Tyr Glu Glu Ala Thr Pro Ala Phe Leu Leu Glu Leu Gly Ile Glu
    130                 135                 140

Leu Ala Gly Ile Gly Gly Arg Cys Tyr Ile Glu Asn Gln Gln His Leu
145                 150                 155                 160

Gln His Leu Glu Leu Arg Asp Leu Arg Gly Leu Gly Glu Leu Arg Asn
                165                 170                 175

Leu Val Leu Ser Gly Asn Pro Leu His Cys Ser Cys Ala Leu Arg Trp
            180                 185                 190

Leu Gln Arg Trp Glu Glu Glu Gly Leu Gly Gly Val His Glu Gln Lys
            195                 200                 205

Leu Gln Cys His Gly Gln Gly Pro Leu Ala His Met Pro Asn Ala Ser
    210                 215                 220
```

```
Cys Gly Val Pro Met Leu Lys Val Gln Val Pro Asn Ala Ser Val Asp
225                 230                 235                 240

Val Gly Asp Asp Val Leu Leu Trp Cys Gln Val Glu Gly Arg Gly Leu
            245                 250                 255

Glu Gln Ala Gly Trp Ile Leu Thr Glu Leu Glu Gln Ser Ala Thr Val
        260                 265                 270

Met Lys Ser Gly Ala Leu Pro Ser Leu Gly Leu Thr Leu Ala Asn Val
    275                 280                 285

Thr Ser Asp Leu Asn Arg Lys Asn Val Thr Cys Trp Ala Glu Asn Asp
290                 295                 300

Val Gly Arg Ala Glu Leu Ser Val Gln Val Asn Val Ser Phe Pro Ala
305                 310                 315                 320

Ser Val Gln Leu His Thr Ala Val Glu Met His His Trp Cys Ile Pro
            325                 330                 335

Phe Ser Val Asp Gly Gln Pro Ala Pro Ser Leu Arg Trp Leu Phe Asn
            340                 345                 350

Gly Ser Val Leu Asn Glu Thr Ser Phe Ile Phe Thr Glu Phe Leu Glu
        355                 360                 365

Pro Ala Ala Asn Glu Thr Val Arg His Gly Cys Leu Arg Leu Asn Gln
370                 375                 380

Pro Thr His Val Asn Asn Gly Asn Tyr Thr Leu Leu Ala Ala Asn Pro
385                 390                 395                 400

Phe Gly Gln Ala Ser Ala Ser Ile Met Ala Ala Phe Met Asp Asn Pro
            405                 410                 415

Phe Glu Phe Asn Pro Glu Asp Pro Ile Pro Val Ser Phe Ser Pro Val
            420                 425                 430

Asp Thr Asn Ser Thr Ser Gly Asp Pro Val Glu Lys Lys Asp Glu Thr
            435                 440                 445

Pro Phe Gly Val Ser Val Ala Val Gly Leu Ala Val Phe Ala Cys Leu
450                 455                 460

Phe Leu Ser Met Leu Leu Leu Val Leu Asn Lys Cys Gly Arg Arg Asn
465                 470                 475                 480

Lys Phe Gly Ile Asn Arg Pro Ala Val Leu Ala Pro Glu Asp Gly Leu
            485                 490                 495

Ala Met Ser Leu His Phe Met Thr Leu Gly Gly Ser Ser Leu Ser Pro
        500                 505                 510

Thr Glu Gly Lys Gly Ser Gly Leu Gln Gly His Ile Ile Glu Asn Pro
        515                 520                 525

Gln Tyr Phe Ser Asp Ala Cys Val His His Ile Lys Arg Arg Asp Ile
        530                 535                 540

Val Leu Lys Trp Glu Leu Gly Glu Gly Ala Phe Gly Lys Val Phe Leu
545                 550                 555                 560

Ala Glu Cys His Asn Leu Leu Pro Glu Gln Asp Lys Met Leu Val Ala
            565                 570                 575

Val Lys Ala Leu Lys Glu Val Ser Glu Ser Ala Arg Gln Asp Phe Gln
            580                 585                 590

Arg Glu Ala Glu Leu Leu Thr Met Leu Gln His Gln His Ile Val Arg
        595                 600                 605

Phe Phe Gly Val Cys Thr Glu Gly Arg Pro Leu Leu Met Val Phe Glu
        610                 615                 620

Tyr Met Arg His Gly Asp Leu Asn Arg Phe Leu Arg Ser His Gly Pro
625                 630                 635                 640

Asp Ala Lys Leu Leu Ala Gly Gly Glu Asp Val Ala Pro Gly Pro Leu
```

645                 650                 655

Gly Leu Gly Gln Leu Leu Ala Val Ala Ser Gln Val Ala Ala Gly Met
                660                 665                 670

Val Tyr Leu Ala Gly Leu His Phe Val His Arg Asp Leu Ala Thr Arg
            675                 680                 685

Asn Cys Leu Val Gly Gln Gly Leu Val Val Lys Ile Gly Asp Phe Gly
        690                 695                 700

Met Ser Arg Asp Ile Tyr Ser Thr Asp Tyr Tyr Arg Val Gly Gly Arg
705                 710                 715                 720

Thr Met Leu Pro Ile Arg Trp Met Pro Glu Ser Ile Leu Tyr Arg
                725                 730                 735

Lys Phe Thr Thr Glu Ser Asp Val Trp Ser Phe Gly Val Val Leu Trp
                740                 745                 750

Glu Ile Phe Thr Tyr Gly Lys Gln Pro Trp Tyr Gln Leu Ser Asn Thr
            755                 760                 765

Glu Ala Ile Asp Cys Ile Thr Gln Gly Arg Glu Leu Glu Arg Pro Arg
        770                 775                 780

Ala Cys Pro Pro Glu Val Tyr Ala Ile Met Arg Gly Cys Trp Gln Arg
785                 790                 795                 800

Glu Pro Gln Gln Arg His Ser Ile Lys Asp Val His Ala Arg Leu Gln
                805                 810                 815

Ala Leu Ala Gln Ala Pro Pro Val Tyr Leu Asp Val Leu Gly
                820                 825                 830

<210> SEQ ID NO 78
<211> LENGTH: 216
<212> TYPE: PRT
<213> ORGANISM: Artificial Sequence
<220> FEATURE:
<223> OTHER INFORMATION: human Ig1,2 TrkA

<400> SEQUENCE: 78

Met Ala Cys Gly Val Pro Thr Leu Lys Val Gln Val Pro Asn Ala Ser
1               5                   10                  15

Val Asp Val Gly Asp Asp Val Leu Leu Arg Cys Gln Val Glu Gly Arg
                20                  25                  30

Gly Leu Glu Gln Ala Gly Trp Ile Leu Thr Glu Leu Glu Gln Ser Ala
            35                  40                  45

Thr Val Met Lys Ser Gly Gly Leu Pro Ser Leu Gly Leu Thr Leu Ala
        50                  55                  60

Asn Val Thr Ser Asp Leu Asn Arg Lys Asn Leu Thr Cys Trp Ala Glu
65                  70                  75                  80

Asn Asp Val Gly Arg Ala Glu Val Ser Val Gln Val Asn Val Ser Phe
                85                  90                  95

Pro Ala Ser Val Gln Leu His Thr Ala Val Glu Met His His Trp Cys
                100                 105                 110

Ile Pro Phe Ser Val Asp Gly Gln Pro Ala Pro Ser Leu Arg Trp Leu
            115                 120                 125

Phe Asn Gly Ser Val Leu Asn Glu Thr Ser Phe Ile Phe Thr Glu Phe
        130                 135                 140

Leu Glu Pro Ala Ala Asn Glu Thr Val Arg His Gly Cys Leu Arg Leu
145                 150                 155                 160

Asn Gln Pro Thr His Val Asn Asn Gly Asn Tyr Thr Leu Leu Ala Ala
                165                 170                 175

Asn Pro Phe Gly Gln Gly Ser Ala Ser Ile Met Ala Ala Phe Met Asp

```
                180             185             190
Asn Pro Phe Glu Phe Asn Pro Glu Asp Pro Ile Pro Asp Asn Asn Thr
            195                 200             205

His Leu Glu Thr Arg Trp Arg Arg
    210                 215

<210> SEQ ID NO 79
<211> LENGTH: 223
<212> TYPE: PRT
<213> ORGANISM: Artificial Sequence
<220> FEATURE:
<223> OTHER INFORMATION: mouse Ig1,2 TrkA

<400> SEQUENCE: 79

Met Ala Cys Gly Val Pro Thr Val Lys Ile Gln Met Pro Asn Asp Ser
1               5                   10                  15

Val Glu Val Gly Asp Asp Val Phe Leu Gln Cys Gln Val Glu Gly Leu
            20                  25                  30

Ala Leu Gln Gln Ala Asp Trp Ile Leu Thr Glu Leu Glu Gly Ala Ala
        35                  40                  45

Thr Val Lys Lys Phe Gly Asp Leu Pro Ser Leu Gly Leu Ile Leu Val
    50                  55                  60

Asn Val Thr Ser Asp Leu Asn Lys Lys Asn Val Thr Cys Trp Ala Glu
65                  70                  75                  80

Asn Asp Val Gly Arg Ala Glu Val Ser Val Gln Val Ser Val Ser Phe
                85                  90                  95

Pro Ala Ser Val His Leu Gly Leu Ala Val Glu Gln His His Trp Cys
            100                 105                 110

Ile Pro Phe Ser Val Asp Gly Gln Pro Ala Pro Ser Leu Arg Trp Leu
        115                 120                 125

Phe Asn Gly Ser Val Leu Asn Glu Thr Ser Phe Ile Phe Thr Gln Phe
    130                 135                 140

Leu Glu Ser Ala Leu Thr Asn Glu Thr Met Arg His Gly Cys Leu Arg
145                 150                 155                 160

Leu Asn Gln Pro Thr His Val Asn Asn Gly Asn Tyr Thr Leu Leu Ala
                165                 170                 175

Ala Asn Pro Tyr Gly Gln Ala Ala Ser Val Met Ala Ala Phe Met
            180                 185                 190

Asp Asn Pro Phe Glu Phe Asn Pro Glu Asp Pro Ile Pro Val Ser Phe
        195                 200                 205

Ser Pro Val Asp Gly Asn Ser Thr Ser Arg Asp Pro Val Glu Lys
    210                 215                 220

<210> SEQ ID NO 80
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 80
catcatgaat tcctaataga agtggaaaag cctctgtacg gagtagaggt g         51

<210> SEQ ID NO 81
<211> LENGTH: 63
<212> TYPE: DNA
<213> ORGANISM: Artificial Sequence
<220> FEATURE:
<223> OTHER INFORMATION: synthetic oligonucleotide
```

<400> SEQUENCE: 81
cacagaaagt tcaatttcaa agtgggctgt ttcaccaaca aacacctcta ctccgtacag    60
agg                                                                 63

<210> SEQ ID NO 82
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 82
ccactttgaa attgaacttt ctgtggagat gcaccactgg gttcacggcc agtggaagct    60
g                                                                   61

<210> SEQ ID NO 83
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 83
caatgatttc acagtcaggg gaagctgtca aaggctgtcc tttcagcttc cactggccgt    60

<210> SEQ ID NO 84
<211> LENGTH: 66
<212> TYPE: DNA
<213> ORGANISM: Artificial Sequence
<220> FEATURE:
<223> OTHER INFORMATION: synthetic oligonucleotide

<400> SEQUENCE: 84
cttcccctga ctgtgaaatc attgaggatg gaaagaagca tattctgatc cttcataact    60
gtcagc                                                              66

<210> SEQ ID NO 85
<211> LENGTH: 63
<212> TYPE: DNA
<213> ORGANISM: Artificial Sequence
<220> FEATURE:
<223> OTHER INFORMATION: synthetic oligonucleotide

<400> SEQUENCE: 85
tctccacctg gaaggaaacc tctcctgtca tacccagctg acagttatga aggatcagaa    60
tat                                                                 63

<210> SEQ ID NO 86
<211> LENGTH: 63
<212> TYPE: DNA
<213> ORGANISM: Artificial Sequence
<220> FEATURE:
<223> OTHER INFORMATION: synthetic oligonucleotide

<400> SEQUENCE: 86
ggtttccttc caggtggaga tgcaccactg gaaatctgca gccaatctga aagtgaaaga    60
att                                                                 63

<210> SEQ ID NO 87
<211> LENGTH: 58
<212> TYPE: DNA

```
<213> ORGANISM: Artificial Sequence
<220> FEATURE:
<223> OTHER INFORMATION: synthetic oligonucleotide

<400> SEQUENCE: 87
taatacgact cactatagtc gacggatcct tacaattctt tcactttcag attggctg         58

<210> SEQ ID NO 88
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 88
catcatgaat tcctaataga agtggaaaag                                         30

<210> SEQ ID NO 89
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 89
taatacgact cactatagtc gacgg                                              25

<210> SEQ ID NO 90
<211> LENGTH: 1410
<212> TYPE: DNA
<213> ORGANISM: Artificial Sequence
<220> FEATURE:
<223> OTHER INFORMATION: CRB0089 IgG4 derived VH-CH1-H-CH2-CH3

<400> SEQUENCE: 90
atggaatggt ccggcgtgtt catgttcctg ctgtccgtga ccgctggcgt gcactcccag        60
gtgcagctgc aggaatccgg ccctggcctg gtgaaaccct cccagaccct gtccctgacc       120
tgcgccatct ccggcgactc cgtgtcctcc aactccgccg cctggaactg gatccggcag       180
tccccttctc ggggcctgga atggctgggc agaaccttcc atcggtccag atggtacaac       240
gagtaccccg tgtccgtgcg gtcccggatc accatcaacc ccgacacctc caacaaccag       300
ttcaccctgc agctgaactc cgtgaccccc gacgacaccg ccgtgtacta ctgcgccaga       360
gcccctgtgg ccggcctgac cttcgatatc tggggccagg gcacaatggt gacagtgtcc       420
tccgcctcca ccaagggccc ctctgtgttc cctctggccc cttgctcccg gtccacctct       480
gagtctaccg ccgctctggg ctgtctggtg aaagactact ccccgagcc cgtgaccgtg       540 tcctggaata gtggcgccct gacctccggc gtgcacacct tccagccgt gctgcagtcc       600 tccggcctgt actccctgtc ctccgtggtg accgtgccct cctccagcct gggcaccaag       660
acctacacct gtaacgtgga ccacaagccc tccaacacca aggtggacaa gcgggtggaa       720
tctaagtacg gccctccctg cccaccctgt cctgctccag agtttctggg cggaccctcc       780
gtgttcctgt tccccccaaa gcccaaggac accctgatga tctcccggac ccccgaagtg       840
acctgcgtgg tggtggacgt gtcccaggaa gatcccgagg tccagttcaa ttggtacgtg       900
gacggcgtgg aagtgcacaa cgccaagacc aagcccagag aggaacagtt caactccacc       960
taccgggtgg tgtctgtgct gaccgtgctg caccaggact ggctgaacgg caaagagtac      1020
aagtgcaagg tctccaacaa gggcctgccc tccagcatcg aaaagaccat ctccaaggcc      1080
aagggccagc ccgcgagcc tcaggtgtac acactgcccc ctagccaaga agagatgacc      1140
```

```
aagaaccagg tgtccctgac atgcctggtg aagggcttct acccctccga tatcgccgtg    1200
gaatgggagt ccaacggcca gcccgagaac aactacaaga ccaccccccc tgtgctggac    1260
tccgacggct ccttcttcct gtactctcgg ctgaccgtgg acaagtcccg gtggcaggaa    1320
ggcaacgtct ctcctgctc cgtgatgcac gaggccctgc acaaccacta cacccagaag    1380
tctctgagcc tgtccctggg caagtgatga                                     1410

<210> SEQ ID NO 91
<211> LENGTH: 696
<212> TYPE: DNA
<213> ORGANISM: Artificial Sequence
<220> FEATURE:
<223> OTHER INFORMATION: CRB0089_VLCL

<400> SEQUENCE: 91
atggaatggt ccggcgtgtt catgttcctg ctgtccgtga ccgctggcgt gcactcccag     60
accgtggtga cacaggaacc ctccgtctct ggcgcccctg ccagagagt gaccatctcc    120 tgcaccggct cctccagcat catcggcgct ggctacgagg tgcactggta tcagcatctg    180
cccggcaccg cccccaagct gctgatctac gactccatca accggccctc cggcgtgccc    240
gaccggttct ctggctccaa gtccggcacc tccgcctccc tggctatcac cggactgcag    300
gccgaggacg aggccgacta ctactgccag tcctccgcca tcttcggcgg aggcaccaag    360
ctgaccgtgc tgggccagcc caaggccaac cccaccgtga ccctgttccc cccatcctcc    420
gaggaactgc aggccaacaa ggccacccctg gtctgcctga tctccgactt ctaccctggc    480
gccgtgaccg tggcctggaa ggctgacggc tctcctgtga aggccggcgt ggaaaccacc    540
aagccctcca gcagtccaa caacaaatac gccgcctcct cctacctgtc cctgaccccc    600
gagcagtgga agtcccaccg gtcctacagc tgccaggtca cacacgaggg ctccaccgtg    660
gaaaagaccg tggctcctac cgagtgctcc tgatga                              696

<210> SEQ ID NO 92
<211> LENGTH: 89
<212> TYPE: PRT
<213> ORGANISM: Artificial Sequence
<220> FEATURE:
<223> OTHER INFORMATION: I27 Ig-like domain of titin protein

<400> SEQUENCE: 92

Leu Ile Glu Val Glu Lys Pro Leu Tyr Gly Val Glu Val Phe Val Gly
1               5                   10                  15

Glu Thr Ala His Phe Glu Ile Glu Leu Ser Glu Pro Asp Val His Gly
                20                  25                  30

Gln Trp Lys Leu Lys Gly Gln Pro Leu Thr Ala Ser Pro Asp Cys Glu
            35                  40                  45

Ile Ile Glu Asp Gly Lys Lys His Ile Leu Ile Leu His Asn Cys Gln
        50                  55                  60

Leu Gly Met Thr Gly Glu Val Ser Phe Gln Ala Ala Asn Ala Lys Ser
65                  70                  75                  80

Ala Ala Asn Leu Lys Val Lys Glu Leu
                85

<210> SEQ ID NO 93
<211> LENGTH: 20
<212> TYPE: PRT
<213> ORGANISM: Artificial Sequence
<220> FEATURE:
```

<223> OTHER INFORMATION: peptide linker

<400> SEQUENCE: 93

Ser Gly Gly Ser Thr Ser Gly Ser Gly Lys Pro Gly Ser Gly Glu Gly
1               5                   10                  15

Ser Ser Gly Thr
            20

<210> SEQ ID NO 94
<211> LENGTH: 247
<212> TYPE: PRT
<213> ORGANISM: Artificial Sequence
<220> FEATURE:
<223> OTHER INFORMATION: CRB0022 scFv

<400> SEQUENCE: 94

Asp Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Arg Thr Arg Leu Glu Ile Lys Pro Ser Gly Gly Ser Thr
            100                 105                 110

Ser Gly Ser Gly Lys Pro Gly Ser Gly Glu Asp Ser Ser Gly Ala Gln
        115                 120                 125

Val Gln Leu Gln Gln Ser Gly Ala Glu Leu Val Lys Pro Gly Ala Ser
    130                 135                 140

Val Glu Leu Ser Cys Thr Ala Ser Gly Phe Asn Ile Lys Asp Thr Tyr
145                 150                 155                 160

Met His Trp Val Lys Gln Arg Pro Glu Gln Gly Leu Glu Trp Ile Gly
                165                 170                 175

Gly Ile Asp Pro Ala Asn Gly Asn Thr Ile Tyr Val Pro Lys Phe Gln
            180                 185                 190

Gly Lys Ala Thr Ile Thr Ala Asp Thr Ser Ser Asn Thr Ala Tyr Leu
        195                 200                 205

Gln Leu Ser Ser Leu Thr Ser Glu Asp Thr Ala Val Tyr Tyr Cys Ala
    210                 215                 220

Arg Gly Gly Tyr Asp Phe Asp Tyr Ala Met Asp Tyr Trp Gly Gln Gly
225                 230                 235                 240

Thr Ser Val Thr Val Ser Ser
                245

<210> SEQ ID NO 95
<211> LENGTH: 249
<212> TYPE: PRT
<213> ORGANISM: Artificial Sequence
<220> FEATURE:
<223> OTHER INFORMATION: CRB0036 scFv

<400> SEQUENCE: 95

Asp Ile Val Met Thr Gln Ala Ala Pro Ser Val Pro Val Thr Pro Gly

```
          1               5                  10                 15
        Glu Ser Val Ser Ile Ser Cys Arg Ser Ser Lys Ser Leu Leu His Ser
                        20                  25                  30

Ser Gly Ile Thr Ser Leu Tyr Trp Tyr Leu Gln Arg Pro Gly Gln Ser
                    35                  40                  45

Pro Gln Leu Pro Ile Tyr Arg Met Ser Ser Leu Ala Ser Gly Val Pro
                50                  55                  60

Asp Arg Phe Ser Val Ser Gly Ser Gly Thr Ala Phe Thr Leu Arg Ile
         65                  70                  75                  80

Ser Arg Val Glu Ala Glu Asp Val Gly Val Tyr Tyr Cys Met Gln His
                            85                  90                  95

Leu Glu Tyr Pro Leu Thr Phe Gly Ala Gly Thr Lys Leu Glu Leu Lys
                        100                 105                 110

Arg Ser Gly Gly Ser Thr Ser Gly Ser Gly Lys Pro Gly Ser Gly Glu
                    115                 120                 125

Gly Ser Ser Gly Thr Gln Val Gln Leu Gln Gln Ser Gly Ala Glu Leu
                130                 135                 140

Leu Lys Pro Gly Ala Ser Val Lys Ile Ser Cys Lys Ala Thr Gly Tyr
        145                 150                 155                 160

Thr Phe Ser Asn Tyr Trp Ile Glu Trp Val Lys Gln Arg Pro Gly His
                            165                 170                 175

Gly Leu Glu Trp Ile Gly Glu Ile Leu Pro Gly Ser Gly Ser Ala His
                        180                 185                 190

Tyr Ser Glu Lys Phe Lys Asp Lys Ala Thr Phe Thr Ala Asp Thr Ser
                    195                 200                 205

Ser Asn Thr Ala Tyr Met Gln Leu Ser Ser Leu Thr Ser Glu Asp Ser
                210                 215                 220

Ala Val Tyr Phe Cys Thr Arg Ser Pro Pro Asn Pro Tyr Trp Gly Trp Gly
        225                 230                 235                 240

Gln Gly Thr Ser Val Thr Val Ser Ser
                        245

<210> SEQ ID NO 96
<211> LENGTH: 253
<212> TYPE: PRT
<213> ORGANISM: Artificial Sequence
<220> FEATURE:
<223> OTHER INFORMATION: CRB0069 scFv

<400> SEQUENCE: 96

Gln Pro Gly Leu Thr Gln Pro Pro Ser Ala Ser Gly Thr Pro Gly Gln
         1               5                  10                  15

Arg Val Thr Ile Ser Cys Thr Gly Ser Ser Ser Asn Val Gly Ala Gly
                        20                  25                  30

Tyr Thr Val His Trp Tyr Gln Gln Leu Pro Gly Thr Ala Pro Thr Leu
                    35                  40                  45

Leu Ile Tyr Asp Asn Asn Asn Arg Pro Ser Gly Val Pro Asp Arg Phe
                50                  55                  60

Ser Gly Ser Arg Ser Gly Thr Ser Ala Ser Leu Ala Ile Thr Gly Leu
         65                  70                  75                  80

Arg Ala Glu Asp Glu Ala Asp Tyr Tyr Cys Gln Ser Tyr Asp Arg Ser
                            85                  90                  95

Arg Val Tyr Val Phe Gly Thr Gly Thr Lys Leu Thr Val Leu Ser Gly
                        100                 105                 110

Gly Ser Thr Ser Gly Ser Gly Lys Pro Gly Ser Gly Glu Gly Ser Ser
```

```
            115                 120                 125
Gly Thr Gln Val Gln Leu Gln Gln Ser Gly Pro Gly Leu Val Lys Pro
        130                 135                 140

Ser Gln Thr Leu Ser Leu Thr Cys Ala Ile Ser Gly Asp Ser Val Ser
145                 150                 155                 160

Ser Asn Ser Ala Ala Trp Asn Trp Ile Arg Gln Ser Pro Ser Arg Gly
                165                 170                 175

Leu Glu Arg Leu Gly Arg Thr Tyr Tyr Arg Ser Lys Trp Tyr Asn Asp
            180                 185                 190

Tyr Ala Glu Ser Val Lys Ser Arg Ile Ile Ile Asn Ser Gly Thr Ser
        195                 200                 205

Lys Asn Gln Phe Ser Leu His Leu Asn Ser Val Thr Pro Glu Asp Thr
210                 215                 220

Ala Val Tyr Tyr Cys Gly Arg Ala Lys Asp Gly Trp Tyr Asp Ala Phe
225                 230                 235                 240

Asp Ile Trp Gly Gln Gly Thr Thr Val Thr Val Ser Ser
                245                 250
```

<210> SEQ ID NO 97
<211> LENGTH: 254
<212> TYPE: PRT
<213> ORGANISM: Artificial Sequence
<220> FEATURE:
<223> OTHER INFORMATION: CRB0072 scFv

<400> SEQUENCE: 97

```
Asp Ile Gln Met Thr Gln Ser Pro Ile Ser Leu Ser Ala Thr Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
    50                  55                  60

Ser Gly Ser Gly Thr Val Phe Thr Leu Thr Ile Ser Gly Leu Gln Pro
65                  70                  75                  80

Glu Asp Phe Ala Thr Tyr Cys Cys Gln Gln Ser His Ser Thr Ala Trp
                85                  90                  95

Thr Phe Gly Gln Gly Thr Lys Val Glu Ile Lys Ser Gly Gly Ser Thr
            100                 105                 110

Ser Gly Ser Gly Lys Pro Gly Ser Gly Glu Gly Ser Ser Gly Thr Glu
        115                 120                 125

Val Gln Leu Val Glu Thr Gly Gly Gly Leu Val Gln Pro Gly Ser Ser
    130                 135                 140

Leu Arg Leu Ser Cys Ala Thr Ser Gly Phe Thr Phe Ile Asn Tyr Gly
145                 150                 155                 160

Val His Trp Val Arg Gln Pro Pro Gly Lys Gly Leu Glu Trp Val Ala
                165                 170                 175

Ser Ile Trp Tyr Glu Gly Ser Asn Glu Lys Tyr Ala Asp Ser Val Lys
            180                 185                 190

Gly Arg Phe Thr Ile Ser Arg Asp Asn Ser Arg Tyr Thr Leu His Leu
        195                 200                 205

Gln Leu Asn Ser Leu Arg Ala Glu Asp Thr Ala Asp Tyr Tyr Cys Val
    210                 215                 220

Arg Asp Arg Gly Thr Gly Asp Tyr Arg Asn Ser Arg Phe Tyr Tyr Gly
```

-continued

```
                225                 230                 235                 240
Met Asp Val Trp Gly Gln Gly Thr Thr Val Thr Val Ser Ser
                    245                 250

<210> SEQ ID NO 98
<211> LENGTH: 245
<212> TYPE: PRT
<213> ORGANISM: Artificial Sequence
<220> FEATURE:
<223> OTHER INFORMATION: CRB0082 scFv

<400> SEQUENCE: 98

Ser Tyr Val Leu Thr Gln Pro Pro Ser Val Ser Val Ala Pro Gly Thr
1               5                   10                  15

Thr Ala Arg Leu Ser Cys Glu Ala Thr Lys Ile Gly Ser Gln Arg Leu
            20                  25                  30

His Trp Tyr Gln Gln Lys Pro Gly Gln Ala Pro Val Met Val Ile Ser
        35                  40                  45

Phe Asp Ser Asp Arg Pro Ser Gly Ile Pro Asp Arg Phe Ser Gly Ser
    50                  55                  60

Arg Ser Gly Asn Thr Ala Thr Leu Thr Ile Ser Gly Val Glu Ala Gly
65                  70                  75                  80

Asp Glu Ala Asp Tyr Tyr Cys Asn Ser Arg Asp Ser Ser Gly Tyr His
                85                  90                  95

Leu Val Phe Gly Gly Gly Thr Lys Leu Thr Val Leu Ser Gly Gly Ser
            100                 105                 110

Thr Ser Gly Ser Gly Lys Pro Gly Ser Gly Glu Gly Ser Ser Gly Thr
        115                 120                 125

Gln Val Gln Leu Gln Gln Ser Gly Pro Gly Leu Val Lys Pro Ser Gln
    130                 135                 140

Thr Leu Ser Leu Thr Cys Ala Ile Ser Gly Asp Ser Val Ser Ser Phe
145                 150                 155                 160

Thr Val Ala Trp Asn Trp Ile Arg Gln Ser Pro Ser Arg Gly Leu Glu
                165                 170                 175

Arg Leu Gly Arg Thr Tyr Arg Arg Ser Lys Asp Tyr Ala Glu Tyr Met
            180                 185                 190

Arg Ser Arg Leu Thr Ile Asn Ala Asp Thr Ser Lys Asn Gln Leu Ser
        195                 200                 205

Leu Gln Leu Asp Ser Val Thr Pro Asp Thr Ala Val Tyr Tyr Cys
    210                 215                 220

Ala Arg Gly Gln Asn Ser Ala Phe Asp Leu Trp Gly Gln Arg Thr Met
225                 230                 235                 240

Val Thr Val Ser Ser
                245

<210> SEQ ID NO 99
<211> LENGTH: 248
<212> TYPE: PRT
<213> ORGANISM: Artificial Sequence
<220> FEATURE:
<223> OTHER INFORMATION: CRB0084 scFv

<400> SEQUENCE: 99

Gln Pro Val Leu Thr Gln Pro Pro Ser Val Ser Val Ala Pro Arg Gln
1               5                   10                  15

Thr Ala Thr Ile Thr Cys Gly Gly Asn Tyr Ile Gly Ser Lys Ser Val
            20                  25                  30
```

His Trp Tyr Gln Gln Lys Pro Gly Gln Asp Pro Val Leu Val Val Asn
            35                  40                  45

Asp Asp Ser Asp Arg Pro Ser Gly Ile Pro Glu Arg Phe Ser Gly Ser
 50                  55                  60

Asn Ser Ala Asn Thr Ala Thr Leu Thr Ile Ser Gly Val Glu Ala Gly
 65                  70                  75                  80

Asp Glu Ala Asp Tyr Tyr Cys Gln Val Trp Asp Ser Ser Thr Glu Pro
                 85                  90                  95

Val Val Phe Gly Gly Gly Thr Lys Leu Thr Val Leu Ser Gly Gly Ser
            100                 105                 110

Thr Ser Gly Ser Gly Lys Pro Gly Ser Gly Glu Gly Ser Ser Gly Thr
            115                 120                 125

Gln Val Gln Leu Gln Gln Trp Gly Ala Gly Leu Leu Arg Pro Ser Glu
130                 135                 140

Thr Leu Ser Leu Thr Cys Thr Val Ser Gly Gly Ser Phe Ser Asp Ser
145                 150                 155                 160

Tyr Trp Thr Trp Ile Arg Gln Ser Pro Gly Lys Gly Leu Glu Trp Ile
                165                 170                 175

Gly Glu Asn Asn His Arg Gly Ser Thr Asn Tyr Ser Pro Thr Leu Arg
            180                 185                 190

Ser Arg Leu Ser Ile Ser Ile Asp Ser Ser Lys Asn Gln Phe Ser Leu
        195                 200                 205

Lys Leu Ser Ser Val Thr Ala Ala Asp Thr Ala Val Tyr Tyr Cys Ala
210                 215                 220

Arg Val Pro Tyr Arg Leu Arg Ser Arg Ile Phe Asp Val Trp Gly Gln
225                 230                 235                 240

Gly Thr Met Val Thr Val Ser Ser
                245

<210> SEQ ID NO 100
<211> LENGTH: 247
<212> TYPE: PRT
<213> ORGANISM: Artificial Sequence
<220> FEATURE:
<223> OTHER INFORMATION: CRB0089 scFv

<400> SEQUENCE: 100

Gln Thr Val Val Thr Gln Glu Pro Ser Val Ser Gly Ala Pro Gly Gln
1               5                   10                  15

Arg Val Thr Ile Ser Cys Thr Gly Ser Ser Ile Ile Gly Ala Gly
            20                  25                  30

Tyr Glu Val His Trp Tyr Gln His Leu Pro Gly Thr Ala Pro Lys Leu
            35                  40                  45

Leu Ile Tyr Asp Ser Ile Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Ser Ala Ile Phe
                 85                  90                  95

Gly Gly Gly Thr Lys Leu Thr Val Leu Ser Gly Gly Ser Thr Ser Gly
            100                 105                 110

Ser Gly Lys Pro Gly Ser Gly Glu Gly Ser Ser Gly Thr Gln Val Gln
            115                 120                 125

Leu Gln Glu Ser Gly Pro Gly Leu Val Lys Pro Ser Gln Thr Leu Ser
130                 135                 140

```
Leu Thr Cys Ala Ile Ser Gly Asp Ser Val Ser Ser Asn Ser Ala Ala
145                 150                 155                 160

Trp Asn Trp Ile Arg Gln Ser Pro Ser Arg Gly Leu Glu Trp Leu Gly
                165                 170                 175

Arg Thr Phe His Arg Ser Arg Trp Tyr Asn Glu Tyr Pro Val Ser Val
            180                 185                 190

Arg Ser Arg Ile Thr Ile Asn Pro Asp Thr Ser Asn Asn Gln Phe Thr
        195                 200                 205

Leu Gln Leu Asn Ser Val Thr Pro Asp Asp Thr Ala Val Tyr Tyr Cys
    210                 215                 220

Ala Arg Ala Pro Val Ala Gly Leu Thr Phe Asp Ile Trp Gly Gln Gly
225                 230                 235                 240

Thr Met Val Thr Val Ser Ser
                245
```

<210> SEQ ID NO 101
<211> LENGTH: 252
<212> TYPE: PRT
<213> ORGANISM: Artificial Sequence
<220> FEATURE:
<223> OTHER INFORMATION: CRB0088 scFv

<400> SEQUENCE: 101

```
Gln Pro Val Leu Thr Gln Ser Pro Pro Ala Ser Ala Ser Leu Gly Ala
1               5                   10                  15

Ser Val Lys Leu Thr Cys Thr Leu Ser Ser Gly His Ser Ser Tyr Ala
            20                  25                  30

Ile Ala Trp His Gln Gln Pro Glu Lys Gly Pro Arg Tyr Leu Met
        35                  40                  45

Lys Val Asn Ser Asp Gly Ser His Asn Lys Gly Asp Gly Ile Pro Asp
50                  55                  60

Arg Phe Ser Gly Ser Arg Ser Gly Ala Glu Arg Tyr Leu Thr Ile Ser
65                  70                  75                  80

Ser Leu His Ser Glu Asp Glu Ala Asp Tyr Tyr Cys Gln Thr Trp Gly
            85                  90                  95

Ala Gly Gly Val Val Phe Gly Gly Gly Thr Lys Leu Thr Val Leu Ser
            100                 105                 110

Gly Gly Ser Thr Ser Gly Ser Gly Lys Pro Gly Ser Gly Glu Gly Ser
            115                 120                 125

Ser Gly Thr Glu Val Gln Leu Leu Glu Ser Gly Gly Gly Leu Val Gln
        130                 135                 140

Pro Gly Gly Ser Leu Arg Leu Ser Cys Ala Ala Ser Gly Phe Thr Phe
145                 150                 155                 160

Ser Asp His Tyr Met Asp Trp Val Arg Gln Ala Pro Gly Lys Gly Leu
                165                 170                 175

Glu Trp Val Gly Arg Ile Arg Asn Lys Ala Asn Ser Tyr Thr Thr Glu
            180                 185                 190

Tyr Ala Ala Ser Val Lys Gly Arg Phe Thr Ile Ser Arg Asp Asp Ser
        195                 200                 205

Lys Lys Thr Leu Tyr Leu Gln Met Thr Ser Leu Lys Thr Asp Asp Thr
    210                 215                 220

Ala Leu Tyr Tyr Cys Ala Arg Asp Leu Gly Ala Ser Asp Ala Phe Asp
225                 230                 235                 240

Leu Trp Gly Gln Gly Thr Met Val Thr Val Ser Ser
                245                 250
```

```
<210> SEQ ID NO 102
<211> LENGTH: 112
<212> TYPE: PRT
<213> ORGANISM: Artificial Sequence
<220> FEATURE:
<223> OTHER INFORMATION: Consensus

<400> SEQUENCE: 102

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Val Ile Ser Gly Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Trp Gly Gln Gly Thr Leu Val Thr Val Ser Ser
            100                 105                 110
```